US006284487B1

(12) United States Patent
Stahl et al.

(10) Patent No.: US 6,284,487 B1
(45) Date of Patent: Sep. 4, 2001

(54) POLYNUCLEOTIDES ENCODING FATTY ACID TRANSPORT PROTEINS

(75) Inventors: Andreas Stahl, Allston; David J. Hirsch; Harvey F. Lodish, both of Brookline, all of MA (US)

(73) Assignee: Whitehead Institute for Biomedical Research, Cambridge, MA (US)

(*) Notice: Subject to any disclaimer, the term of this patent is extended or adjusted under 35 U.S.C. 154(b) by 0 days.

(21) Appl. No.: 09/232,191

(22) Filed: Jan. 14, 1999

Related U.S. Application Data

(60) Provisional application No. 60/110,941, filed on Dec. 4, 1998, provisional application No. 60/093,491, filed on Jul. 20, 1998, and provisional application No. 60/071,374, filed on Jan. 15, 1998.

(51) Int. Cl.[7] .............................. C12N 15/12; C12N 5/10; C12P 21/02; C07K 14/47
(52) U.S. Cl. .................. 435/69.1; 435/71.1; 435/471; 435/320.1; 435/252.3; 435/325; 536/23.1; 536/23.5; 536/24.5; 530/351
(58) Field of Search ..................... 435/69.1, 471, 435/71.1, 325, 320.1, 252–253; 536/23.1, 23.5, 24.5; 530/351

(56) References Cited

U.S. PATENT DOCUMENTS 4,935,450  6/1990  Cone, Jr. ............................. 514/728

OTHER PUBLICATIONS

Uchiyama, A. et al., "Molecular Cloning of cDNA Encoding Rat Very Long–chain Acyl–CoA Synthetase," *J. Biol. Chem.* 271(48):30360–30365 (1996).

Stuhlsatz–Krouper, S.M. et al., "Substitution of Alanine for Serine 250 in the Murine Fatty Acid Transport Protein Inhibits Long Chain Fatty Acid Transport," *J. Biol. Chem.* 273(44):28642–28650 (1998).

Watkins, P.A. et al., "Disruption of the *Saccharomyces cerevisiae* FAT1 Gene Decreases Very Long–chain Fatty Acyl–CoA Synthetase Activity and Elevates Intracellular Very Long–chain Fatty Acid Concentrations," *J. Biol. Chem.* 273(29):18210–18219 (1998).

Hirsch, D. et al., "A family of fatty acid transporters conserved from mycobacterium to man," *Proc. Natl. Acad. Sci.* 95:8625–8629 (1998).

Berger, J. et al., "A Novel Relative of the Very–Long–Chain Acyl–CoA Synthetase and Fatty Acid Transporter Protein Genes with a Distinct Expression Pattern," *Biochem. Biophys. Res. Commun.* 247:255–260 (1998).

Hui, T.Y. et al., "Characterization of the Murine Fatty Acid Transport Protein Gene and Its Insulin Response Sequence," *J. Biol. Chem.* 273(42):27420–27429 (1998).

Færgeman, N.J. et al., "Disruption of the *Saccharomyces cerevisiae* Homologue to the Murine Fatty Acid Transport Protein Impairs Uptake and Growth on Long–chain Fatty Acids," *J. Biol. Chem.* 272(13):8531–8538 (1997).

Schaap, F.G. et al., "Molecular cloning of fatty acid–transport protein cDNA from rat," *Biochem. Biophys. Acta* 1354:29–34 (1997).

Schaffer, J.E. and Lodish, H.F., "Expression Cloning and Characterization of a Novel Adipocyte Long Chain Fatty Acid Transport Protein," *Cell* (79):427–436 (1994).

Bonaldo, M.F. et al.; Data Submission; *Rattus norvegicus* cDNA clone; *Rattus norvegicus*; GenBank Accession No. AA817672;(1996).

Schaap, F.G. et al.; Data Submissioin; *Rattus norvegicus* fatty acid transport protein mRNA, complete cds.; *Rattus norvegicus*; GenBank Accession No. U89529; (1997).

Lee, N.H. et al.; Data Submission; Normalized rat heart, Bento Soares *Rattus sp.* cDNA clone; *Rattus sp.*; GenBank Accession No. AA799326; (1998).

Hui, T.Y. et al.; Data Submission; *Mus musculus* fatty acid transport protein (FATP) gene, exons 1–3; *Mus musculus*; GenBank Accession No. AF023256; (1997).

Schaffer, J.E. and Lodish, H.F.; Data Submission; *Mus musculus* fatty acid transport protein (FATP) mRNA, complete cds.; *Mus musculus*; GenBank Accession No. U15976 (1994).

Stahl, A. et al.; Data Submission; *Mus musculus* fatty acid transport protein 5 mRNA, complete cds.; *Mus musculus*; GenBank Accession No. AF072760; (1998).

Stahl, A. et al.; Data Submission; *Mus musculus* fatty acid transport protein 4 mRNA, partial cds.; *Mus musculus*; GenBank Accession No. AF072759; (1998).

Stahl, A. et al.; Data Submission; *Mus musculus* fatty acid transport protein 3 mRNA, partial cds.; *Mus musculus*; GenBank Accession No. AF072758; (1998).

Stahl, A. et al.; Data Submission; *Mus musculus* fatty acid transport protein 2 mRNA, complete cds.; *Mus musculus*; GenBank Accession No. AF072757; (1998).

Hui, T.Y. et al.; Data Submission; *Mus musculus* fatty acid transport protein (FATP) gene, exons 4–7; *Mus musculus*; GenBank Accession No. AF023257; (1997).

(List continued on next page.)

*Primary Examiner*—Christine Saoud
*Assistant Examiner*—Fozia Hamud
(74) *Attorney, Agent, or Firm*—Hamilton, Brook, Smith & Reynolds, P.C.

(57) ABSTRACT

A family of fatty acid transport proteins (FATPs) mediate transport of long chain fatty acids (LCFAs) across cell membranes into cells. These proteins exhibit different expression patterns among the organs of mammals. Nucleic acids encoding FATPs of this family, are described. Also described are methods to test FATPs for fatty acid transport function, and methods to identify inhibitors or enhancers of transport function. The altering of LCFA uptake by administering to the mammal an inhibitor or enhancer of FATP transport function of a FATP can decrease or increase calories available as fats, and can decrease or increase circulating fatty acids. The organ specificity of FATP distribution can be exploited in methods to direct drugs, diagnostic indicators and so forth to an organ.

80 Claims, 33 Drawing Sheets

OTHER PUBLICATIONS

Hui, T.Y. et al.; Data Submission; *Mus musculus* fatty acid transport protein (FATP) gene, exons 8–13 and complete cds.; *Mus musculus*; GenBank Accession No. AF023258; (1997).

Kamijo, K.; Data Submission; *Homo sapiens* mRNA for very–long–chain acyl–CoA synthetase, complete cds.; *Homo sapiens* (human); EMBL Accession No. D88308; (1996).

Harmon, C.M. et al., "Labelling of an 88 kDa adipocyte membrane protein by sulpho–N–succinimidyl long–chain fatty acids: inhibition of fatty acid transport," *Biochemical Society Transactions* 20(4):811–813 (1992).

Schaffer, J.E. et al., "Cloning and Structure–Function Analysis of Human Heart Fatty Acid Transport Protein," *Circulation* 96(8):2031 (1997).

Ghosh, B. et al., "Molecular cloning and sequencing of human palmitoyl–CoA ligase and its tissue specific expression," *Mol. Cell. Biochem.* 151:77–81 (1995).

Fitscher, B.A. et al., "Tissue distribution and cDNA cloning of a human fatty acid transport protein (hsFATP4)," *Biochmica et Biophysica Acta* 1443:381–385 (1998).

Abumrad, N., et al., "Membrane Proteins Implicated in Long–Chain Fatty Acid Uptake by Mammalian Cells: CD36, FATP and FABPm," *Biochimica et Biophysica Acta* 1441: 4–13 (1999).

Berk, P.D.,and Stump D.D., "Mechanisms of Cellular Uptake of Long–Chain Free Fatty Acids," *Molecular and Cellular Biochem.* 192:17–31 (1999).

Berk, P.D., et al., "Characterization of Membrane Transport Processes: Lessons from the Study of BSP, Bilirubin, and Fatty Acid Uptake," *Seminars In Liver Disease* 16(2):107–120 (1996).

Boisclair, Y.R., et al., "Three Clustered Sp1 Sites Are Required for Efficient Transcription of the TATA–Less Promoter of the Gene for Insulin–Like Growth Factor–binding Protein–2 from the Rat," *American Society Biochem.* 268(33):24892–24901 (1993).

De Simone, V.,and Cortese, R., "Transcription Factors and Liver–Specific Genes," *Biochimica et Biophysica Acta* 1132:119–126 (1992).

Fitscher, B.A., et al., "Protein–Mediated Facilitated Uptake Processes for Fatty Acids, Bilirubin, and Other Amphipathic Compounds (43987)," *Proc Soc Exp Biol Med* 212:15–23 (1996).

Frohnert, B.I., et al., "Identification of a Functional Peroxisome Proliferator–Responsive Element in the Murine Fatty Acid Transport Protein Gene," *J. of Biological Chem.* 274(7):3970–3977 (1999).

Glatz, J.F.C., et al., "Molecular Mechanism of Cellular Uptake and Intracellular Translocation of Fatty Acids," *Prostaglandins, Leukotrienes and Essential Fatty Acids* 57(1):3–9 (1997).

Göttlicher, M., et al., "Fatty Acids Activate a Chimera of the Clofibric Acid–Activated Receptor and the Glucocorticoid Receptor," *Proc. Natl. Acad. Sci. USA* 89:4653–4657 (1992).

Grimaldi, P.A., et al., "Long Chain Fatty Acids as Modulators of Gene Transcription in Preadipose Cells," *Molecular and Cellular Biochem.* 192:63–68 (1999).

Hamilton, J.A., "Fatty Acid Transport: Difficult or Easy?," *J. Lipid Res.* 39:467–481 (1998).

Hanson, R.W. "Regulation of Phosphoenolpyruvate Carboxykinase (GTP) Gene Expression" *Annu. Rev. Biochem.* 66:581–611 (1997).

Heinemeyer, T., et al., "Databases on Transcriptional Regulation: TRANSFAC, TRRD and COMPEL," *Nucleic Acids Res.* 26(1):362–367 (1998).

Heinemeyer[1], T. et al., "Expanding the TRANSFAC Database Towards an Expert System of Regulatory Molecular Mechanisms," *Nucleic Acids Res.* 27(1):318–322 (1999).

Hua[1], X., et al., "Synergistic Cooperation of TFE3 and Smad Proteins in TFG–β–Induced Transcription of the Plasminogen Activator Inhibitor–1 Gene," *Genes & Development* 12: 3084–3095 (1998).

Lai, E., "Regulation of Hepatic Gene Expression and Development," *Seminars in Liver Disease* 12(3):246–251 (1992).

Lee, Y.H., et al., "A Novel cis–Acting Element Controlling the Rat CYP2D5 Gene and Requiring Cooperativity between C/EBPβ and an SP1 Factor," *Molecular and Cellular Biology*, 14(2):1383–1394 (1994).

Martin, G., et al., "Coordinate Regulation of the Expression of the Fatty Acid Transport Protein and Acyl–CoA Synthetase Genes by PRARα and PPARγ Activators," *J. Biological Chem.* 272(45):28210–28217 (1997).

Memon, R.A., et al., "Regulation of Putative Fatty Acid Transporters and Acyl–CoA Synthetase in Liver and Adipose Tissue in ob/ob Mice," *Diabetes* 48:121–127 (1999).

Motojima, K., et al., "Expression of Putative Fatty Acid Transporter Genes Are Regulated by Peroxisome Proliferator–Activated Receptor α and γ Activators in a Tissue– and Inducer–Specific Manner," *J. Biol. Chem.* 273(27):16710–16714 (1998).

Rodenburg, R.J.T., et al., "A Functional Sp1 Binding Site Is Essential for the Activity of the Adult Liver–Specific Human Insulin–Like Growth Factor II Promoter," *Molecular Endocrinology* 11:237–250 (1997).

Rongnoparut, P., et al., "Isolation and Characterization of the Transcriptionally Regulated Mouse Liver (B–type) Phosphofructokinase Gene and Its Promoter," *J. Biological Chem.* 266(13):8086–8091 (1991).

Ryu, S., et al., "The Transcriptional Cofactor Complex CRSP is Required for Activity of the Enhancer–Binding Protein Sp1," *Nature* 397:446–450 (1999).

Schaffer, J.E.,and Lodish, H.F., "Molecular Mechanism of Long–Chain Fatty Acid Uptake," *TCM* 5(6):218–224 (1995).

Schoonjans, K., et al., "The Peroxisome Proliferator Activated Receptors (PPARs) and Their Effects on Lipid Metabolism and Adipocyte Differentiation," *Biochem. Biophys. Acta* 1302:93–109 (1996).

Sorensen, P.,and Wintersberger, E., "Sp1 and NF–Y Are Necessary and Sufficient for Growth–Dependent Regulation of the Hamster Thymidine Kinase Promoter[*]," *J. Biological Chem.* 274(43):30943–30949 (1999).

Stremmel, W., "Mechanism of Hepatic Fatty Acid Uptake," *J. Hepatology* 9:374–382 (1989).

Strausberg, R.; Data Submission; nc84e10.s1 NCI_CGAP_GC1 *Homo sapiens* cDNA clone Image:797514, *Homo sapiens*(human); EMBL Accession No. Aa581592; (1997).

Hillier, L. et. al.; Data Submission; zu10c02.r1 Soares testis NHT *Homo sapiens* cDNA clone 731426 5', *Homo sapiens*(human);EMBL Accession No. AA469992; (1997).

Strausberg, R.; Data Submission; no82f09.s1 NCI_CGAP_AA1 *Homo sapiens* cDNA clone Image:1113353 similar to TR:G563829 G563829 Fatty Acid Transport Protein, *Homo sapiens*(human); EMBL Accession No. Aa614135; (1997).

Hillier, L., et al.; Data Submission; zc44h06.r1 /Soares senescent fibroblasts NbHSF *Homo spiens* cDNA clone 325211 5' similar to PIR:A55093 A55093 fatty acid transport protein precursor—mouse, *Homo sapiens*(human); EMBL Accession No. W48808; (1996).

Strausberg, R.; Data Submission; nn89d05.s1 NCI_CGAP_Br2 *Homo sapiens* cDNA clone Image:1098345 similar to TR:G563829 G563829 Fatty Acid Transport Protein, *Homo sapiens*(human); EMBL Accession No. AA614445; (1997).

Strausberg, R.; Data Submission; ne19b11.s1 NCI_CGAP_Co3 *Homo sapiens* cDNA clone Image:881661, *Homo sapiens*(human); EMBL Accession No. AA470762; (1997).

| | mmFATP1 | mmFATP2 | mmFATP3 | mmFATP4 | mmFATP5 | rnFATP1 | rnVLACS | ceFATPa | ceFATPb | scFATP | mtFATP |
|---|---|---|---|---|---|---|---|---|---|---|---|
| mmFATP1 | 100.0 | | | | | | | | | | |
| mmFATP2 | 50.1 | 100.0 | | | | | | | | | |
| mmFATP3 | 51.8 | 53.3 | 100.0 | | | | | | | | |
| mmFATP4 | 72.6 | 48.4 | 51.7 | 100.0 | | | | | | | |
| mmFATP5 | 50.2 | 54.0 | 54.4 | 50.8 | 100.0 | | | | | | |
| rnFATP1 | 97.5 | 49.7 | 51.6 | 71.4 | 50.4 | 100.0 | | | | | |
| rnVLACS | 50.7 | 95.2 | 53.0 | 50.9 | 53.6 | 50.3 | 100.0 | | | | |
| ceFATPa | 54.1 | 48.6 | 47.2 | 53.6 | 47.0 | 53.9 | 49.1 | 100.0 | | | |
| ceFATPb | 55.7 | 48.8 | 46.8 | 54.2 | 47.3 | 54.9 | 49.0 | 60.3 | 100.0 | | |
| scFATP | 45.5 | 43.2 | 42.3 | 47.0 | 42.7 | 45.5 | 43.9 | 45.3 | 43.1 | 100.0 | |
| mtFATP | 47.5 | 47.8 | 43.9 | 48.2 | 47.2 | 47.1 | 48.3 | 44.9 | 44.5 | 42.3 | 100.0 |

FIG. 2 mmFATP3 DNA sequence

```
ACGACTCACTATAGGGAGAGACCTATGACGTCGCATGCAC  40
GCGTAAGCTTGGGCCCTCGAGGATCCTCTAGAGCGGCC    80
GCCGACCCCGAAAGCTCTGAGACGCGGTCCAGTCTGCCT  120
GCCGTCTCGCGTACCTGGCCCGGAGCAGCCGACACAC    160
CTTCCTCATCCACCGCGCCACGCTTTACCTACCGCGAG   200
GCTGAGCGCGAGACCAACGGATTGCTCGCGCCTTTCTCC  240
GCGCACGGGCTGGACCGCGGGCGCCGAGGCTCGGGCAG   280
GGGCAGCACTGAGGAAGCGCACGCGTGCCGCCTCCGGCT  320
GGAGATGCCGCTGCTAGAGGACGACCGCGCCCCTCTGG   360
CACCCGGGCGACCGTGCCGCCTGCTCCTCCAGCGGGCCC  400
```

FIG. 5A

```
GGATTTCCTTTGGATTTCGTTCGGACTGGCCAAAGCTGGC 440
CTGCGCACGGCCTTTGTGCCCACGGCTTTACGCCGAGGAC 480
CCCTGCTGCACTGCCTCGCAGCTGCGGTGCGAGTGCGCT 520
CGTGCTGGCCACAGAGTTCCTGGAGTCCCTGGAGCCGGAC 560
CTGCCGGCCTTGAGAGCCATGGGCTCCACCTATGGGCGA 600
CGGGCCCTGAAACTAATGTAGCTGGAATCAGCAATTTGCT 640
ATCGGAAGCAGCAGACCAAGTGGATGAGCCAGTCCCGGG 680
TACCTCTCTGCCCCCAGAACATAATGGACACCTGCCTGT 720
ACATCTTCACCTCTGGCACTACTGGCCTGCCCAAGGCTGC 760
TCGAATCAGTCATCTGAAGGTTCTACAGTGCCAGGCATTC 800
TACCATCTGTGTGGAGTCCACCAGGAGGACGTGATCTACC 840
TGCACTCCCACTGTACCACATGTCTGGCTCCCTTCTGGG 880
CATTGTGGGCTGCTTGGGCATTGGGGCACGGTGGTGCTG 920
AAACCCAAGTTCTCAGCTAGCCAGTTCTGGACGATTGCC 960
AGAAACACAGGGTGACAGTGTTCCAGTACATTGGGGAGTT 1000
GTGCCGATACCTCGTCAACCAGCCCCGAGCAAGGCAGAG 1040
TTTGACCATAAGGTGCGCTTGCCAGTGGCAGTGGGTTGC 1080
GCCCAGACACCTGGGAGCGTTTCCTGCGGCGATTTGGACC 1120
TCTGCAGATACTGGAGACGTATGGCATGACAGAGGGCAAC 1160
GTAGCTACGTTCAATTACACAGGACGGCAGGGTGCAGTGG 1200
GGCGAGCTTCCTGGCTTTACAAGCACATCTTCCCCTTCTC 1240
CTTGATTCGATACGATGTCATGACAGGGAGCCTATTCGG 1280
AATGCCCAGGGCACTGCATGACCACATCTCCAGGTGAGC 1320
CAGGCCTACTGGTGGCCCCAGTGAGCCAGCAGTCCCCCTT 1360
CCTGGGCTATGCTGGGGCTCCGGAGCTGGCCAAGGACAAG 1400
CTGCTGAAGGATGTCTTCTGGTCTGGGACGTTTTCTTCA 1440
ATACTGGGGACCTCTTGGTCTGTGATGAGCAAGGCTTTCT 1480
TCACTTCCACGATCGTACTGGAGACACCATCAGGTGGAAG 1520
GGAGAGAATGTGGCCACAACTGAAGTGGCTGAGGTCTTGG 1560
AGACCCTGGACTTCCTTCAGGAGGTGAACATCTATGGAGT 1600
CACGGTGCCAGGGCACGAAGGCAGGGCAGGCATGGCGGCC 1640
TTGGCTCTGCGGCCCCGCAGGCTCTGAACCTGGTGCAGC 1680
TCTACAGCCATGTTTCTGAGAACTTGCCACGGTATGCCCG 1720
ACCTCGGTTTCTCAGGCTCCAGGAATCTTTGGCCACTACT 1760
GAGACCTTCAAACAGCAGAAGGTTAGGATGGCCAATGAGG 1800
GCTTTGACCCAGTGTACTGTCTGACCCACTCTATGTTCT 1840
GGACCAAGATATAGGGGCCTACCTGCCCCTCACACCTGCC 1880
CCGTACAGTGCCCTCCTGTCTGGAGACCTTCGAATCTGAA 1920
ACCTTCCACTTGAGGGACGGGCTCGGAGGGTACAGGCCAC 1960
CATGGCTGCACCAGGGAGGGTTTTGGGTATCTTTTGTAT 2000
ATGGAGTCATTATTTTGTAATAAACAGCTGGAGCTTAAAA 2040
AAAAAAAAAAAAAAAAAAAAAAAAAAAAAAAAAAAAAAA 2080
AAAAAAA 2087
```

FIG. 5B mmFATP3 protein sequence

```
AADPESSESGCSLAWRLAYLAREQPIHIFLIHGAQRFSYAEAERESNRIA  50
RAFLRARGWIGGRRGSGRGSTEEGARVAPPAGDAAARGTTAPPLAPGATV 100
ALLLPAGPDFLWIWFGLAKAGLRTAFVPTALRRGPLLHCLRSCGASALVL 150
ATEFLESLEPDLPALRAMGLHLWATGPEINVAGISNLLSEAADQVDEFVP 200
GYLSAPQNIMDICLYIFTSGTTGLPKAARISHLKVLQCQGFYHLCGVHQE 250
DVIYLALPLYHMSGSLLGIVGCLGIGATVVLKPKFSASQFWDDCQKHRVT 300
VFQYIGELCRYLVNQPPSKAEFDHKVRLAVGSGLRPDIWERFLRRFGPLQ 350
ILETYGMTEGNVATFNYTGRQGAVGRASWLYKHIFPFSLIRYDVMIGEPI 400
RNAQGHCMTTSPGEPGLLVAPVSQQSPFLGYAGAPELAKDKLLKDVFWSG 450
DVFFNIGDLLVCDEQGFLHFHDRTGDTIRWKGENVATTEVAEVLEILDFL 500
QEVNIYGVIVPGHEGRAGMAALALRPPQALNLVQLYSHVSENLPPYARPR 550
FLRLQESLATTETFKQQKVRMANEGFDPSVLSDPLYVLDQDIGAYLPLTP 600
ARYSALLSGDLRI 613
```

FIG. 6 mmFATP4 DNA sequence

```
CCCACGCGTCCGCCCACGCGTCCGGCATGGCCAAGCTGGG  40
CGTGGAGGCGGCTCTCATCAACACCAACCTTAGGCGGGAT  80
GCCCTGCGCCACTGTCTTGACACCTCAAAGGCACGAGCTC 120
TCATCTTTGGCAGTGAGATGCCCTCAGCTATCTGTGAGAT 160
CCATGCTAGCCTGGAGCCCACACTCAGCCTCTTCTGCTCT 200
GGATCCTGGGAGCCCAGCACAGTGCCCGTCAGCACAGAGC 240
ATCTGGACCCTCTTCTGGAAGATGCCCCGAAGCACCTGCC 280
CAGTCACCCAGACAAGGGTTTTACAGATAAGCTCTTCTAC 320
ATCTACACATGGGCACCACGGGCTACCCAAAGCTGCCA   360
TTGTGGTGCACAGCAGGTATTATCGTATGGCTTCCCTGGT 400
GTACTATGGATTCGCATGCGGCCTGATGACATTGTCTAT  440
GACTGCCTCCCCCTCTACCACTCAAGCAGGAAACATCGTG 480
GGGATTGGCAGTGCTTACTCCACGGCATGACTGTCGGTCAT 520
CCGGAAGAAGTTCTCAGCCTCCCGGTTCTGGCATGATTGT 560
ATCAAGTACAACTGCACAGTGGTACAGTACATTGGCAGC  600
TCTGCCGCTACCTCCTGAACCAGCCACCCGTGAGGCTGA  640
GTCTCGGCACAAGGTGCGCATGGCACTGGGCAACGGTCTC 680
CGGCAGTCCATCTGGACCGACTTCTCCAGCCGTTTCCACA 720
```

FIG. 7A

```
TCCCCCAGGTGGCTGAGTTCTATGGGCCACTGAATGCAA 760
CTGTAGCCTGGCCAACTTTGACAGCCGGTGGGGCCTGT 800
GGCTTCAATAGCCGCATCCTGTCCTTTGTGTACCCTATCC 840
GTTTGGTACGTGTCAATCAGGATACCATGGAACTGATCCG 880
GGACCCGATCGAGTCTGCATTCCTGTCAACCAGGTCAG 920
CCAGGCCAGCTGGTGGGTGGCATCATCCAGCAGGACCCTC 960
TGCCCGTTTGACGGGTACCTCAACCAGGGTGCCAACAA 1000
CAAGAAGATTGCTAATCATGTCTTCAAGAAGGGGACCAA 1040
GCCTACCTCACTGGTGACGTCCTGGTGATGGATGAGCTGG 1080
GTTACCTGTACTTCCGAGATGGCACTGGGACACGTTCCG 1120
CTGGAAAGGGAGAATGTATCTACCACTGAGGTGGAGGGC 1160
ACACTCAGCCGCCTGCTTCATATGGCAGATGTGGCAGTTT 1200
ATGGTGTTGAGGTGCCAGGAACTGAAGGCCGAGCAGGAAT 1240
GGCTGCCGTTGCAAGTCCCATCAGCAACTGTGACCTGGAG 1280
AGCTTTGCACAGACCTTGAAAAAGGAGCTGCCTCTGTATG 1320
CCCGCCCCATCTTCCTGCGCTTCTTGCCTGAGCTGCACAA 1360
GACAGGGACCTTCAAGTTCCAGAAGACAGAGTTGCGGAAG 1400
GAGGGCTTTGACCCATCTGTTGTGAAAGACCCGCTGTTCT 1440
ATCTGGATGCTGGGAAGGGCTGCTACGTTGCACTGGACCA 1480
GGAGGCCTATACCCGCATCCAGGCAGGCGAGGAGAAGCTG 1520
TGATTTCCCCCTACATCCCTCTGAGGGCCAGAAGATGCTG 1560
GATTCAGAGCCCTAGCGTCCACCCAGAGGGTCCTGGGCA 1600
ATGCCAGACCAAAGCTAGCAGGGCCGCACCTCCGCCCT 1640
AGGTGCTGATCTCCCCTCTCCCAAACTGCCAAGTCACTCA 1680
CTGCCGCTTCCCCGACCCTCCAGAGGCTTTCTGTGAAAGT 1720
CTCATCCAAGCTGTGTCTTCTGGTCCAGCGGTGGCCCCTG 1760
GCCCCAGGGTTTCTGATAGGCTCCTTTAGGATGGTATCTT 1800
GGGTCCAGCGGGCCAGGGTGTGGGAGAGGAGTCACTAAGA 1840
TCCCTCCAATCAGAAGGGAGCTTACAAAGGAACCAAGCCA 1880
AAGCCTGTAGACTCAGGAAGCTAAGTGGCAGAGACTATA 1920
GTGGCCAGTCATCCATGTCCACAGAGGATCTTGGTCCAG 1960
AGCTGCCAAAGTGTCACCTCTCCCTGCCTGCACCTCTGGG 2000
GAAAGAGGACAGCATGTGGCCACTGGGCACCTGTCTCAA 2040
GAAGTCAGGATCACACACTCAGTCCTTGTTTCTCCAGGTT 2080
CCCTTGTTCTTGTCTCGGGCAGCCAGGGACGAGTGTCCTG 2120
TCTGTCCTTCCTGCCTGTCTGTCAGTCTGTGTTGCTTCTC 2160
CATCTGTCCTAGCCTGAGTGTGCGGTGGAACAGGCATGAGG 2200
AGAGTGTGCCTCAGGGCCAATAAACTCTGCCTTGACTCC 2240
TCTTAAAAAAAAAAAAAAAAAAAAAAAAAAAAAAAAAAAAA 2280
AAAAAAAAAAAAAAAAAAAAAA 2301
```

FIG. 7B mmFATP4 protein sequence

HASAHASGMAKLGVEAALININLRRDALRHCLDTSKARAL 40
IFGSEMASAICEIHASLEPTLSLFCSGSWEPSIVPVSIEH 80
LDPLLEDAPKHLPSHPDKGFIDKLFYIYTSGTTGLPKAAI 120
VVHSRYYRMASLVYYGFRMRPDDIVYDCLPLYHSSRKHRG 160
DWQCLLHGMIVVIRKKFSASRFWDDCIKYNCIVVQYIGEL 200
CRYLLNQPPREAESRHKVRMALGNGLRQSIWIDFSSRFHI 240
PQVAEFYGATECNCSLGNFDSRVGACGFNSRILSFVYPIR 280
LVRVNEDIMELIRGPDGVCIPQPGQPGQLVGRIIQQDPL 320
RRFDGYLNQGANNKKIANDVFKKGDQAYLTGDVLVMDELG 360
YLYFRDRTGDIFRWKGENVSTTEVEGILSRLLHMADVAVY 400
GVEVPGTEGRAGMAAVASPISNCDLESFAQILKKELPLYA 440
RPIFLRFLPELHKTGTFKFQKTELRKEGFDPSVVKDPLFY 480
LDARKGCYVALDQFAYIRIQAGEEKL 507 mmFATP5 DNA sequence

CACTCATCAGAGCTAAGAGAGACTACACGCTCTCATCTAC 40
TTCAGAAAGAGCCAATGCCATGGGTATTTGGAAGAAACTA 80
ACCTTACTGCTGTTGCTGCTTCTGCTGGTTGCCCTGGGGC 120
AGCCCCCATGGCCAGCAGCTATGCTCTCGCCCTGCCGTTG 160
GTTCCTGGGAGACCCCACATGCCTTGTGCTGCTTGGCTTG 200
GCATTGCTGGGCAGACCCTGGATCAGCTCCTGGATGCCCC 240
ACTGGCTGAGCCTGGTACGAGCAGCTCTTACCTTATTCCT 280
ATTGCCTCTACAGCCACCCCCAGGGCTACGCTGGCTGCAT 320
AAAGATGTGGCTTTCACCTTCAAGATGCTTTTCTATGGCC 360
TAAAGTTCAGGCGACGCCTTAACAAACATCCTCCAGAGAC 400
CTTTGTGGATGCTTTAGAGCGGCAAGCACTGGCATGGCCT 440
GACCGGGTGGCCTTGGTGTGTACTGGGTCTCAGGGCTCCT 480
CAATCACAAATAGCCAGCTGGATGCCAGGTCCTGTCAGCC 520
AGCATGGGTCCTGAAAGCAAAGCTGAAGGATGCCGTAATC 560
CAGAACACAAGAGATGCTGCTGCTATCTTAGTTCTCCCGT 600
CCAAGACCATTTCTGCTTTGAGTGTGTTTCTGGGGTTGCC 640
CAAGTTGGGCTGCCCTGTGGCCTGGATCAATCCACACAGC 680
CGAGGGATGCCCTTGCTACACTCTGTACGGAGCTCTGGGG 720
CCAGTGTGCTGATTGTGGATCCAGACCTCCAGGAGAACCT 760
GGAAGAAGTCCTTCCCAAGCTGCCTAGCTGAGAACATTCAC 800

```
TGCTTCTACCTTGGCCACAGCTCACCCACCCGGGAGTAG 840
AGGCTCTGGGAGCTTCCCTGGATGCTGCACCTTCTGACCC 880
AGTACCTGCCAGCCTTCGAGCTACGATTAAGTGGAAATCT 920
CCTGCCATATTCATCTTTACTTCAGGACCACTGGACTCC 960
CAAAGCCAGCCATCTTATCACATGAGCCGGTCATACAAGT 1000
GAGCAACGTGCTGTCCTTCTGTGGATGCAGAGCTGATGAT 1040
GTGGTCTATGACGTCCTACCTCTGTACCATACGATAGGGC 1080
TTGTCCTTGGATTCCTTGGCTGCTTACAAGTTGGAGCCAC 1120
CTGTGTCCTGGCCCCAAGTTCTCTGCCTCCCGATTCTGG 1160
GCTGAGTGCCGGCAGCATGGCGTAACAGTCATCTTGTATG 1200
TGGTGAAATCCTGCGGTACTTGTGTAACGTCCCTGAGCA 1240
ACCAGAAGACAAGATACATACAGTCGCTTGGCCATGGA 1280
ACTGGACTTCCGGCAAATGTGTGGAAAACTTCCAGCAAC 1320
GCTTTGGTCCCATTCGGATCTGGAATTCTACGGATCCAC 1360
AGAGGGCAATGTGGGCTTAATGAACTATGTGGCCACTGC 1400
GGGCCTGTGCCAAGGACCAGCTGCATCCTTCGAATGCTGA 1440
CTCCCTTTCAGCTTGTACAGTTCGACATAGACAGCAGA 1480
GCCTCTGAGGACAAACAGGGTTTTTGCATTCCTGTGCAG 1520
CCAGGAAAGCCAGGACTTCTTTTCACCAAGGTTCGAAAGA 1560
ACCAACCCTTCCTGGCCTACGGTGGTTCCCAGGCCCAGTC 1600
CAATGGAAACTTGTTGCCAATGTACGACGCGTACGAGAC 1640
CTGTACTTCAACACTGGGACGTGCTCACCTTGCACCAGG 1680
AAGCCTTCTTCTACTTTCAAGACGCCTTGGTGACACCTT 1720
CCCGTGGAAGGGCGAAAACGTATCTACTGGAGAGGTGGAG 1760
TGTGTTTTGTCTAGCCTAGACTTCCTAGAGGAAGTCAATG 1800
TCTATGGTGTGCCTGTGCCAGGGTGTGAGGGTAAGGTTGG 1840
CATGCCTGCTGTGAAACTGGCTCCTGCCAAGACTTTTGAT 1880
GGGCAGAAGCTATACCAGCATGTCCGCTCCTGGCTCCCTG 1920
CCTATGCCACACCTCATTTCATCGGTATCCAGGATTCCCT 1960
GGAGATCACAAACACCTACAAGCTGGTAAAGTCACGGCTG 2000
GTCCGTCAGGGTTTTCATGTCGGGATCATTGCTGACCCCC 2040
TCTACATACTGGACAACAAGGGCAGACCTTCCGGAGTCT 2080
GATGCCAGATGTGTACCAGGCTGTGTGTGAAGGAACCTGG 2120
AATCTCTGACCACCTAGCCAACTGGAAGGCAATCCAAAAG 2160
TGTAGAGATTGACACTAGTCAGCTTCACAAAGTTGTCCGG 2200
GTTCCAGATGCCCATGCCCAGTAGTACTTAGAGAATAAA 2240
CTTCAATGTGTATACAAAAAAAAAAAAAAAAAAAAAAA 2277
```

FIG. 9B mmFATP5 protein sequence

```
MALALRWFLGDPTCLVLLGLALLGRPWISSWMPHWLSLVG  40
AALTLFLLPLQPPPGLRWLHKDVAFTFKMLFYGLKFRRRL  80
NKHPPETFVDALERQALAWPDRVALVCTGSEGSSTINSQL 120
DARSCQAAWVLKAKLKDAVIQNIRDAAAILVLPSKTISAL 160
SVFLGLAKLGCPVAWINPHSRGMPLLHSVRSSGASVLIVD 200
PDLQENLEEVLPKLLAENIHCFYLGHSSPTPGVEALGASL 240
DAAPSDPVPASLRATTKWKSPAIFIFTSGTTGLPKPAILS 280
HERVIQVSNVLSFCGCRADDVVYDVLPLYHTIGLVLGFLG 320
CLQVGATCVLAPKFSASRFWAECRQHGVTVILYVGEILRY 360
LCNVPEQPEDKIHIVRLAMGIGLRANWKNFQQRFGPIRI  400
WEFYGSTEGNVGLMNYVGHCGAVGRTSCIIRMLTPFELVQ 440
FDIETAEPLRDKQGFCIPVEPGKPGLLLIKVRKNQPFLGY 480
RGSQAESNRKLVANVRRVGDLYFNIGDVLTLDQEGFFYFQ 520
DRLGDIFRWKGENVSTGEVECVLSSLDFLEEVNVYGVPVP 560
GCECKVGMAAVKLAPGKTFDGQKLYQHVRSWLPAYATPHF 600
IRIQDSLETTNIYKLVKSRLVREGFDVGIIADPLYILLNK 640
AQTFRSLMPDVYQAVCEGIWNL 663
```

FIG. 10 hsFATP2 DNA sequence

```
ATGGGATTGACTCTTTCCTGGACAAAGTGGATGAAGTATC  40
AACTGAACCTATCCCAGAGTCATGGAGGTCTGAAGTCACT  80
TTTTCCACTCCTGCCTTATACATTTATACTTCTGGAACCA 120
CAGGTCTTCCAAAAGCAGCCATGATCACTCATCAGCGCAT 160
ATGGTATGGAACTGGCCTCACTTTTGTAAGCGGATTGAAG 200
GCAGATGATGTCATCTATATCACTCTGCCCTTTTACCACA 240
GTCCTGCACTACTGATTGGCATTCACGGATGTATTGTGGC 280
TGGTGCTACTCTTGCCTTGCGGACTAAATTTTCAGCCAGC 320
CAGTTTTGGGATGACTGCAGAAAATACAACGTCACTGTCA 360
TTCAGTATATCGGTGAACTGCTTCGGTATTTATGCAACTC 400
ACCACAGAAACCAAATGACGTGATCATAAAGTCAGACTG  440
GCACTGGGAAATGCTTACGAGGACATGTGTGGAGACAAT  480
TTGTCAAGAGATTTGGGGACATATGCATCTATGAGTTCTA 520
TGCTGCCACTGAAGGCAATATTGGATTTATGAATTATGCG 560
AGAAAAGTTGGTGCTGTTGGAAGAGTAAACTACCTACAGA 600
AAAAAATCATAACTTATGACCTGATTAAATATGATGTGCA 640
GAAAGATGAACCTGTCCGTGATGAAAATGGATATTGCGTC 680
AGAGTTCCAAAGGTCAAGTTGGACTTCTGGTTTGCAAAA  720
TCACACAACTTACACCATTTAATGGCTATGCTGGAGCAAA 760
GGCTCAGACAGAGAAGAAAAACTGAGAGATGTCTTTAAG  800
```

FIG. 11A

```
AAAGGAGACCTCTATTTCAACAGTGGAGATCTCTTAATGG 840
TTGACCATGAAAATTTCATCTATTTCCACGACAGAGTTGG 880
AGATACATTCCGGTGGAAAGGGGAAAATGTGGCCACCACT 920
GAAGTTGCTGATATAGTTGGACTGGTTGATTTTTTTCCAA 960
GGAAGTAAAATGTTTATGGGAGTGCATGGGCCAAGATNAT 1000
GGAGGTTCCAATTGGCATGGCNTTCCNTTCAAAATGGAAA 1040
GAAAACCATGGAATTTGATGGAAAGAAATTTTTTCAGNAC 1080
ATTGCTGATAACCNACCTAGTTATGCAAGGCCCCGGTTTT 1120
NTAAGAANACAGGACACCATTGAGATCACTGGAATTTTTA 1160
AACACCGCAAAATGACCTTTGGTGGAGGACGGCTTTAACC 1200
CNGCTGTCATCAAAGATGCCTTGTATTTTCTTGGATGACA 1240
CAGCAAAAATGTATGTGCCTATGACTGAGGACATNTATAA 1280
TGCCATAAGTGNTAAAACCCTGAAATTNTGAATATCCCA 1320
GGAGGATAATTCAACATTCCAGAAAGAAACTGAATGGAC 1360
AGCCACTTGATATAATCCAACTTTAATTTGATTGAAGATT 1400
GTGAGGAAATTTGTAGGAAATTTGCATACCCGTAAAGGG 1440
AGACTTTTTTTAAATAACAGTTGAGTCTTTGCAAGTAAAA 1480
GATTTAGAGATTATTATTTTCAGTGTGCACCTACTGTTT 1520
GTATTTGCAAACTGAGCTTGTTGCAGGGAAGGCATTATTT 1560
TTTAAAATACTTAGTAAATTAAAGAACACCAACATGTGAA 1600
AAAAAAAAAAAAAAAAAAAAAA 1622
``` hsFATP2 protein sequence

```
YIYTSGTTGLPKAAMTTHQRIWYGTGLTFVSGLKADDVIY 40
ITLPFYHSAALLTGTHGCIVAGATLALRTKFSASQFWDDC 80
RKYNVTVIQYIGELLRYLCNSPQKFNDRDHKVRLALGNGL 120
RGDWRQFVKRFGDICTYEFYAATEGNIGFMNYARKVGAV 160
GRVNYLQKKTTTYDLIKYDVEKDEPVRDENGYCVRVPKGE 200
VGLLVCKTTQLTPFNGYAGAKAQTEKKKLRDVFKKGDLYF 240
NSGDLLMVDHENFTYFHDRVGDTFRWKGENVATTEVADIV 280
GLVDFF 286
```

FIG. 12 hsFATP3 DNA sequence

```
CAATTCGGGACCCCCAGGGGCACTGTATGGCCACATCTCC 40
AGGTGAGCCAGGGCAAGTTGCTAAAGGATGTCTTCCGGCC 80
TGCCCATGTTTTCTTCAACACTGGGACCTGCTGGTCTGC 120
GATGACCAAGGTTTTCTCCGCTTCCATGATCGTACTGGAG 160
```

FIG. 13A

```
ACACCTTCAGGTGGAAAGGGGAGAATGTGGCCACAACCGA 200
GGTGGCAGAGGTCTTCGAGGCCCTAGATTTTCTTCAGGAG 240
GTGAACGTCTATGGAGTCACTGTGCCAGGGCATGAAGGCA 280
GGGCTGGAATGGCAGCCCTAGTTCTGCGTCCCCCCACGC  320
TTTGGACCTTATGCAGCTCTACACCCACGTGTCTGAGAAC 360
TTGCCACCTTATGCCCGGCCCCGATTCCTCAGGCTCCAGG 400
AGTCTTTGGCCACCACAGAGACCTTCAAACAGCAGAAAGT 440
TGGATGGCAAATGAGGGCTTGACCCCAGCACCCTGTCT   480
GACCCACTGTACGTTCTGGACCAGGCTGTAGGTGCCTACC 520
TGCCCCTCACAACTGCCCGGTACAGCGCCCTCCTGGCAGG 560
AAACCTTCGAATCTGAGAACTTCCACACCTGAGGCACCTG 600
AGAGGAACTCTGTGGGGTGCGGCCGTTGCAGGTGTAC    640
TGGGCTGTCAGGATCTTTTCTATACCAGAACTGCGGTCA  680
CTATTTTGTAATAAATGTGGCTGGAGCTGATCCAGCTGTC 720
TCTGACCTACAAAAAAAAAAAAAAAAAAAAAAAA 753
```

FIG. 13B hsFATP3 protein sequence

```
QFGTPRGTVWPHLQVSQGKLLKDVFRPGDVFFNIGDLLVC 40
DDQGFLRFHDRIGDTFRWKGENVATTEVAEVFEALDFLQE 80
VNVYGVTVPGHEGRAGMAALVLRPPHALDIMQLYTHVSEN 120
LPPYARPRFLRLQESLATTETFKQQKVRMANEGFDPSTLS 160
DPLYVLDQAVGAYLPLTTARYSALLAGNLRI 191
```

FIG. 14 hsFATP4 DNA sequence

```
TCAAGTACAACTGCACGATTGTCATANCATTGGTGAACTG 40
TGCCGNTACCTCCTGAACCAGCCACCGCGGGAGGCAGAAA 80
ACCAGCACCAGGTTCGCATGGCACTAGGCAATGGCCTCCG 120
GCAGTCCATCTGGACCAACTTTTCCAGCCGCTTCCACATA 160
CCCCAGGTGGCTGAGTTYTACGGGGCCACAGAGTGCAACT 200
GTAGCCTGGGCAACTTCGACAGCCAGGTGGGGCCTGTGG  240
TTTCAATAGCCGCATCCTGTCCTTCGTGTACCCCATCCGG 280
TTGGTACGTGTCAACGAGGACACCATGGAGCTGATCCGGG 320
GGCCGGACGGCGTCTGCATTCCCTGCCAGCCAGGTGAGCC 360
GGGCCAGCTGGTCGGCCGCATCATCCAGAAGACCCCCTG  400
CGCCGCTTCGATGGCTACCTCAACCAGGCGCCAACAACA  440
AGAAGATTGCCAAGCATGTCTTCAAGAAGGGGACCAGGC  480
CTACCTTACTGGTCATGTGCCTGGTCATGGACCAGCTGGGC 520
```

FIG. 15A

TACCTGTACTTCCGAGACCGCACTGGGGACACGTTCCGCT 560
GGAAAGGTGAGAACGTGTCCACCACCGAGGTGGAAGGCAC 600
ACTCAGCCGCCTGCTGGACATGGCTGACGTGGCCGTGTAT 640
GGTGTCGAGGTGCCAGGAACCGAGGCCGGCCGGAATCG 680
CTGCTGTCGCCAGCCCACTGGCAACTGTCACCTGGCAGC 720
GCTTTGCTCAGGTC 734

FIG. 15B hsFATP4 protein sequence

IGELCRYLLNQPPREAENQHQVRMALGNGLRQSIWINFSS 40
RFHIPQVAEFYGATECNCSLGNFDSQVGACGFNSRILSFV 80
YPIRLVRVNEDIMELIRGPDGVCIPCQPGEPGQLVGRIIQ 120
KDPLRRFDGYLNQGANNKKIAKDVFKKGDQAYLTGDVLVM 160
DELGYLYFRDRTGDIFRWKGENVSTTEVEGTLSRLLDMAD 200
VAVYGVEVPGIEG 213

FIG. 16 hsFATP5 DNA sequence

CNTGCCTCTTGTACCACGTCATGGGACTTTGTCGTTGCGA 40
TCCTCGGCTGCTTAGATCTCGGAGCCACCTGTGTTCTGGC 80
CCCCAAGTTCTCTACTTCCTGCTTCTGGCATGACTGTCGG 120
CAGCATGGCGTCACAGTCATCCTGTATGTGGCGCAGCTCC 160
TGCCNTACTTGTGTAACATTCCCAGCAACCAGAGGACCG 200
GACACATACAGTCCGCCTGGCAATGGGCAATCGACTACGG 240
GCTCATGTGTCGGGAGACCTTCAGCAGCGTTTCGGTCCT 280
ATTTCGGATCTNGGAAGTCTTACGGCCTYCCACAGAAGG 320
GCAACATGGGGCTTTAGTTCAACTATTGTTGGGGCGCTG 360
CGGGGSCCTGCGGCAAAGATGGAGCTTGCCTCCTCCGAA 400
TGCTGTCCCCTTTGAGCTGGTGCAGTTCGACATGGAGGC 440
GGCGGAGCCTGTGACGCACAATCAGGCCTTCTGCATCCCT 480
GTAGGCCTACGCCAGCCGGCCTGCTGTTGACCAAGGTGG 520
TAAGCCAGCAACCTTCGTGCGCTACGGCGGCCCCGAGA 560
GCTGTCGGAACGGAAGCTGGTCGCAACGTGCGGCAATCG 600
GGCGACGTTTACTACAACACCGGGGACGTACTGGCCATGG 640
ACCGCGAAGGCTTCCTCTACTTCCGCGACCGACTCGGGA 680
CACCTTCCGATGGAAGGGCGAGAACGTGTCCACGACGAG 720
GTGGAGGGCGTGTTGTCGCAGGTGGACTTCTTCCAACAGG 760
TTAACGTGTATGCCGTCGTCCGTGCCAGGTTGTCAGGGTAA 800
GGTGGGCATGGCTGCCTGTCGCCATTAGCCCCCGGCCAGACT 840

FIG 17A

```
TTCGACGGGAGAAGTTGTACCAGCACGTTCGCGCTTGGC 880
TCCCTGCCTACGCTACCCCCATTTCATCGGCATCCAGGA 920
CGCCATGGAGGTCACCAGCACGTTCAAACTGATGAAGACC 960
CGGTTGGTGCGTGAGGGCTTCAATGTCGGGATCGTCGTTG 1000
ACCCTCTGTTTGTACTGGACAACCGGGCCAGTCCTTCCG 1040
GCCCCTGACGGCAGAAATGTACCAGGCTGTGTGTGAGGGA 1080
ACCTGGAGGCTCTGATCACCTGGCCAACCCACTGGGGTAG 1120
GGATCAAAGCCAGCCACCCCACCCCAACACACTCGGTGT 1160
CCCTTTCATCCTGGGCCTGTGTGAATCCAGCCTGGCCAT 1200
ACCCTCAACCTCAGTGGGCTGGAAATGACAGTGGGCCCTG 1240
TAGCAGTGGCAGAATAAACTCAGMTGYGTTCACAGAAA 1278
```

FIG. 17B hsFATP5 protein sequence

```
EGQHGALVQLLLGALRGPGGKDGACLLRMLSPFELVQFDM 40
EAAEPVRDNQGFCIPVGLGEPGLLLIKVVSQQPFVGYRGP 80
RELSERKLVRNVRQSGDVYYNIGDVLAMDREGFLYFRDRL 120
GDIFRWKGENVSIHEVEGVLSQVDFLQQVNVYGVCVPGCE 160
GKVGMAAVALAPGQIFDGEKLYQHVRAWLPAYATPHFIR 199
```

FIG. 18 hsFATP6 DNA sequence

```
CGCTTGTGTGTTAAAGAAGAAATTTTCAGCAAGCCAGTTT 40
TGCAGTGACTGCAAGAAGTATGATGTGACTGTGTTTCAGT 80
ATATTGGAGAACTTTGTCGCTACCTTTGCAAACAATCTAA 120
GAGAGAAGGAGAAAACGATCATAAGGTCCGTTTGGCAATT 160
GGAAATGGCATACGGAGTCATGTATGGAGAATTTTTAG 200
ACAGATTTGGAAATATAAAGGTGTGTGAACTTTATGCAGC 240
TACCGAATCAAGCATATCTTTCATGAACTACACTGGGAGA 280
ATTGGAGCAATTGGAGAACAAATTGTTTTACAAACTTC 320
TTTCCACTTTTGACTTAATAAGTATGACTTTCAGAAAGA 360
TGAACCCATGAGAATGAGCAGGGTTGGGTATTCATGAGA 400
AAAGGAGACCTGGACTTCTCATTTCTCGAGTCAATGCAA 440
AAAATCCCTTCTTTGCCTATGCTGGGCCTTATAAGCACAC 480
AAAAGACAAATTGCTTTGTGATGTTTTAAGAAGGAGAT 520
GTTTACCTTAATACTGGAGACTTAATAGTCCAGGATCAGG 560
ACAATTCCTTTATTTTTGGACCGTACTGGAGACACTTT 600
CAGATGGAAGGAGAAAATGTCGCAACCACTGAGGTTGCT 640
GATGTTATTGGAATGTTGGATTTCATACAGGAAGCAAACG 680
TCTATGGTGTGGCTATATCAGGTTATGAAGGAAGAGCAGG 720
```

FIG. 19A

AATGGCTTCTATTATTTTAAAACCAAATACATCTTTAGAT 760
TTGGAAAAGTTTATGAACAAGTTGTAACATTTCTACCAG 800
CTTATGCTTGTCCACGATTTTTAAGAATTCAGGAAAAAT 840
GGAAGCAACAGGAACATTCAAACTATTGAAGCATCAGTTG 880
GTGGAAGATGGATTTAATCCACTGAAATTTCTGAACCAC 920
TTTACTTCATGGATAACTTGAAAAGTCTTATGTTCTACT 960
GACCAGGGAACTTTATGATCAAATAATGTTAGGGAAATA 1000
AAACTTTAAGATTTTTATATCTAGAACTTTCATATGCTTT 1040
CTTAGGAAGAGTGAGAGGGGGTATATGATTCTTTATGAA 1080
ATGGGGAAAGGGAGCTAACATTAATTATGCATGTACTATA 1120
TTTCCTTAATATGAGAGATAATTTTTTAATTGCATAAGAA 1160
TTTTAATTTCTTTTAATTGATATAAACAGAGTTGATTATT 1200
CTTTTTATCTATTTGGAGATTCAGTGCATAACTAAGTATT 1240
TTCCTTAATACTAAAGATTTTAAATAATAAATAGTGGCTA 1280
GCCGTTTGGACAATCACTAAAAATGTACTTTCTAATAAGT 1320
AAAATTTCTAATTTTGAATAAAAGATTAAATTTTACTGAA 1360
A 1361

FIG. 19B hsFATP6 protein sequence

ACVLKKKFSASQFWSDCKKYDVIVFQYIGELCRYLCKQSKREGEKDHKVR 50
LAIGNGIRSDWWREFLDRFGNIKVCELYAATESSISFMNYTGRIGAIGRT 100
NLFYKLLSTFDLIKYDFQKDEPMRNEQGWVFMRKRRPGLLISRVNAKNPF 150
FGYAGPYKHIKDKLLCDVFKKGDVYLNIGDLIVQDQDNFLYFWDRTGDIF 200
RWKGENVATTEVADVIGMLDFIQEANVYGVAISGYEGRAGMASIILKPNT 250
SLDLEKVYEQVVIFLPAYACPRFLRIQEKMEATGIFKLLKHQLVEDGFNP 300
LKTSEPLYFMDNLKKSYVLLTRELYDQIMLGEIKL 335

FIG. 20 mtFATP DNA sequence

TAGTCGATAACGTCAAGGACGCTCTGCGGGCCTGCGCACC 40
TTCCTGAGGTTGGTCGACAACCAATTCGACATTTCGCAAA 80
CGAATCGAGGGCTTACGTGTCCGATTACTACGGCGGCGCA 120
CACACAACGGTCAGGCTGATCGACCTGGCAACTCGGATGC 160
CGCCAGTGTTGGCGGACACCCGGTCATTGTCGGTGGGC 200
AATGACCGGCTGCTGGCCCGGCCGAATTCCAAGGCGTCG 240
ATCGGCACGGTGTTCCAGGACCGGCCGCTCGCTACGGTG 280
ACCGAGTCTTCCTGAAATTCGGCGATCAGCAGCTGACCTA 320
CCGCGACGCTAACGCCACCGCCAACCGGTACGCCGCGGTG 360

FIG. 21A

```
TTGGCCGCCGCGCGTCGGCCCCGGCGACGTCGTTGCCA 400
TCATGTTGCGTAACTCACCCAGCACAGTCTTGGCGATGCT 440
GGCCACGGTCAAGTGCGGCGCTATCGCCGGCATGCTCAAC 480
TACCACCAGCCGGCGACGTGTTGGCGCACAGCCTGGGTC 520
TGCTGGACGCGAAGGTACTCATCGCAGAGTCCGACTTGGT 560
CAGCGCGTCGCCGAATGCGGCGCTGCGCGGCCGGTA 600
GCGGCGACGTGCTGACCGTCGAGGACGTGCAGCCGATTCG 640
CCACAACGGCGCCCGCCACCAACCGGCGTCGGCGTCGGC 680
GGTGCAAGCCAAAGACACCGCGTTCTACATCTTCACCTCG 720
GGCACCACCGGATTTCCCAAGGCCAGTGTCATCACGCATC 760
ATCGGTGCCTGCGGCGCTGCCGTCTTCCAGGCATCG 800
GCTGCGGCTGAACGGTTCCGACACGCTCTACAGCTGCCTG 840
CCGCTGTACCACAACAACCGGTTAACGGTCGCGGTGTCGT 880
CCGTCATCAATTCTCGGGCGACCCTGCGCCTGGGTAAGTC 920
GTTTTCGCCGTCGCCGTTCTCGCATCAGGTGATTGCCAAC 960
CGGCGACGGCGTTCGTCTACATGGCGCAAATCTGCCGTT 1000
ATCTGCTCAACCAGCCGGCCAAGCCGACCGACCGTGCCCA 1040
CCAGGTCGCGGTGATCTGCGGTAACGGGCTGCGGCCGGAG 1080
ATCTGGGATCAGTTCACCACCCGCTTGGGGTCGCGCGGG 1120
TGTGCCAGTTCTACGCCGCCAGCGAAGGCAACTCGCCCTT 1160
TATCAACATCTTCAACGTCGCCAGGACCGCCGGGGTATCG 1200
CCGATCCGCTTGCCTTTGTCGAATACCACCTCGACACCG 1240
GCGATCCGCTGCGGCATGCCAGCGGGCGAGTCCGTCGGGT 1280
ACCGACCGTGAACCGGCCTGTTGCTTAGCCGGGTCAAC 1320
CGGCTGCAGCCGTTCGACGGCTACACCGACCCGGTTGCCA 1360
GCGAAAAGAAGTTGGTGCGCAACGCTTTTCGAGATGGCGA 1400
CTGTTGGTTCAACACCGGTGACGTGATGAGCCCGCACGGC 1440
ATGGGCCATGCCGCCTTCGTCGATCGGCTGGGCGACACCT 1480
TCGGCTGGAAGGGCGAGAATGTCGCCACCACTCAGGTCGA 1520
AGCGGCACTGGCCTCCGACCAGACCGTCGAGGAGTCCACG 1560
GTCTACGGCGTCCAGATTCCGCGCACCGCGGGCGCCG 1600
GAATGGCGGCGATCACACTGCGCGCTGGCGCCGAATTCGA 1640
CGGCCAGGCGCTGGCCCGAACGGTTTACGGTCACTTGCCC 1680
GGCTATCCACTTCCGCTCTTTGTTCGGGTAGTCGGGGTCGC 1720
TGCCGCACACCACGACGTTCAACAGTCGCAAGGTCGAGTT 1760
GCGCAACCAGGCTATGGCGCCGACATCGAGGATCGCTG 1800
TACGTACTGGCCGGCCGGACGAAGCATATGTGCCGTACT 1840
ACGCCGAATACCCTGAGGAGGTTTCGCTCGGAAGGCGACC 1880
GCAGGGCTACGGGATTCGGGCGCAGTCTCGATACCGCA 1920
CTGGACGCTCGACGGTAACCAGGCACTATGCATGCGTCGG 1960
TTCAACACCGCCGGCCCTCAGCCGGTCGTTCAACACCGCCG 2000
GCGTTAG 2007
```

FIG. 21B mtFATP protein sequence

```
msdyyggahttvrlidlatmprvladtpvivrgamtgll  40
arpnskasigtvfqdraarygdrvflkfgdqqltyrdana  80
tanryaavlaargvgpgdvvgimlrnspstvlamlatvkc  120
gaiagmlnyhqrgevlahslglldakvliaesdlvsavae  160
cgasrgrvagdvltvedverfattapatnpasasavqakd  200
tafyiftsgttgfpkasvmthhrwlralavfggmglrlkg  240
sdtlysclplyhnnaltvavssvinsgatlalgksfsasr  280
fwdevianrratafvyigeicryllnqpakptdrahqvrvi  320
cgnglrpeiwdefttrfgvarvcefyaasegnsafinifn  360
vprtagvspmplafveydldtgdplrdasgrvrrvpdgep  400
glllsrvnrlqpfdgytdpvasekklvrnafrdgdcwfnt  440
gdvmspqgmghaafvdrlgdtfrwkgenvattqveaalas  480
dqtveectvygvqiprtggragmaaitlragaefdgqala  520
rtvyghlpgyalplfvrvvgslahttfksrkvelmqay  560
gadiedplyvlagpdegyvpyyaeypeevslgrrpqg  597
```

FIG. 22 dmFATP partial DNA

```
         10        20        30        40
         |         |         |         |
GCTCTCTGGGCCTATATCAAGCTGCTGAGGTACACGAAGC  40
GCCATGAGCGGCTCAACTACACGGTGGCGGACGTCTTCGA  80
ACGAAATGTTCAGGCCCATCCGGACAAGGTGGCTGTGGTC 120
AGTGAGACGCAACGCTGGACCTTCCGTCAGGTGAACGAGC 160
ATGCGAACAAGGTGGCCAATGTGCTGCAGGCTCAGGGCTA 200
        210       220       230       240
         |         |         |         |
CAAAAGGGCGATGTGGTGGCCCTGTTGCTGGAGAACCGC  240
GCCGAGTACGTGGCCACCTGGCTGGGTCTCTCCAAGATCG 280
GTGTGATCACACCGCTGATCAACACGAATCTGCGCGGTCC 320
CTCCCTGCTGCACAGCATCACGGTGGCCCATTGCTCGGCT 360
CTCATTTACGGCGAGGACTTCCTGGAAGCTGTCACCGACG 400
        410       420       430       440
         |         |         |         |
TGGCCAAGGATCTGCCAGCGAACCTCACACTCTTCCAGTT 440
CAACAACGAGAACAACAACAGCGAGACGGAAAAGAACATA 480
CCGCAGGCCAAGAATCTGAACGCGCTGCTGACCACGGCCA 520
GCTATGAGAAGCCTAACAAGACGCAGGTTAACCACCACGA 560
CAAGCTGGTCTACATCTACACCTCCGGCACCACAGGATTG 600
        610       620       630       640
         |         |         |         |
CCAAAGGCTGCGGTTATCTCTCACTCCCGTTATCTGTTTA 640
TCGCTGCTGGCATCCACTACACCATGGGTTTCCAGGAGGA 680
GGACATCTTCTACACGCCCTTGCCTTTGTACCACACCGCT 720
GGTGGCATTATGTGCATGGGTCAGTCGGTGCTCTTTGGCT 760
CCACGGTCTCCATTCGCAAGAAGTTCTCGGCATCCAACTA 800
        810       820       830       840
         |         |         |         |
TTTCGCCGACTGCGCCAAGTATAATGCAACTATTGGTCAG 840
TATATCGGTGAGATGGCTCGCTACATTCTAGCTACGAAAC 880
CCTCGGAATACGACCAGAAACACCGAGTGCGTCTGGTCTT 920
TGGAAACGGACTGCGACCGCAGATTTGGCCACAGTTTGTG 960
CAGCGCTTCAACATTGCCAAGGTTGGCGAGTTCTACGGCG 1000
       1010      1020      1030      1040
         |         |         |         |
CCACCGAGGGTAATGCGAACATCATGAATCATGACAACAC 1040
GGTGGGCGCCATCGGCTTTGTGTCGCGCATCCTGCCCAAG 1080
ATCTACCCAATCTCGATCATTCGCGCCGATCCGGACACCG 1120
GAGAGCCCATTAGAGATAGGAATGGCCTATGCCAACTGTG 1160
CGCTCCCAACGAGCCAGGCGTATTCATCGGCAAGATCGTC 1200
```

FIG. 23A dmFATP partial DNA

```
           1210      1220      1230      1240
     ..ılıııılıııılıııılıııılıııılıııılı
     AAAGGAAATCCTTCTCGCGAATTCCTCGGATACGTCGATG 1240
     AAAAGGCCTCCGCGAAGAAGATTGTTAAGGATGTGTTCAA 1280
     GCATGGCGATATGGCTTTCATCTCCGGAGATCTGCTGGTT 1320
     GCCGACGAGAAGGGTTATCTGTACTTCAAGGATCGCACCG 1360
     GTGACACCTTCCGCTGGAAGGGCGAGAATGTTTCCACCAG 1400
           1410      1420      1430      1440
     ıııılıııılıııılıııılıııılıııılıııılıııl
     CGAGGTGGAGGCGCAAGTCAGCAATGTGGCCGGTTACAAG 1440
     GATACCGTCGTTTACGGCGTAACCATTCCGCACACCGAGG 1480
     GAAGGGCCGGCATGGCCGCCATCTATGATCCGGAGCGAGA 1520
     ATTGGACCTCGACGTCTTCGCCGCTAGCTTGGCCAAGGTG 1560
     CTGCCCGCGTACGCTCGTCCCCAGATCATTCGATTGCTCA 1600
           1610      1620      1630      1640
     ıııılıııılıııılıııılıııılıııılıııılıııl
     CCAAGGTGGACCTGACTGGAACCTTTAAGCTGCGCAAGGT 1640
     AGACCTGCAGAAGGAGGGCTACGATCCGAACGCGATCAAG 1680
     GACGCGCTGTACTACCAGACTTCCAAGGGTCGGTACGAGC 1720
     TGCTCACGCCCCAGGTTTACGACCAGGTGCAGCGCAACGA 1760
     AATCCGCTTCTAAGAGCTGCAATAGAGTTGTGTCTGAACC 1800
           1810      1820      1830      1840
     ıııılıııılıııılıııılıııılıııılıııılıııl
     TTGCCTTTTGCCCAATATGCTGTTAATTAGTTTGTAAGGC 1840
     TAAGTGTAGTAGAGGAAAATCGGGGGAAATCGGCAGCAAA 1880
     GATCATTCAGCCTAGGAGAGATGCATCCGAAGCACATTTC 1920
     CATGTCAACAATGCACTTTTGTATATCGTAAGCATATATA 1960
     TATCGTATATCGTAAACGTAGTTGTATCTGCATTTGTGTA 2000
           2010      2020      2030      2040
     ıııılıııılıııılıııılıııılıııılıııılıııl
     GATGATAGCCTCCTATACGCATTTCAATTGTTTTTAGCGT 2040
     GCTAAAGAACCTTGTTAAATGCAATTTCAGCTATTGTTTA 2080
     GTCAGTTTTAGTGGCATTTACACTTCCATTCTCGTTGCGT 2120
     TTCGTTTTTGCCTGTACATATGAGAAGCTCTGATGTTTTT 2160
     GTATCAAATAAAGTTTTTCCTTCACCACGGACCACGTGA 2200
           2210      2220      2230      2240
     ıııılıııılıııılıııılıııılıııılıııılıııl
     AAAAAAAAAAAAAAAAAAAAA 2221
```

FIG. 23B dmFATP partial protein

```
         10         20         30         40
ALWAYIKLLRYTKRHERLNYTVADVFERNVQAHPDKVAVV  40
SETQRWTFRQVNEHANKVANVLQAQGYKKGDVVALLLENR  80
AEYVATWLGLSKIGVITPLINTNLRGPSLLHSITVAHCSA 120
LIYGEDFLEAVTDVAKDLPANLTLFQFNNENNNSETEKNI 160
PQAKNLNALLTTASYEKPNKTQVNHHDKLVYIYTSGTTGL 200
        210        220        230        240
PKAAVISHSRYLFIAAGIHYTMGFQEEDIFYTPLPLYHTA 240
GGIMCMGQSVLFGSTVSIRKKFSASNYFADCAKYNATIGQ 280
YIGEMARYILATKPSEYDQKHRVRLVFGNGLRPQIWPQFV 320
QRFNIAKVGEFYGATEGNANIMNHDNTVGAIGFVSRILPK 360
IYPISIIRADPDTGEPIRDRNGLCQLCAPNEPGVFIGKIV 400
        410        420        430        440
KGNPSREFLGYVDEKASAKKIVKDVFKHGDMAFISGDLLV 440
ADEKGYLYFKDRTGDTFRWKGENVSTSEVEAQVSNVAGYK 480
DTVVYGVTIPHTEGRAGMAAIYDPERELDLDVFAASLAKV 520
LPAYARPQIIRLLTKVDLTGTFKLRKVDLQKEGYDPNAIK 560
DALYYQTSKGRYELLTPQVYDQVQRNEIRF           590
```

FIG. 24 drFATP partial DNA

```
         10         20         30         40
AGTGTAGATACCACAGGAACGTTTAAAATCCAGAAGACCA  40
GACTGCAAAGGGAAGGATACGATCCACGGCTCACAACTGA  80
CCAGATCTACTTCCTAAACTCCAGAGCAGGGCGTTACGAG 120
CTTGTCAACGAGGAGCTGTACAATGCATTTGAACAAGGGC 160
AGGATTTCCCTTT                            173
```

FIG. 25 drFATP partial protein

```
         10         20         30         40
SVDTTGTFKIQKTRLQREGYDPRLTTDQIYFLNSRAGRYE  40
LVNEELYNAFEQGQDFP                         57
```

FIG. 26 ceFATPa coding only DNA

```
                10        20        30        40
ATGAAGCTGGAGGAGCTTGTGACAGTTATGCTTCTCACAG  40
TGGCTGTCATTGCTCAGAATCTTCCGATTGGAGTAATATT  80
GGCTGGAGTTCTTATTTTATACATCACAGTGGTTCATGGA 120
GATTTCATTTATAGAAGTTATCTTACGTTGAATAGGGATT 160
TAACAGGATTGGCTCTAATTATTGAAGTCAAAATCGACCT 200
               210       220       230       240
ATGGTGGAGGTTGCATCAGAATAAAGGAATCCATGAACTG 240
TTTTGGATATTGTGAAAAGAATCCAAATAAGCCGGCGA   280
TGATTGACATCGAGACGAATACAACAGAAACATACGCAGA 320
GTTCAATGCACATTGTAATAGATATGCCAATTATTTCCAG 360
GGTCTTGGCTATCGATCCGGAGACGTTGTCGCCTTGTACA 400
               410       420       430       440
TGGAGAACTCGGTCGAGTTTGTGGCCGCGTGGATGGGACT 440
CGCAAAAATCGGAGTTGTAACGGCTTGGATCAACTCGAAT 480
TTGAAAAGAGAGCAACTTGTTCATTGTATCACTGCGAGCA 520
AGACAAAGGCGATTATCACAAGTGTAACACTTCAGAATAT 560
TATGCTTGATGCTATCGATCAGAAGCTGTTTGATGTTGAG 600
               610       620       630       640
GGAATTGAGGTTTACTCTGTCGGAGAGCCCAAGAAGAATT 640
CTGGATTCAAGAATCTCAAGAAGAAGTTGGATGCTCAAAT 680
TACTACGGAACCAAAGACCCTTGACATAGTAGATTTTAAA 720
AGTATTCTTTGCTTCATCTATACAAGTGGTACTACTGGAA 760
TGCCAAAAGCCGCTGTCATGAAGCACTTCAGATATTACTC 800
               810       820       830       840
GATTGCCGTTGGAGCCGCAAAATCATTCGGAATCCGCCCT 840
TCTGATCGTATGTACGTCTCGATGCCAATTTATCACACTG 880
CAGCTGGAATTCTTGGAGTTGGGCAAGCTCTGTTGGGTGG 920
ATCATCGTGTGTCATTAGAAAAAAATTCTCGGCTAGCAAC 960
TTTTGGAGGGATTGTGTAAAGTATGATTGTACAGTTTCAC 1000
              1010      1020      1030      1040
AATACATTGGAGAGATTTGTCGGTACTTGTTGGCTCAGCC 1040
AGTTGTGGAAGAGGAATCCAGGCATAGAATGAGATTGTTG 1080
GTTGGAAACGGACTCCGTGCTGAAATCTGGCAACCATTTG 1120
TAGATCGATTCCGTGTCAGAATTGGAGAACTTTATGGTTC 1160
AACTGAAGGAACTTCATCTCTCGTGAACATTGACGGACAT 1200
```

FIG. 27A ceFATPa coding only DNA

```
           1210          1220          1230          1240
    ┴┴┴┴┴┴┴┴┴┴┴┴┴┴┴┴┴┴┴┴┴┴┴┴┴┴┴┴┴┴┴┴┴┴┴┴┴┴┴┴┴┴
    GTCGGAGCTTGCGGATTCTTGCCAATATCCCCATTAACAA  1240
    AGAAAATGCATCCGGTTCGATTAATTAAGGTTGATGATGT  1280
    CACTGGAGAAGCAATCCGAACTTCCGATGGACTTTGCATT  1320
    GCATGTAATCCAGGAGAGTCTGGAGCAATGGTGTCGACGA  1360
    TCAGAAAAAATAATCCATTATTGCAATTCGAGGGATATCT  1400
           1410          1420          1430          1440
    ┴┴┴┴┴┴┴┴┴┴┴┴┴┴┴┴┴┴┴┴┴┴┴┴┴┴┴┴┴┴┴┴┴┴┴┴┴┴┴┴┴┴
    GAATAAGAAGGAAACGAATAAAAAGATTATCAGAGATGTC  1440
    TTCGCAAAGGGAGATAGTTGCTTTTTGACTGGAGATCTTC  1480
    TTCATTGGGATCGTCTTGGTTATGTATATTTCAAGGATCG  1520
    TACTGGAGATACTTTCCGTTGGAAGGGAGAGAATGTGTCG  1560
    ACTACTGAAGTCGAGGCAATTCTTCATCCAATTACTGGAT  1600
           1610          1620          1630          1640
    ┴┴┴┴┴┴┴┴┴┴┴┴┴┴┴┴┴┴┴┴┴┴┴┴┴┴┴┴┴┴┴┴┴┴┴┴┴┴┴┴┴┴
    TGTCTGATGCAACTGTTTATGGTGTAGAGGTTCCTCAAAG  1640
    AGAGGGAAGAGTTGGAATGGCGTCAGTTGTTCGAGTTGTA  1680
    TCGCATGAGGAAGATGAAACTCAATTTGTTCATAGAGTTG  1720
    GAGCAAGACTTGCCTCTTCGCTTACCAGCTACGCGATTCC  1760
    TCAGTTTATGCGAATTTGTCAGGATGTTGAGAAACAGGT  1800
           1810          1820          1830          1840
    ┴┴┴┴┴┴┴┴┴┴┴┴┴┴┴┴┴┴┴┴┴┴┴┴┴┴┴┴┴┴┴┴┴┴┴┴┴┴┴┴┴┴
    ACATTCAAACTTGTGAAGACGAATCTACAACGATTAGGTA  1840
    TCATGGATGCTCCTTCAGATTCAATTTACATCTACAATTC  1880
    TGAAAATCGCAATTTTGTGCCGTTCGACAATGATTTGAGG  1920
    TGCAAGGTCTCACTGGGAAGTTATCCATTTTAA         1953
```

FIG. 27B ceFATPa coding only protein

```
          10         20         30         40
    ......|.........|.........|.........|......
    MKLEELVTVMLLTVAVIAQNLPIGVILAGVLILYITVVHG   40
    DFIYRSYLTLNRDLTGLALIIEVKIDLWWRLHQNKGIHEL   80
    FLDIVKKNPNKPAMIDIETNTTETYAEFNAHCNRYANYFQ  120
    GLGYRSGDVVALYMENSVEFVAAWMGLAKIGVVTAWINSN  160
    LKREQLVHCITASKTKAIITSVTLQNIMLDAIDQKLFDVE  200
          210        220        230        240
    ......|.........|.........|.........|......
    GIEVYSVGEPKKNSGFKNLKKKLDAQITTEPKTLDIVDFK  240
    SILCFIYTSGTTGMPKAAVMKHFRYYSIAVGAAKSFGIRP  280
    SDRMYVSMPIYHTAAGILGVGQALLGGSSCVIRKKFSASN  320
    FWRDCVKYDCTVSQYIGEICRYLLAQPVVEEESRHRMRLL  360
    VGNGLRAEIWQPFVDRFRVRIGELYGSTEGTSSLVNIDGH  400
          410        420        430        440
    ......|.........|.........|.........|......
    VGACGFLPISPLTKKMHPVRLIKVDDVTGEAIRTSDGLCI  440
    ACNPGESGAMVSTIRKNNPLLQFEGYLNKKETNKKIIRDV  480
    FAKGDSCFLTGDLLHWDRLGYVYFKDRTGDTFRWKGENVS  520
    TTEVEAILHPITGLSDATVYGVEVPQREGRVGMASVVRVV  560
    SHEEDETQFVHRVGARLASSLTSYAIPQFMRICQDVEKTG  600
          610        620        630        640
    ......|.........|.........|.........|......
    TFKLVKTNLQRLGIMDAPSDSIYIYNSENRNFVPFDNDLR  640
    CKVSLGSYPF.                               651
```

FIG. 28 ceFATPb coding only DNA

```
         10        20        30        40
ATGAGGGAAATGCCGGACAGTCCCAAGTTTGCGTTAGTCA  40
CGTTTGTTGTGTATGCAGTGGTTTTGTACAATGTCAACAG  80
CGTTTTCTGGAAATTTGTATTCATCGGATATGTTGTATTT 120
AGGCTGCTTCGCACTGATTTTGGAAGAAGAGCACTTGCCA 160
CGTTACCTAGAGATTTTGCGGGACTGAAGCTCTTAATATC 200
         210       220       230       240
GGTTAAGTCGACAATTCGTGGCTTGTTCAAGAAAGATCGC 240
CCAATTCATGAAATCTTTTTGAATCAGGTGAAACAGCATC 280
CAAACAAAGTGGCGATTATTGAAATTGAAAGTGGTAGGCA 320
GTTGACGTATCAAGAATTGAATGCGTTAGCTAATCAGTAT 360
GCTAACCTTTACGTGAGTGAAGGTTACAAAATGGGCGACG 400
         410       420       430       440
TTGTCGCTTTGTTTATGGAAAATAGCATCGACTTCTTTGC 440
AATTTGGCTGGGACTTTCCAAGATTGGAGTCGTGTCGGCG 480
TTCATCAACTCAAACTTGAAGTTGGAGCCATTGGCACATT 520
CGATTAATGTTTCGAAGTGCAAATCATGCATTACCAATAT 560
CAATCTGTTGCCGATGTTCAAAGCCGCTCGTGAAAAGAAT 600
         610       620       630       640
CTGATCAGTGACGAGATCCACGTGTTTCTGGCTGGAACTC 640
AGGTTGATGGACGTCATAGAAGTCTTCAGCAAGATCTCCA 680
TCTTTTCTCTGAGGATGAACCTCCAGTTATAGACGGACTC 720
AATTTTAGAAGCGTTCTGTGTTATATTTACACTTCCGGTA 760
CTACCGGAAATCCAAAGCCAGCCGTCATTAAACACTTCCG 800
         810       820       830       840
TTACTTCTGGATTGCGATGGGAGCAGGAAAAGCATTTGGA 840
ATTAATAAGTCAGACGTTGTGTACATTACGATGCCAATGT 880
ATCACTCTGCCGCCGGTATCATGGGTATTGGATCATTAAT 920
TGCATTCGGGTCGACCGCTGTTATTAGGAAAAAGTTTTCG 960
GCAAGCAACTTCTGGAAAGATTGCGTCAAGTACAACGTCA 1000
         1010      1020      1030      1040
CAGCGACACAGTACATTGGAGAAATCTGCAGGTATCTTCT 1040
GGCAGCGAATCCATGTCCTGAAGAGAAACAACACAACGTG 1080
CGATTGATGTGGGGAAATGGTTTGAGAGGACAAATTTGGA 1120
AAGAGTTTGTAGGAAGATTTGGAATTAAGAAAATTGGAGA 1160
GTTGTACGGCTCAACAGAAGGAAACTCCAATATTGTTAAC 1200
```

FIG. 29A ceFATPb coding only DNA

```
           1210       1220       1230       1240
          |    |    |    |    |    |    |    |
GTGGATAACCATGTTGGAGCTTGTGGATTCATGCCAATTT 1240
ATCCCCATATTGGATCCCTCTACCCAGTTCGACTTATTAA 1280
GGTTGATAGAGCCACTGGAGAGCTTGAACGTGATAAGAAC 1320
GGACTCTGTGTGCCGTGTGTGCCTGGTGAAACTGGGGAAA 1360
TGGTTGGCGTTATCAAGGAGAAGATATTCTTCTAAAGTT 1400
           1410       1420       1430       1440
          |    |    |    |    |    |    |    |
CGAAGGATATGTCAGCGAAGGGGATACTGCAAAGAAAATC 1440
TACAGAGATGTGTTCAAGCATGGAGATAAGGTGTTTGCAA 1480
GTGGAGATATTCTTCATTGGGATGATCTTGGATACTTGTA 1520
CTTTGTGGACCGTTGTGGAGACACTTTCCGTTGGAAAGGG 1560
GAGAACGTGTCAACTACTGAAGTTGAGGGAATTCTTCAGC 1600
           1610       1620       1630       1640
          |    |    |    |    |    |    |    |
CTGTGATGGATGTGGAAGATGCAACTGTTTATGGAGTCAC 1640
TGTCGGTAAAATGGAGGGGCGTGCCGGAATGGCTGGTATT 1680
GTCGTCAAGGATGGAACGGATGTTGAGAAATTCATCGCCG 1720
ATATTACTTCTCGACTGACCGAAAATCTGGCGTCTTACGC 1760
AATCCCTGTTTTCATTCGGCTGTGCAAGGAAGTTGATCGA 1800
           1810       1820       1830       1840
          |    |    |    |    |    |    |    |
ACCGGAACCTTCAAACTCAAGAAGACTGATCTTCAAAAAC 1840
AAGGTTACGACCTGGTTGCTTGTAAAGGAGACCCAATTTA 1880
CTACTGGTCAGCTGCAGAAAAATCCTACAAACCACTGACT 1920
GACAAAATGCAACAGGATATTGACACTGGTGTTTATGATC 1960
GCATTTAA 1968
```

FIG. 29B ceFATPb coding only protein

```
          10        20        30        40
MREMPDSPKFALVTFVVYAVVLYNVNSVFWKFVFIGYVVF  40
RLLRTDFGRRALATLPRDFAGLKLLISVKSTIRGLFKKDR  80
PIHEIFLNQVKQHPNKVAIIEIESGRQLTYQELNALANQY 120
ANLYVSEGYKMGDVVALFMENSIDFFAIWLGLSKIGVVSA 160
FINSNLKLEPLAHSINVSKCKSCITNINLLPMFKAAREKN 200
         210       220       230       240
LISDEIHVFLAGTQVDGRHRSLQQDLHLFSEDEPPVIDGL 240
NFRSVLCYIYTSGTTGNPKPAVIKHFRYFWIAMGAGKAFG 280
INKSDVVYITMPMYHSAAGIMGIGSLIAFGSTAVIRKKFS 320
ASNFWKDCVKYNVTATQYIGEICRYLLAANPCPEEKQHNV 360
RLMWGNGLRGQIWKEFVGRFGIKKIGELYGSTEGNSNIVN 400
         410       420       430       440
VDNHVGACGFMPIYPHIGSLYPVRLIKVDRATGELERDKN 440
GLCVPCVPGETGEMVGVIKEKDILLKFEGYVSEGDTAKKI 480
YRDVFKHGDKVFASGDILHWDDLGYLYFVDRCGDTFRWKG 520
ENVSTTEVEGILQPVMDVEDATVYGVTGKMEGRAGMAGI  560
VVKDGTDVEKFIADITSRLTENLASYAIPVFIRLCKEVDR 600
         610       620       630       640
TGTFKLKKTDLQKQGYDLVACKGDPIYYWSAAEKSYKPLT 640
DKMQQDIDTGVYDRI. 656
```

FIG. 30 chFATP coding only DNA

```
         10        20        30        40
ATGGCGTGTATGCATCAGGCTCAGCTATACAATGATCTAG  40
AGGAATTGCTAACTGGTCCATCAGTACCCATCGTTGCTGG  80
AGCTGCTGGAGCTGCAGCTCTCACTGCCTACATTAACGCC 120
AAATACCACATAGCCCATGATCTCAAGACCCTCGGTGGTG 160
GATTGACACAATCGTCCGAAGCGATTGATTTCATAAACCG 200
        210       220       230       240
CCGCGTCGCACAAAAGCGCGTCCTCACGCACCACATCTTC 240
CAGGAGCAGGTCCAAAAACAATCAAATCATCCCTTTCTTA 280
TCTTTGAGGGCAAGACATGGTCTTACAAGGAGTTCTCTGA 320
GGCATACACGAGGGTCGCGAACTGGCTGATTGATGAGCTG 360
GACGTACAAGTAGGGGAGATGGTCGCAATTGATGGCGGAA 400
        410       420       430       440
ATAGTGCAGAGCACCTGATGCTTTGGCTTGCACTTGATGC 440
AATCGGTGCGGCTACGAGTTTTTTGAACTGGAACCTGACA 480
GGGGCAGGGTTAATTCATTGCATAAAGCTATGCGAATGTC 520
GATTCGTTATCGCAGACATCGATATTAAAGCGAACATTGA 560
ACCGTGCCGTGGCGAACTGGAGGAGACGGGCATCAACATT 600
        610       620       630       640
CACTACTATGACCCATCCTTCATCTCATCGCTACCGAATA 640
ACACGCCAATTCCCGACAGCCGCACTGAGAACATTGAATT 680
AGATTCAGTACGAGGACTGATATACACATCTGGAACCACT 720
GGTCTACCTAAAGGCGTGTTTATAAGCACTGGCCGCGAGC 760
TTAGGACTGACTGGTCGATTTCAAAGTATCTAAATCTCAA 800
        810       820       830       840
GCCCACGGATCGAATGTATACATGTATGCCGCTCTACCAT 840
GCCGCTGCACACAGCCTCTGTACAGCATCAGTTATTCATG 880
GTGGAGGTACCGTGGTATTGAGCAGGAAATTCTCACACAA 920
GAAGTTCTGGCCTGAAGTTGTGGCTTCGGAAGCAAATATC 960
ATTCAGTACGTTGGTGAATTAGGTCGATATCTCCTGAATG 1000
       1010      1020      1030      1040
GTCCAAAGAGTCCTTACGACAGGGCCCATAAAGTCCAGAT 1040
GGCGTGGGGCAATGGCATGCGTCCAGACGTGTGGGAAGCG 1080
TTTCGTGAACGCTTCAACATACCAATTATTCATGAGCTCT 1120
ATGCCGCAACCGATGGGCTCGGGTCAATGACCAATCGTAA 1160
CGCGGGCCCTTTTACAGCAAACTGTATTGCGCTGCGAGGG 1200
```

FIG. 31A chFATP coding only

```
         1210      1220      1230      1240
     |....|....|....|....|....|....|....|....|
     CTGATCTGGCACTGGAAATTTCGAAATCAGGAAGTGCTGG  1240
     TCAAGATGGATCTCGATACTGATGAGATCATGAGAGATCG  1280
     CAATGGGTTTGCGATACGATGCGCTGTCAATGAACCTGGA  1320
     CAGATGCTTTTCGGCTGACACCCGAAACTCTGGCTGGTG   1360
     CACCAAGCTACTACAACAACGAAACGGCCACACAGAGCAG  1400
         1410      1420      1430      1440
     |....|....|....|....|....|....|....|....|
     GCGGATTACAGATGTGTTTCAAAAGGGTGACCTGTGGTTC  1440
     AAGTCCGGTGACATGCTACGGCAAGACGCCGAAGGCCGCG  1480
     TCTACTTTGTCGATCGACTAGGCGATACGTTCCGCTGGAA  1520
     ATCCGAAAACGTTTCTACCAATGAAGTCGCGGACGTGATG  1560
     GGCACATTTCCTCAGATTGCTGAAACGAATGTATACGGTG  1600
         1610      1620      1630      1640
     |....|....|....|....|....|....|....|....|
     TCCTTGTGCCGGGTAACGATGGTCGAGTGCGCAGCCTCAA  1640
     TTGTCATGGCAGACGGCGTGACAGAGTCGACATTCGCTTC  1680
     GCTGCCCTTGCAAAGCACGCCCGAGATCGGTTACCGGGTT  1720
     ATGCTGTACCACTGTTTCTGAGGGTAACTCCAGCACTTGA  1760
     ATATACGGGCACATTAAAGATTCAGAAAGGACGCCTCAAG  1800
         1810      1820      1830      1840
     |....|....|....|....|....|....|....|....|
     CAGGAAGGTATAGACCCAGATAAGATTTCCGGCGAAGATA  1840
     AGTTATACTGGCTGCCGCCTGGTAGCGATATATATTTACC  1880
     ATTTGGAAAGATGGAGTGGCAGGGAATTGTAGATAAGCGT  1920
     ATACGGCTGTGA                              1932
```

FIG. 31B chFATP coding only protein

```
         10        20        30        40
         |         |         |         |
MACMHQAQLYNDLEELLTGPSVPIVAGAAGAAALTAYINA  40
KYHIAHDLKTLGGGLTQSSEAIDFINRRVAQKRVLTHHIF  80
QEQVQKQSNHPFLIFEGKTWSYKEFSEAYTRVANWLIDEL  120
DVQVGEMVAIDGGNSAEHLMLWLALDAIGAATSFLNWNLT  160
GAGLIHCIKLCECRFVIADIDIKANIEPCRGELEETGINI  200
        210       220       230       240
         |         |         |         |
HYYDPSFISSLPNNTPIPDSRTENIELDSVRGLIYTSGTT  240
GLPKGVFISTGRELRTDWSISKYLNLKPTDRMYTCMPLYH  280
AAAHSLCTASVIHGGGTVVLSRKFSHKKFWPEVVASEANI  320
IQYVGELGRYLLNGPKSPYDRAHKVQMAWGNGMRPDVWEA  360
FRERFNIPIIHELYAATDGLGSMTNRNAGPFTANCIALRG  400
        410       420       430       440
         |         |         |         |
LIWHWKFRNQEVLVKMDLDTDEIMRDRNGFAIRCAVNEPG  440
QMLFRLTPETLAGAPSYYNNETATQSRRITDVFQKGDLWF  480
KSGDMLRQDAEGRVYFVDRLGDTFRWKSENVSTNEVADVM  520
GTFPQIAETNVYGVLVPGNDGRVRSLNCHGRRRDRVDIRF  560
AALAKHARDRLPGYAVPLFLRVTPALEYTGTLKIQKGRLK  600
        610       620       630       640
         |         |         |         |
QEGIDPDKISGEDKLYWLPPGSDIYLPFGKMEWQGIVDKR  640
IRL  643
```

FIG. 32 mgFATP partial DNA

```
         10        20        30        40
         |         |         |         |
GCAAAGGCCGACGCGTGGCTGCGGACGGGTAACGTGATCA  40
GGGCGGACAACGAAGGGCGACTCTTCTTCCACGACCGGAT  80
CGGAGACACGTTCCGATGGAAGGGAGAGACNGTCAGCACA  120
CAAGAGGTCAGTTTGGTGCTCGGACGACACGACTCAATCA  160
AGGAGGCCAACGTGTACGGCGTGACGGTGCCGAACCACGA  200
        210       220       230       240
         |         |         |         |
CGGGCGGGCCGGCTGCGCTGCGCTCACGCTATCAGACGCT  240
CTGGCGACTGAAAAGAAGCTGGGCGATGAGCTGCTAAAGG  280
GATTGGCTACTCACTCGTCGACTTCGCTTCCCAAGTTTGC  320
GGTGCCGCAGTTCCTACGGGTGGTGCGCGGCGAGATGCAG  360
TCAACGGGCACCAACAAGCAACAGAAGCACGACCTGAGGG  400
        410       420       430       440
         |         |         |         |
TGCAGGGTGTAGAGCCGGGCAAGGTGGGCGTAGACGAGGT  440
GTACTGGTTGCGGGGAGGGACATATGTACCATTCGGAACA  480
GAGGATTGGGATGGGTTGAAGAAGGGTCTTGTGAAGTTGT  520
GA  522
```

FIG. 33 mgFATP partial protein

```
          10         20         30         40
         |          |          |          |
AKADAWLRTGNVIRADNEGRLFFHDRIGDTFRWKGETVST    40
QEVSLVLGRHDSIKEANVYGVTVPNHDGRAGCAALTLSDA    80
LATEKKLGDELLKGLATHSSTSLPKFAVPQFLRVVRGEMQ   120
STGTNKQQKHDLRVQGVEPGKVGVDEVYWLRGGTYVPFGT   160
EDWDGLKKGLVKL 173
```

FIG. 34 mtPATP coding only DNA

```
          10        20        30        40
          |         |         |         |
GTGTCCGATTACTACGGCGGCGCACACAACGGTCAGGC      40
TGATCGACCTGGCAACTCGGATGCCGCGAGTGTTGGCGGA    80
CACGCCGGTGATTGTGCGTGGGGCAATGACCGGGCTGCTG   120
GCCCGGCCGAATTCCAAGGCGTCGATCGGCACGGTGTTCC   160
AGGACCGGGCCGCTCGCTACGGTGACCGAGTCTTCCTGAA   200
         210       220       230       240
          |         |         |         |
ATTCGGCGATCAGCAGCTGACCTACCGCGACGCTAACGCC   240
ACCGCCAACCGGTACGCCGCGGTGTTGGCCGCCCGCGGCG   280
TCGGCCCCGGCGACGTCGTTGGCATCATGTTGCGTAACTC   320
ACCCAGCACAGTCTTGGCGATGCTGGCCACGGTCAAGTGC   360
GGCGCTATCGCCGGCATGCTCAACTACCACCAGCGCGGCG   400
         410       420       430       440
          |         |         |         |
AGGTGTTGGCGCACAGCCTGGGTCTGCTGGACGCGAAGGT   440
ACTGATCGCAGAGTCCGACTTGGTCAGCGCCGTCGCCGAA   480
TGCGGCGCCTCGCGCGGCCGGGTAGCGGGCGACGTGCTGA   520
CCGTCGAGGACGTGGAGCGATTCGCCACAACGGCGCCCGC   560
CACCAACCCGGCGTCGGCGTCGGCGGTGCAAGCCAAAGAC   600
         610       620       630       640
          |         |         |         |
ACCGCGTTCTACATCTTCACCTCGGGCACCACCGGATTTC   640
CCAAGGCCAGTGTCATGACGCATCATCGGTGGCTGCGGGC   680
GCTGGCCGTCTTCGGAGGGATGGGGCTGCGGCTGAAGGGT   720
TCCGACACGCTCTACAGCTGCCTGCCGCTGTACCACAACA   760
ACGCGTTAACGGTCGCGGTGTCGTCGGTGATCAATTCTGG   800
         810       820       830       840
          |         |         |         |
GGCGACCCTGGCGCTGGGTAAGTCGTTTTCGGCGTCGCGG   840
TTCTGGGATGAGGTGATTGCCAACCGGGCGACGGCGTTCG   880
TCTACATCGGCGAAATCTGCCGTTATCTGCTCAACCAGCC   920
GGCCAAGCCGACCGACCGTGCCCACCAGGTGCGGGTGATC   960
TGCGGTAACGGGCTGCGGCCGGAGATCTGGGATGAGTTCA  1000
        1010      1020      1030      1040
          |         |         |         |
CCACCCGCTTCGGGGTCGCGCGGGTGTGCGAGTTCTACGC  1040
CGCCAGCGAAGGCAACTCGGCCTTTATCAACATCTTCAAC  1080
GTGCCCAGGACCGCCGGGGTATCGCCGATGCCGCTTGCCT  1120
TTGTGGAATACGACCTGGACACCGGCGATCCGCTGCGGGA  1160
TGCGAGCGGGCGAGTGCGTCGGGTACCCGACGGTGAACCC  1200
```

FIG. 35A mtFATP coding only DNA

```
          1210      1220      1230      1240
    |....|....|....|....|....|....|....|....|
    GGCCTGTTGCTTAGCCGGGTCAACCGGCTGCAGCCGTTCG 1240
    ACGGCTACACCGACCCGGTTGCCAGCGAAAAGAAGTTGGT 1280
    GCGCAACGCTTTTCGAGATGGCGACTGTTGGTTCAACACC 1320
    GGTGACGTGATGAGCCCGCAGGGCATGGGCCATGCCGCCT 1360
    TCGTCGATCGGCTGGGCGACACCTTCCGCTGGAAGGGCGA 1400
          1410      1420      1430      1440
    |....|....|....|....|....|....|....|....|
    GAATGTCGCCACCACTCAGGTCGAAGCGGCACTGGCCTCC 1440
    GACCAGACCGTCGAGGAGTGCACGGTCTACGGCGTCCAGA 1480
    TTCCGCGCACCGGCGGGCGCGCCGGAATGGCCGCGATCAC 1520
    ACTGCGCGCTGGCGCCGAATTCGACGGCCAGGCGCTGGCC 1560
    CGAACGGTTTACGGTCACTTGCCCGGCTATGCACTTCCGC 1600
          1610      1620      1630      1640
    |....|....|....|....|....|....|....|....|
    TCTTTGTTCGGGTAGTGGGGTCGCTGGCGCACACCACGAC 1640
    GTTCAAGAGTCGCAAGGTGGAGTTGCGCAACCAGGCCTAT 1680
    GGCGCCGACATCGAGGATCCGCTGTACGTACTGGCCGGCC 1720
    CGGACGAAGGATATGTGCCGTACTACGCCGAATACCCTGA 1760
    GGAGGTTTCGCTCGGAAGGCGACCGCAGGGCTAG 1794
```

FIG. 35B mtFATP coding only protein

```
           10        20        30        40
    |....|....|....|....|....|....|....|....|
    MSDYYGGAHTTVRLIDLATRMPRVLADTPVIVRGAMTGLL 40
    ARPNSKASIGTVFQDRAARYGDRVFLKFGDQQLTYRDANA 80
    TANRYAAVLAARGVGPGDVVGIMLRNSPSTVLAMLATVKC 120
    GAIAGMLNYHQRGEVLAHSLGLLDAKVLIAESDLVSAVAE 160
    CGASRGRVAGDVLTVEDVERFATTAPATNPASASAVQAKD 200
          210       220       230       240
    |....|....|....|....|....|....|....|....|
    TAFYIFTSGTTGFPKASVMTHHRWLRALAVFGGMGLRLKG 240
    SDTLYSCLPLYHNNALTVAVSSVINSGATLALGKSFSASR 280
    FWDEVIANRATAFVYIGEICRYLLNQPAKPTDRAHQVRVI 320
    CGNGLRPEIWDEFTTRFGVARVCEFYAASEGNSAFINIFN 360
    VPRTAGVSPMPLAFVEYDLDTGDPLRDASGRVRRVPDGEP 400
          410       420       430       440
    |....|....|....|....|....|....|....|....|
    GLLLSRVNRLQPFDGYTDPVASEKKLVRNAFRDGDCWFNT 440
    GDVMSPQGMGHAAFVDRLGDTFRWKGENVATTQVEAALAS 480
    DQTVEECTVYGVQIPRTGGRAGMAAITLRAGAEFDGQALA 520
    RTVYGHLPGYALPLFVRVVGSLAHTTTFKSRKVELRNQAY 560
    GADIEDPLYVLAGPDEGYVPYYAEYPEEVSLGRRPQG. 598
```

FIG. 36

SEQUENCE LISTING

<160> NUMBER OF SEQ ID NOS: 37

<210> SEQ ID NO 1
<211> LENGTH: 340
<212> TYPE: PRT
<213> ORGANISM: Mus musculus

<400> SEQUENCE: 1

```
Phe Ile Phe Thr Ser Gly Thr Thr Gly Leu Pro Lys Pro Ala Ile Leu
 1               5                  10                  15

Ser His Glu Arg Val Ile Gln Val Ser Asn Val Leu Ser Phe Cys Gly
            20                  25                  30

Cys Arg Ala Asp Asp Val Val Tyr Asp Val Leu Pro Leu Tyr His Thr
        35                  40                  45

Ile Gly Leu Val Leu Gly Phe Leu Gly Cys Leu Gln Val Gly Ala Thr
    50                  55                  60

Cys Val Leu Ala Pro Lys Phe Ser Ala Ser Arg Phe Trp Ala Glu Cys
65                  70                  75                  80

Arg Gln His Gly Val Thr Val Ile Gln Tyr Ile Gly Glu Ile Cys Arg
                85                  90                  95

Tyr Leu Leu Arg Gln Pro Val Arg Asp Val Glu Gln Arg His Arg Val
            100                 105                 110

Arg Leu Ala Val Gly Asn Gly Leu Arg Pro Ala Ile Trp Glu Glu Phe
        115                 120                 125

Thr Gln Arg Phe Gly Val Pro Gln Ile Gly Glu Phe Tyr Gly Ala Thr
    130                 135                 140

Glu Cys Asn Cys Ser Ile Ala Asn Met Asp Gly Lys Val Gly Ser Cys
145                 150                 155                 160

Gly Phe Asn Ser Arg Ile Leu Thr His Val Tyr Pro Ile Arg Leu Val
                165                 170                 175

Lys Val Asn Glu Asp Thr Met Glu Pro Leu Arg Asp Ser Glu Gly Leu
            180                 185                 190

Cys Ile Pro Cys Gln Pro Gly Glu Pro Gly Leu Leu Val Gly Gln Ile
        195                 200                 205

Asn Gln Gln Asp Pro Leu Arg Arg Phe Asp Gly Tyr Val Ser Asp Ser
    210                 215                 220

Ala Thr Asn Lys Lys Ile Ala His Ser Val Phe Arg Lys Gly Asp Ser
225                 230                 235                 240

Ala Tyr Leu Ser Gly Asp Val Leu Val Met Asp Glu Leu Gly Tyr Met
                245                 250                 255

Tyr Phe Arg Asp Arg Ser Gly Asp Thr Phe Arg Trp Arg Gly Glu Asn
            260                 265                 270

Val Ser Thr Thr Glu Val Glu Ala Val Leu Ser Arg Leu Leu Gly Gln
        275                 280                 285

Thr Asp Val Ala Val Tyr Gly Val Ala Val Pro Gly Val Glu Gly Lys
    290                 295                 300

Ala Gly Met Ala Ala Ile Ala Asp Pro His Ser Gln Leu Asp Pro Asn
305                 310                 315                 320

Ser Met Tyr Gln Glu Leu Gln Lys Val Leu Ala Ser Tyr Ala Arg Pro
                325                 330                 335

Ile Phe Leu Arg
            340
```

```
<210> SEQ ID NO 2
<211> LENGTH: 339
<212> TYPE: PRT
<213> ORGANISM: Mus musculus

<400> SEQUENCE: 2

Tyr Ile Tyr Thr Ser Gly Thr Thr Gly Asn Pro Lys Pro Ala Val Ile
 1               5                  10                  15

Lys His Phe Arg Tyr Phe Trp Ile Ala Met Gly Ala Gly Lys Ala Phe
                20                  25                  30

Gly Ile Asn Lys Ser Asp Val Val Tyr Ile Thr Met Pro Met Tyr His
            35                  40                  45

Ser Ala Ala Gly Ile Met Gly Ile Gly Ser Leu Ile Ala Phe Gly Ser
50                  55                  60

Thr Ala Val Ile Arg Lys Lys Phe Ser Ala Ser Asn Phe Trp Lys Asp
65                  70                  75                  80

Cys Val Lys Tyr Asn Val Thr Ala Thr Leu Tyr Val Gly Glu Ile Leu
                85                  90                  95

Arg Tyr Leu Cys Asn Val Pro Glu Gln Pro Glu Asp Lys Ile His Thr
            100                 105                 110

Val Arg Leu Ala Met Gly Thr Gly Leu Arg Ala Asn Val Trp Lys Asn
        115                 120                 125

Phe Gln Gln Arg Phe Gly Pro Ile Arg Ile Trp Glu Phe Tyr Gly Ser
    130                 135                 140

Thr Glu Gly Asn Val Gly Leu Met Asn Tyr Val Gly His Cys Gly Ala
145                 150                 155                 160

Val Gly Arg Thr Ser Cys Ile Leu Arg Met Leu Thr Pro Phe Glu Leu
                165                 170                 175

Val Gln Phe Asp Ile Glu Thr Ala Glu Pro Leu Arg Asp Lys Gln Gly
            180                 185                 190

Phe Cys Ile Pro Val Glu Pro Gly Lys Pro Gly Leu Leu Leu Thr Lys
        195                 200                 205

Val Arg Lys Asn Gln Pro Phe Leu Gly Tyr Arg Gly Ser Gln Ala Glu
    210                 215                 220

Ser Asn Arg Lys Leu Val Ala Asn Val Arg Arg Val Gly Asp Leu Tyr
225                 230                 235                 240

Phe Asn Thr Gly Asp Val Leu Thr Leu Asp Gln Glu Gly Phe Tyr
                245                 250                 255

Phe Gln Asp Arg Leu Gly Asp Thr Phe Arg Trp Lys Gly Glu Asn Val
            260                 265                 270

Ser Thr Gly Glu Val Glu Cys Val Leu Ser Ser Leu Asp Phe Leu Glu
        275                 280                 285

Glu Val Asn Val Tyr Gly Val Pro Val Pro Gly Cys Glu Gly Lys Val
    290                 295                 300

Gly Met Ala Ala Val Lys Leu Ala Pro Gly Lys Thr Phe Asp Gly Lys
305                 310                 315                 320

Lys Tyr Gln His Val Arg Ser Trp Leu Pro Ala Tyr Ala Thr Pro His
                325                 330                 335

Phe Ile Arg

<210> SEQ ID NO 3
<211> LENGTH: 345
<212> TYPE: PRT
<213> ORGANISM: Caenorhabditis elegans

<400> SEQUENCE: 3
```

Ile Tyr Thr Ser Gly Thr Thr Gly Leu Pro Lys Ser Ala Ile Met Ser
 1               5                  10                  15

Trp Arg Lys Ser Ser Val Gly Cys Gln Val Phe Gly His Val Leu His
            20                  25                  30

Met Thr Asn Glu Ser Thr Val Phe Thr Ala Met Pro Leu Phe His Ser
        35                  40                  45

Thr Ala Ala Leu Leu Gly Ala Cys Ala Ile Leu Ser His Gly Gly Cys
    50                  55                  60

Leu Ala Leu Ser His Lys Phe Ser Ala Ser Thr Phe Trp Lys Gln Val
65                  70                  75                  80

Tyr Leu Thr Gly Ala Thr His Ile Gln Tyr Ile Gly Glu Ile Cys Arg
                85                  90                  95

Tyr Leu Leu Ala Ala Asn Pro Cys Pro Glu Glu Lys Gln His Asn Val
            100                 105                 110

Arg Leu Met Trp Gly Asn Gly Leu Arg Gly Gln Ile Trp Lys Glu Phe
        115                 120                 125

Val Gly Arg Phe Gly Ile Lys Lys Ile Gly Glu Leu Tyr Gly Ser Thr
    130                 135                 140

Glu Gly Asn Ser Asn Ile Val Asn Val Asp Asn His Val Gly Ala Cys
145                 150                 155                 160

Gly Phe Met Pro Ile Tyr Pro His Ile Gly Ser Leu Tyr Pro Val Arg
                165                 170                 175

Leu Ile Lys Val Asp Arg Ala Thr Gly Glu Leu Glu Arg Asp Lys Asn
            180                 185                 190

Gly Leu Cys Val Pro Cys Val Pro Gly Glu Thr Gly Glu Met Val Gly
        195                 200                 205

Val Ile Lys Glu Lys Asp Ile Leu Leu Lys Phe Glu Gly Tyr Val Ser
    210                 215                 220

Glu Gly Asp Thr Ala Lys Lys Ile Tyr Arg Asp Val Phe Lys His Gly
225                 230                 235                 240

Asp Lys Val Phe Ala Ser Gly Asp Ile Leu His Trp Asp Asp Leu Gly
                245                 250                 255

Tyr Leu Tyr Phe Val Asp Arg Cys Gly Asp Thr Phe Arg Trp Lys Gly
            260                 265                 270

Glu Asn Val Ser Thr Thr Glu Val Glu Gly Ile Leu Gln Pro Val Met
        275                 280                 285

Asp Val Glu Asp Ala Thr Val Tyr Gly Val Thr Val Gly Lys Met Glu
    290                 295                 300

Gly Arg Ala Gly Met Ala Gly Ile Val Val Lys Asp Gly Thr Asp Val
305                 310                 315                 320

Glu Lys Phe Ile Ala Asp Ile Thr Ser Arg Leu Thr Glu Asn Leu Ala
                325                 330                 335

Ser Tyr Ala Ile Pro Val Phe Ile Arg
            340                 345

<210> SEQ ID NO 4
<211> LENGTH: 356
<212> TYPE: PRT
<213> ORGANISM: Saccharomyces cerevisiae

<400> SEQUENCE: 4

Tyr Ile Tyr Thr Ser Gly Thr Thr Gly Leu Pro Lys Ala Ala Ile Val
 1               5                  10                  15

Val His Ser Arg Tyr Tyr Arg Ile Ala Ala Phe Gly His His Ser Tyr

```
                20                  25                  30
Ser Met Arg Ala Ala Asp Val Leu Tyr Asp Cys Leu Pro Leu Tyr His
         35                  40                  45

Ser Ala Gly Asn Ile Met Gly Val Gly Gln Cys Val Ile Tyr Gly Leu
     50                  55                  60

Thr Val Leu Arg Lys Lys Phe Ser Ala Ser Arg Phe Trp Asp Asp
 65                  70                  75                  80

Cys Val Lys Tyr Asn Cys Thr Val Val Gln Tyr Val Gly Glu Val Cys
                 85                  90                  95

Arg Tyr Leu Leu His Thr Pro Ile Ser Lys Tyr Glu Lys Met His Lys
             100                 105                 110

Val Lys Val Ala Tyr Gly Asn Gly Leu Arg Pro Asp Ile Trp Gln Asp
         115                 120                 125

Phe Arg Lys Arg Phe Asn Ile Glu Val Ile Gly Glu Phe Tyr Ala Ala
     130                 135                 140

Thr Glu Ala Pro Phe Ala Thr Thr Thr Phe Gln Lys Gly Asp Phe Gly
145                 150                 155                 160

Ile Gly Ala Cys Arg Asn Tyr Gly Thr Ile Ile Gln Trp Phe Leu Ser
                 165                 170                 175

Phe Gln Gln Thr Leu Val Arg Met Asp Pro Asn Asp Asp Ser Val Ile
             180                 185                 190

Tyr Arg Asn Ser Lys Gly Phe Cys Glu Val Ala Pro Val Gly Glu Pro
         195                 200                 205

Gly Glu Met Leu Met Arg Ile Phe Phe Pro Lys Lys Pro Glu Thr Ser
     210                 215                 220

Phe Gln Gly Tyr Leu Gly Asn Ala Lys Glu Thr Lys Ser Lys Val Val
225                 230                 235                 240

Arg Asp Val Phe Arg Arg Gly Asp Ala Trp Tyr Arg Cys Gly Asp Leu
                 245                 250                 255

Leu Lys Ala Asp Glu Tyr Gly Leu Trp Tyr Phe Leu Asp Arg Met Gly
             260                 265                 270

Asp Thr Phe Arg Trp Lys Ser Glu Asn Val Ser Thr Thr Glu Val Glu
         275                 280                 285

Asp Gln Leu Thr Ala Ser Asn Lys Glu Gln Tyr Ala Gln Val Leu Val
     290                 295                 300

Val Gly Ile Lys Val Pro Lys Tyr Glu Gly Arg Ala Gly Phe Ala Val
305                 310                 315                 320

Ile Lys Leu Thr Asp Asn Ser Leu Asp Ile Thr Ala Lys Thr Lys Leu
                 325                 330                 335

Leu Asn Asp Ser Leu Ser Arg Leu Asn Leu Pro Ser Tyr Ala Met Pro
             340                 345                 350

Leu Phe Val Lys
        355

<210> SEQ ID NO 5
<211> LENGTH: 334
<212> TYPE: PRT
<213> ORGANISM: Mycobacterium tuberculosis

<400> SEQUENCE: 5

Tyr Ile Phe Thr Ser Gly Thr Thr Gly Phe Pro Lys Ala Ser Val Met
 1               5                  10                  15

Thr His His Arg Trp Leu Arg Ala Leu Ala Val Phe Gly Gly Met Gly
             20                  25                  30
```

```
Leu Arg Leu Lys Gly Ser Asp Thr Leu Tyr Ser Cys Leu Pro Leu Tyr
            35                  40                  45

His Asn Asn Ala Leu Thr Val Ala Val Ser Ser Val Ile Asn Ser Gly
 50                  55                  60

Ala Thr Leu Ala Leu Gly Lys Ser Phe Ser Ala Ser Arg Phe Trp Asp
 65                  70                  75                  80

Glu Val Ile Ala Asn Arg Ala Thr Ala Phe Val Tyr Ile Gly Glu Ile
                 85                  90                  95

Cys Arg Tyr Leu Leu Asn Gln Pro Ala Lys Pro Thr Asp Arg Ala His
                100                 105                 110

Gln Val Arg Val Ile Cys Gly Asn Gly Leu Arg Pro Glu Ile Trp Asp
            115                 120                 125

Glu Phe Thr Thr Arg Phe Gly Val Ala Arg Val Cys Glu Phe Tyr Ala
    130                 135                 140

Ala Ser Glu Gly Asn Ser Ala Phe Ile Asn Ile Phe Asn Val Pro Arg
145                 150                 155                 160

Thr Ala Gly Val Ser Pro Met Pro Leu Ala Phe Val Glu Tyr Asp Leu
                165                 170                 175

Asp Thr Gly Asp Pro Leu Arg Asp Ala Ser Gly Arg Val Arg Arg Val
            180                 185                 190

Pro Asp Gly Glu Pro Gly Leu Leu Leu Ser Arg Val Asn Arg Leu Gln
        195                 200                 205

Pro Phe Asp Gly Tyr Thr Asp Pro Val Ala Ser Glu Lys Lys Leu Val
    210                 215                 220

Arg Asn Ala Phe Arg Asp Gly Asp Cys Trp Phe Asn Thr Gly Asp Val
225                 230                 235                 240

Met Ser Pro Gln Gly Met Gly His Ala Ala Phe Val Asp Arg Leu Gly
                245                 250                 255

Asp Thr Phe Arg Trp Lys Gly Glu Asn Val Ala Thr Thr Gln Val Glu
            260                 265                 270

Ala Ala Leu Ala Ser Asp Gln Thr Val Glu Glu Cys Thr Val Tyr Gly
        275                 280                 285

Val Gln Ile Pro Arg Thr Gly Gly Arg Ala Gly Met Ala Ala Ile Thr
    290                 295                 300

Leu Arg Ala Gly Ala Glu Phe Asp Gly Gln Ala Leu Ala Arg Thr Val
305                 310                 315                 320

Tyr Gly His Leu Pro Gly Tyr Ala Leu Pro Leu Phe Val Arg
                325                 330

<210> SEQ ID NO 6
<211> LENGTH: 2087
<212> TYPE: DNA
<213> ORGANISM: Mus musculus

<400> SEQUENCE: 6
acgactcact atagggagag agctatgacg tcgcatgcac gcgtaagctt gggcccctcg    60
agggatcctc tagagcggcc gccgaccccg aaagctctga gagcgggtgc agtctggcct   120
ggcgtctcgc gtacctggcc cgggagcagc cgacacacac cttcctcatc cacggcgcgc   180
agcgctttag ctacgcggag gctgagcgcg agagcaaccg gattgctcgc gcctttctgc   240
gcgcacgggg ctggaccggg ggccgccgag gctcgggcag gggcagcact gaggaaggcg   300
cacgcgtggc gcctccggct ggagatgcgc ctgctagagg acgaccgcg ccccctctgg   360 caccccgggc gaccgtggcg ctgctcctcc cagcgggccc ggatttcctt tggatttggt   420
```

-continued

```
tcggactggc caaagctggc ctgcgcacgg cctttgtgcc caccgcttta cgccgaggac    480
ccctgctgca ctgcctccgc agctgcggtg cgagtgcgct cgtgctggcc acagagttcc    540
tggagtccct ggagccggac ctgccggcct tgagagccat ggggctccac ctatgggcga    600
cgggccctga aactaatgta gctggaatca gcaatttgct atcggaagca gcagaccaag    660
tggatgagcc agtgccgggg tacctctctg cccccagaa cataatggac acctgcctgt     720
acatcttcac ctctggcact actggcctgc ccaaggctgc tcgaatcagt catctgaagg    780
ttctacagtg ccagggattc taccatctgt gtggagtcca ccaggaggac gtgatctacc    840
tcgcactccc actgtaccac atgtctggct cccttctggg cattgtgggc tgcttgggca    900
ttggggccac cgtggtgctg aaacccaagt tctcagctag ccagttctgg gacgattgcc    960
agaaacacag ggtgacagtg ttccagtaca ttggggagtt gtgccgatac ctcgtcaacc   1020
agcccccgag caaggcagag tttgaccata aggtgcgctt ggcagtgggc agtgggttgc   1080
gcccagacac ctgggagcgt ttcctgcggc gatttggacc tctgcagata ctggagacgt   1140
atggcatgac agagggcaac gtagctacgt tcaattacac aggacggcag ggtgcagtgg   1200
ggcgagcttc ctggctttac aagcacatct tccccttctc cttgattcga tacgatgtca   1260
tgacagggga gcctattcgg aatgcccagg ggcactgcat gaccacatct ccaggtgagc   1320
caggcctact ggtggcccca gtgagccagc agtccccctt cctgggctat gctggggctc   1380
cggagctggc caaggacaag ctgctgaagg atgtcttctg gtctggggac gttttcttca   1440
atactgggga cctcttggtc tgtgatgagc aaggctttct tcacttccac gatcgtactg   1500
gagacaccat caggtggaag ggagagaatg tggccacaac tgaagtggct gaggtcttgg   1560
agaccctgga cttccttcag gaggtgaaca tctatggagt cacggtgcca gggcacgaag   1620
gcagggcagg catggcggcc ttggctctgc ggcccccgca ggctctgaac ctggtgcagc   1680
tctacagcca tgtttctgag aacttgccac cgtatgcccg acctcggttt ctcaggctcc   1740
aggaatcttt ggccactact gagaccttca acagcagaa ggttaggatg ccaatgagg     1800 gctttgaccc cagtgtactg tctgacccac tctatgttct ggaccaagat atagggggct   1860
acctgcccct cacacctgcc cggtacagtg ccctcctgtc tggagacctt cgaatctgaa   1920
accttccact tgagggaggg gctcggaggg tacaggccac catggctgca ccagggaggg   1980
ttttcgggta tcttttgtat atggagtcat tattttgtaa taaacagctg gagcttaaaa   2040
aaaaaaaaaa aaaaaaaaaa aaaaaaaaaa aaaaaaaaaa aaaaaaa                 2087
```

<210> SEQ ID NO 7
<211> LENGTH: 613
<212> TYPE: PRT
<213> ORGANISM: Mus musculus

<400> SEQUENCE: 7

```
Ala Ala Asp Pro Glu Ser Ser Glu Ser Gly Cys Ser Leu Ala Trp Arg
 1               5                  10                  15

Leu Ala Tyr Leu Ala Arg Glu Gln Pro Thr His Thr Phe Leu Ile His
             20                  25                  30

Gly Ala Gln Arg Phe Ser Tyr Ala Glu Ala Glu Arg Glu Ser Asn Arg
         35                  40                  45

Ile Ala Arg Ala Phe Leu Arg Ala Arg Gly Trp Thr Gly Gly Arg Arg
     50                  55                  60

Gly Ser Gly Arg Gly Ser Thr Glu Glu Gly Ala Arg Val Ala Pro Pro
 65                  70                  75                  80
```

-continued

```
Ala Gly Asp Ala Ala Ala Arg Gly Thr Thr Ala Pro Pro Leu Ala Pro
                85                  90                  95
Gly Ala Thr Val Ala Leu Leu Leu Pro Ala Gly Pro Asp Phe Leu Trp
            100                 105                 110
Ile Trp Phe Gly Leu Ala Lys Ala Gly Leu Arg Thr Ala Phe Val Pro
        115                 120                 125
Thr Ala Leu Arg Arg Gly Pro Leu Leu His Cys Leu Arg Ser Cys Gly
    130                 135                 140
Ala Ser Ala Leu Val Leu Ala Thr Glu Phe Leu Glu Ser Leu Glu Pro
145                 150                 155                 160
Asp Leu Pro Ala Leu Arg Ala Met Gly Leu His Leu Trp Ala Thr Gly
                165                 170                 175
Pro Glu Thr Asn Val Ala Gly Ile Ser Asn Leu Leu Ser Glu Ala Ala
            180                 185                 190
Asp Gln Val Asp Glu Pro Val Pro Gly Tyr Leu Ser Ala Pro Gln Asn
        195                 200                 205
Ile Met Asp Thr Cys Leu Tyr Ile Phe Thr Ser Gly Thr Thr Gly Leu
    210                 215                 220
Pro Lys Ala Ala Arg Ile Ser His Leu Lys Val Leu Gln Cys Gln Gly
225                 230                 235                 240
Phe Tyr His Leu Cys Gly Val His Gln Glu Asp Val Ile Tyr Leu Ala
                245                 250                 255
Leu Pro Leu Tyr His Met Ser Gly Ser Leu Leu Gly Ile Val Gly Cys
            260                 265                 270
Leu Gly Ile Gly Ala Thr Val Val Leu Lys Pro Lys Phe Ser Ala Ser
        275                 280                 285
Gln Phe Trp Asp Asp Cys Gln Lys His Arg Val Thr Val Phe Gln Tyr
    290                 295                 300
Ile Gly Glu Leu Cys Arg Tyr Leu Val Asn Gln Pro Pro Ser Lys Ala
305                 310                 315                 320
Glu Phe Asp His Lys Val Arg Leu Ala Val Gly Ser Gly Leu Arg Pro
                325                 330                 335
Asp Thr Trp Glu Arg Phe Leu Arg Arg Phe Gly Pro Leu Gln Ile Leu
            340                 345                 350
Glu Thr Tyr Gly Met Thr Glu Gly Asn Val Ala Thr Phe Asn Tyr Thr
        355                 360                 365
Gly Arg Gln Gly Ala Val Gly Arg Ala Ser Trp Leu Tyr Lys His Ile
    370                 375                 380
Phe Pro Phe Ser Leu Ile Arg Tyr Asp Val Met Thr Gly Glu Pro Ile
385                 390                 395                 400
Arg Asn Ala Gln Gly His Cys Met Thr Thr Ser Pro Gly Glu Pro Gly
                405                 410                 415
Leu Leu Val Ala Pro Val Ser Gln Gln Ser Pro Phe Leu Gly Tyr Ala
            420                 425                 430
Gly Ala Pro Glu Leu Ala Lys Asp Lys Leu Leu Lys Asp Val Phe Trp
        435                 440                 445
Ser Gly Asp Val Phe Phe Asn Thr Gly Asp Leu Leu Val Cys Asp Glu
    450                 455                 460
Gln Gly Phe Leu His Phe His Asp Arg Thr Gly Asp Thr Ile Arg Trp
465                 470                 475                 480
Lys Gly Glu Asn Val Ala Thr Thr Glu Val Ala Glu Val Leu Glu Thr
                485                 490                 495
Leu Asp Phe Leu Gln Glu Val Asn Ile Tyr Gly Val Thr Val Pro Gly
```

His Glu Gly Arg Ala Gly Met Ala Ala Leu Ala Leu Arg Pro Pro Gln
    515                 520                 525

Ala Leu Asn Leu Val Gln Leu Tyr Ser His Val Ser Glu Asn Leu Pro
    530                 535                 540

Pro Tyr Ala Arg Pro Arg Phe Leu Arg Leu Gln Glu Ser Leu Ala Thr
545                 550                 555                 560

Thr Glu Thr Phe Lys Gln Gln Lys Val Arg Met Ala Asn Glu Gly Phe
                565                 570                 575

Asp Pro Ser Val Leu Ser Asp Pro Leu Tyr Val Leu Asp Gln Asp Ile
            580                 585                 590

Gly Ala Tyr Leu Pro Leu Thr Pro Ala Arg Tyr Ser Ala Leu Leu Ser
            595                 600                 605

Gly Asp Leu Arg Ile
            610

<210> SEQ ID NO 8
<211> LENGTH: 2301
<212> TYPE: DNA
<213> ORGANISM: Mus musculus

<400> SEQUENCE: 8

| | | | | | |
|---|---|---|---|---|---|
| cccacgcgtc | cgcccacgcg | tccggcatgg | ccaagctggg | cgtggaggcg | gctctcatca | 60 |
| acaccaacct | taggcgggat | gccctgcgcc | actgtcttga | cacctcaaag | gcacgagctc | 120 |
| tcatctttgg | cagtgagatg | gcctcagcta | tctgtgagat | ccatgctagc | ctggagccca | 180 |
| cactcagcct | cttctgctct | ggatcctggg | agcccagcac | agtgcccgtc | agcacagagc | 240 |
| atctggaccc | tcttctggaa | gatgccccga | agcacctgcc | cagtcaccca | gacaagggtt | 300 |
| ttacagataa | gctcttctac | atctacacat | cgggcaccac | ggggctaccc | aaagctgcca | 360 |
| ttgtggtgca | cagcaggtat | tatcgtatgg | cttccctggt | gtactatgga | ttccgcatgc | 420 |
| ggcctgatga | cattgtctat | gactgcctcc | ccctctacca | ctcaagcagg | aaacatcgtg | 480 |
| gggattggca | gtgcttactc | cacggcatga | ctgtggtgat | ccggaagaag | ttctcagcct | 540 |
| cccggttctg | ggatgattgt | atcaagtaca | actgcacagt | ggtacagtac | attggcgagc | 600 |
| tctgccgcta | cctcctgaac | cagccacccc | gtgaggctga | gtctcggcac | aaggtgcgca | 660 |
| tggcactggg | caacggtctc | cggcagtcca | tctggaccga | cttctccagc | cgtttccaca | 720 |
| tccccccaggt | ggctgagttc | tatggggcca | ctgaatgcaa | ctgtagcctg | ggcaactttg | 780 |
| acagccgggt | gggggcctgt | ggcttcaata | gccgcatcct | gtcctttgtg | taccctatcc | 840 |
| gtttggtacg | tgtcaatgag | gataccatgg | aactgatccg | ggacccgat | ggagtctgca | 900 |
| ttccctgtca | accaggtcag | ccaggccagc | tggtgggtcg | catcatccag | caggaccctc | 960 |
| tgcgccgttt | cgacgggtac | ctcaaccagg | gtgccaacaa | caagaagatt | gctaatgatg | 1020 |
| tcttcaagaa | gggggaccaa | gcctacctca | ctggtgacgt | cctggtgatg | gatgagctgg | 1080 |
| gttacctgta | cttccgagat | cgcactgggg | acacgttccg | ctggaaaggg | gagaatgtat | 1140 |
| ctaccactga | ggtggagggc | acactcagcc | gcctgcttca | tatggcagat | gtggcagttt | 1200 |
| atggtgttga | ggtgccagga | actgaaggcc | gagcaggaat | ggctgccgtt | gcaagtccca | 1260 |
| tcagcaactg | tgacctggag | agctttgcac | agaccttgaa | aaaggagctg | cctctgtatg | 1320 |
| cccgccccat | cttcctgcgc | ttcttgcctg | agctgcacaa | gacagggacc | ttcaagttcc | 1380 |
| agaagacaga | gttgcggaag | gagggctttg | acccatctgt | tgtgaaagac | ccgctgttct | 1440 |

-continued

| | |
|---|---|
| atctggatgc tcggaagggc tgctacgttg cactggacca ggaggcctat acccgcatcc | 1500 |
| aggcaggcga ggagaagctg tgatttcccc ctacatccct ctgagggcca agatgctg | 1560 |
| gattcagagc cctagcgtcc accccagagg gtcctgggca atgccagacc aaagctagca | 1620 |
| gggcccgcac ctccgcccct aggtgctgat ctcccctctc ccaaactgcc aagtgactca | 1680 |
| ctgccgcttc cccgaccctc cagaggcttt ctgtgaaagt ctcatccaag ctgtgtcttc | 1740 |
| tggtccaggc gtggcccctg ccccagggt ttctgatagg ctcctttagg atggtatctt | 1800 |
| gggtccagcg ggccagggtg tgggagagga gtcactaaga tccctccaat cagaagggag | 1860 |
| cttacaaagg aaccaaggca aagcctgtag actcaggaag ctaagtggcc agagactata | 1920 |
| gtggccagtc atcccatgtc cacagaggat cttggtccag agctgccaaa gtgtcacctc | 1980 |
| tccctgcctg cacctctggg gaaaagagga cagcatgtgg ccactgggca cctgtctcaa | 2040 |
| gaagtcagga tcacacactc agtccttgtt tctccaggtt cccttgttct tgtctcgggg | 2100 |
| agggagggac gagtgtcctg tctgtccttc ctgcctgtct gtgagtctgt gttgcttctc | 2160 |
| catctgtcct agcctgagtg tgggtggaac aggcatgagg agagtgtggc tcagggccaa | 2220 |
| ataaactctg ccttgactcc tcttaaaaaa aaaaaaaaaa aaaaaaaaaa aaaaaaaaaa | 2280 |
| aaaaaaaaaa aaaaaaaaaa a | 2301 |

<210> SEQ ID NO 9
<211> LENGTH: 506
<212> TYPE: PRT
<213> ORGANISM: Mus musculus

<400> SEQUENCE: 9

```
His Ala Ser Ala His Ala Ser Gly Met Ala Lys Leu Gly Val Glu Ala
 1               5                  10                  15

Ala Leu Ile Asn Thr Asn Leu Arg Arg Asp Ala Leu Arg His Cys Leu
            20                  25                  30

Asp Thr Ser Lys Ala Arg Ala Leu Ile Phe Gly Ser Glu Met Ala Ser
        35                  40                  45

Ala Ile Cys Glu Ile His Ala Ser Leu Glu Pro Thr Leu Ser Leu Phe
    50                  55                  60

Cys Ser Gly Ser Trp Glu Pro Ser Thr Val Pro Val Ser Thr Glu His
65                  70                  75                  80

Leu Asp Pro Leu Leu Glu Asp Ala Pro Lys His Leu Pro Ser His Pro
                85                  90                  95

Asp Lys Gly Phe Thr Asp Lys Leu Phe Tyr Ile Tyr Thr Ser Gly Thr
            100                 105                 110

Thr Gly Leu Pro Lys Ala Ala Ile Val Val His Ser Arg Tyr Tyr Arg
        115                 120                 125

Met Ala Ser Leu Val Tyr Tyr Gly Phe Arg Met Arg Pro Asp Asp Ile
    130                 135                 140

Val Tyr Asp Cys Leu Pro Leu Tyr His Ser Ser Arg Lys His Arg Gly
145                 150                 155                 160

Asp Trp Gln Cys Leu His Gly Met Thr Val Ile Arg Lys Lys
                165                 170                 175

Phe Ser Ala Ser Arg Phe Trp Asp Asp Cys Ile Lys Tyr Asn Cys Thr
            180                 185                 190

Val Val Gln Tyr Ile Gly Glu Leu Cys Arg Tyr Leu Leu Asn Gln Pro
        195                 200                 205

Pro Arg Glu Ala Glu Ser Arg His Lys Val Arg Met Ala Leu Gly Asn
    210                 215                 220
```

-continued

```
Gly Leu Arg Gln Ser Ile Trp Thr Asp Phe Ser Ser Arg Phe His Ile
225                 230                 235                 240

Pro Gln Val Ala Glu Phe Tyr Gly Ala Thr Glu Cys Asn Cys Ser Leu
            245                 250                 255

Gly Asn Phe Asp Ser Arg Val Gly Ala Cys Gly Phe Asn Ser Arg Ile
        260                 265                 270

Leu Ser Phe Val Tyr Pro Ile Arg Leu Val Arg Val Asn Glu Asp Thr
    275                 280                 285

Met Glu Leu Ile Arg Gly Pro Asp Gly Val Cys Ile Pro Cys Gln Pro
290                 295                 300

Gly Gln Pro Gly Gln Leu Val Gly Arg Ile Ile Gln Gln Asp Pro Leu
305                 310                 315                 320

Arg Arg Phe Asp Gly Tyr Leu Asn Gln Gly Ala Asn Asn Lys Lys Ile
            325                 330                 335

Ala Asn Asp Val Phe Lys Lys Gly Asp Gln Ala Tyr Leu Thr Gly Asp
        340                 345                 350

Val Leu Val Met Asp Glu Leu Gly Tyr Leu Tyr Phe Arg Asp Arg Thr
    355                 360                 365

Gly Asp Thr Phe Arg Trp Lys Gly Glu Asn Val Ser Thr Thr Glu Val
370                 375                 380

Glu Gly Thr Leu Ser Arg Leu Leu His Met Ala Asp Val Ala Val Tyr
385                 390                 395                 400

Gly Val Glu Val Pro Gly Thr Gly Arg Ala Gly Met Ala Ala Val
            405                 410                 415

Ala Ser Pro Ile Ser Asn Cys Asp Leu Glu Ser Phe Ala Gln Thr Leu
        420                 425                 430

Lys Lys Glu Leu Pro Leu Tyr Ala Arg Pro Ile Phe Leu Arg Phe Leu
    435                 440                 445

Pro Glu Leu His Lys Thr Gly Thr Phe Lys Phe Gln Lys Thr Glu Leu
    450                 455                 460

Arg Lys Glu Gly Phe Asp Pro Ser Val Val Lys Asp Pro Leu Phe Tyr
465                 470                 475                 480

Leu Asp Ala Arg Lys Gly Cys Tyr Val Ala Leu Asp Gln Glu Ala Tyr
            485                 490                 495

Thr Arg Ile Gln Ala Gly Glu Glu Lys Leu
            500                 505
```

<210> SEQ ID NO 10
<211> LENGTH: 2277
<212> TYPE: DNA
<213> ORGANISM: Mus musculus

<400> SEQUENCE: 10

```
cactcatcag agctaagaga gactacacgc tctcatctac ttcagaaaga gccaatgcca      60
tgggtatttg aagaaactaa accttactgc tgttgctgct tctgctggtt ggcctggggc     120
agcccccatg ccagcagct atggctctgg ccctgcgttg gttcctggga gaccccacat      180
gccttgtgct gcttggcttg gcattgctgg gcagaccctg atcagctcc tggatgcccc      240
actggctgag cctggtagga gcagctctta ccttattcct attgcctcta cagccacccc     300
cagggctacg ctggctgcat aaagatgtgg cttcacctt caagatgctt ttctatggcc     360
taaagttcag gcgacgcctt aacaaacatc ctccagagac ctttgtggat gctttagagc     420
ggcaagcact ggcatggcct gaccgggtgg ccttggtgtg tactgggtct gagggctcct    480
```

-continued

```
caatcacaaa tagccagctg gatgccaggt cctgtcaggc agcatgggtc ctgaaagcaa      540
agctgaagga tgccgtaatc cagaacacaa gagatgctgc tgctatctta gttctcccgt      600
ccaagaccat ttctgctttg agtgtgtttc tggggttggc caagttgggc tgccctgtgg      660
cctggatcaa tccacacagc cgagggatgc ccttgctaca ctctgtacgg agctctgggg      720
ccagtgtgct gattgtggat ccagacctcc aggagaacct ggaagaagtc cttcccaagc      780
tgctagctga gaacattcac tgcttctacc ttggccacag ctcacccacc ccgggagtag      840
aggctctggg agcttccctg gatgctgcac cttctgaccc agtacctgcc agccttcgag      900
ctacgattaa gtggaaatct cctgccatat tcatctttac ttcagggacc actggactcc      960
caaagccagc catcttatca catgagcggg tcatacaagt gagcaacgtg ctgtccttct     1020
gtggatgcag agctgatgat gtggtctatg acgtcctacc tctgtaccat acgatagggc     1080
ttgtccttgg attccttggc tgcttacaag ttggagccac ctgtgtcctg gcccccaagt     1140
tctctgcctc ccgattctgg gctgagtgcc ggcagcatgg cgtaacagtg atcttgtatg     1200
tgggtgaaat cctgcggtac ttgtgtaacg tccctgagca accagaagac aagatacata     1260
cagtgcgctt ggccatggga actggacttc gggcaaatgt gtggaaaaac ttccagcaac     1320
gctttggtcc cattcggatc tgggaattct acggatccac agagggcaat gtgggcttaa     1380
tgaactatgt gggccactgc ggggctgtgg aaggaccag ctgcatcctt cgaatgctga     1440 ctcccttga gcttgtacag ttcgacatag acagcaga gcctctgagg acaaacagg     1500 gttttttgcat tcctgtggag ccaggaaagc caggacttct tttgaccaag gttcgaaaga     1560 accaacccctt cctgggctac cgtggttccc aggccgagtc caatcggaaa cttgttgcga     1620
atgtacgacg cgtaggagac ctgtacttca acactgggga cgtgctgacc ttggaccagg     1680
aaggcttctt ctactttcaa gaccgccttg gtgacacctt ccggtggaag ggcgaaaacg     1740
tatctactgg agaggtggag tgtgttttgt ctagcctaga cttcctagag gaagtcaatg     1800
tctatggtgt gcctgtgcca gggtgtgagg gtaaggttgg catggctgct gtgaaactgg     1860
ctcctgggaa gactttgat gggcagaagc tataccagca tgtccgctcc tggctccctg     1920
cctatgccac acctcatttc atccgtatcc aggattccct ggagatcaca aacacctaca     1980
agctggtaaa gtcacggctg gtgcgtgagg gttttgatgt ggggatcatt gctgacccccc     2040 tctacatact ggacaacaag gcccagacct tccggagtct gatgccagat gtgtaccagg     2100
ctgtgtgtga aggaacctgg aatctctgac cacctagcca actggaaggc aatccaaaag     2160
tgtagagatt gacactagtc agcttcacaa agttgtccgg gttccagatg cccatggccc     2220
agtagtactt agagaataaa cttgaatgtg tatacaaaaa aaaaaaaaaa aaaaaaa       2277
```

<210> SEQ ID NO 11
<211> LENGTH: 662
<212> TYPE: PRT
<213> ORGANISM: Mus musculus

<400> SEQUENCE: 11

```
Met Ala Leu Ala Leu Arg Trp Phe Leu Gly Asp Pro Thr Cys Leu Val
 1               5                   10                  15

Leu Leu Gly Leu Ala Leu Leu Gly Arg Pro Trp Ile Ser Ser Trp Met
            20                  25                  30

Pro His Trp Leu Ser Leu Val Gly Ala Ala Leu Thr Leu Phe Leu Leu
        35                  40                  45

Pro Leu Gln Pro Pro Gly Leu Arg Trp Leu His Lys Asp Val Ala
    50                  55                  60
```

-continued

```
Phe Thr Phe Lys Met Leu Phe Tyr Gly Leu Lys Phe Arg Arg Arg Leu
 65                  70                  75                  80

Asn Lys His Pro Pro Glu Thr Phe Val Asp Ala Leu Glu Arg Gln Ala
                 85                  90                  95

Leu Ala Trp Pro Asp Arg Val Ala Leu Val Cys Thr Gly Ser Glu Gly
                100                 105                 110

Ser Ser Ile Thr Asn Ser Gln Leu Asp Ala Arg Ser Cys Gln Ala Ala
                115                 120                 125

Trp Val Leu Lys Ala Lys Leu Lys Asp Ala Val Ile Gln Asn Thr Arg
130                 135                 140

Asp Ala Ala Ile Leu Val Leu Pro Ser Lys Thr Ile Ser Ala Leu
145                 150                 155                 160

Ser Val Phe Leu Gly Leu Ala Lys Leu Gly Cys Pro Val Ala Trp Ile
                165                 170                 175

Asn Pro His Ser Arg Gly Met Pro Leu Leu His Ser Val Arg Ser Ser
                180                 185                 190

Gly Ala Ser Val Leu Ile Val Asp Pro Asp Leu Gln Glu Asn Leu Glu
                195                 200                 205

Glu Val Leu Pro Lys Leu Leu Ala Glu Asn Ile His Cys Phe Tyr Leu
                210                 215                 220

Gly His Ser Ser Pro Thr Pro Gly Val Glu Ala Leu Gly Ala Ser Leu
225                 230                 235                 240

Asp Ala Ala Pro Ser Asp Pro Val Pro Ala Ser Leu Arg Ala Thr Ile
                245                 250                 255

Lys Trp Lys Ser Pro Ala Ile Phe Ile Phe Thr Ser Gly Thr Thr Gly
                260                 265                 270

Leu Pro Lys Pro Ala Ile Leu Ser His Glu Arg Val Ile Gln Val Ser
                275                 280                 285

Asn Val Leu Ser Phe Cys Gly Cys Arg Ala Asp Asp Val Val Tyr Asp
                290                 295                 300

Val Leu Pro Leu Tyr His Thr Ile Gly Leu Val Leu Gly Phe Leu Gly
305                 310                 315                 320

Cys Leu Gln Val Gly Ala Thr Cys Val Leu Ala Pro Lys Phe Ser Ala
                325                 330                 335

Ser Arg Phe Trp Ala Glu Cys Arg Gln His Gly Val Thr Val Ile Leu
                340                 345                 350

Tyr Val Gly Glu Ile Leu Arg Tyr Leu Cys Asn Val Pro Glu Gln Pro
                355                 360                 365

Glu Asp Lys Ile His Thr Val Arg Leu Ala Met Gly Thr Gly Leu Arg
                370                 375                 380

Ala Asn Val Trp Lys Asn Phe Gln Gln Arg Phe Gly Pro Ile Arg Ile
385                 390                 395                 400

Trp Glu Phe Tyr Gly Ser Thr Glu Gly Asn Val Gly Leu Met Asn Tyr
                405                 410                 415

Val Gly His Cys Gly Ala Val Gly Arg Thr Ser Cys Ile Leu Arg Met
                420                 425                 430

Leu Thr Pro Phe Glu Leu Val Gln Phe Asp Ile Glu Thr Ala Glu Pro
                435                 440                 445

Leu Arg Asp Lys Gln Gly Phe Cys Ile Pro Val Glu Pro Gly Lys Pro
                450                 455                 460

Gly Leu Leu Leu Thr Lys Val Arg Lys Asn Gln Pro Phe Leu Gly Tyr
465                 470                 475                 480
```

-continued

```
Arg Gly Ser Gln Ala Glu Ser Asn Arg Lys Leu Val Ala Asn Val Arg
                485                 490                 495
Arg Val Gly Asp Leu Tyr Phe Asn Thr Gly Asp Val Leu Thr Leu Asp
            500                 505                 510
Gln Glu Gly Phe Phe Tyr Phe Gln Asp Arg Leu Gly Asp Thr Phe Arg
        515                 520                 525
Trp Lys Gly Glu Asn Val Ser Thr Gly Glu Val Glu Cys Val Leu Ser
    530                 535                 540
Ser Leu Asp Phe Leu Glu Glu Val Asn Val Tyr Gly Val Pro Val Pro
545                 550                 555                 560
Gly Cys Glu Gly Lys Val Gly Met Ala Ala Val Lys Leu Ala Pro Gly
                565                 570                 575
Lys Thr Phe Asp Gly Gln Lys Leu Tyr Gln His Val Arg Ser Trp Leu
            580                 585                 590
Pro Ala Tyr Ala Thr Pro His Phe Ile Arg Ile Gln Asp Ser Leu Glu
        595                 600                 605
Ile Thr Asn Thr Tyr Lys Leu Val Lys Ser Arg Leu Val Arg Glu Gly
    610                 615                 620
Phe Asp Val Gly Ile Ile Ala Asp Pro Leu Tyr Ile Leu Asp Asn Lys
625                 630                 635                 640
Ala Gln Thr Phe Arg Ser Leu Met Pro Asp Val Tyr Gln Ala Val Cys
                645                 650                 655
Glu Gly Thr Trp Asn Leu
            660
```

<210> SEQ ID NO 12
<211> LENGTH: 1622
<212> TYPE: DNA
<213> ORGANISM: Homo sapiens
<220> FEATURE:
<221> NAME/KEY: misc_feature
<222> LOCATION: (1)...(1621)
<223> OTHER INFORMATION: n = A,T,C or G

<400> SEQUENCE: 12

```
atgggattga ctctttcctg gacaaagtgg atgaagtatc aactgaacct atcccagagt      60
catggaggtc tgaagtcact ttttccactc ctgcccttata catttatact tctgaaccca    120
caggtcttcc aaaagcagcc atgatcactc atcagcgcat atggtatgga actggcctca    180
cttttgtaag cggattgaag gcagatgatg tcatctatat cactctgccc ttttaccaca    240
gtgctgcact actgattggc attcacggat gtattgtggc tggtgctact cttgccttgc    300
ggactaaatt ttcagccagc cagttttggg atgactgcag aaaatacaac gtcactgtca    360
ttcagtatat cggtgaactg cttcggtatt tatgcaactc accacagaaa ccaaatgacc    420
gtgatcataa agtgagactg gcactgggaa atggcttacg aggagatgtg tggagacaat    480
ttgtcaagag atttggggac atatgcatct atgagttcta tgctgccact gaaggcaata    540
ttggatttat gaattatgcg agaaaagttg gtgctgttgg aagagtaaac tacctacaga    600
aaaaaatcat aacttatgac ctgattaaat atgatgtgga gaaagatgaa cctgtccgtg    660
atgaaaatgg atattgcgtc agagttccca aggtgaagt tggacttctg gtttgcaaaa    720
tcacacaact tacaccattt aatggctatg ctggagcaaa ggctcagaca gagaagaaaa    780
aactgagaga tgtctttaag aaaggagacc tctatttcaa cagtggagat ctcttaatgg    840
ttgaccatga aaatttcatc tatttccacg acagagttgg agatacattc cggtggaaag    900
gggaaaatgt ggccaccact gaagttgctg atatagttgg actggttgat ttttttccaa    960
```

-continued

```
ggaagtaaaa tgtttatggg agtgcatggg ccaagatnat ggaggttcga attggcatgg    1020
cnttccnttc aaaatggaaa gaaaaccatg gaatttgatg gaaagaaatt ttttcagnac    1080
attgctgata accnacctag ttatgcaagg ccccggtttt ntaagaanac aggacaccat    1140
tgagatcact ggaatttta aacaccgcaa aatgacctt ggtggaggag ggctttaacc      1200
cngctgtcat caaagatgcc ttgtatttc ttggatgaca cagcaaaaat gtatgtgcct     1260
atgactgagg acatntataa tgccataagt gntaaaaccc tgaaattntg aatattccca    1320
ggaggataat tcaacattc cagaaagaaa ctgaatggac agccacttga tataatccaa     1380
ctttaatttg attgaagatt gtgaggaaat tttgtaggaa atttgcatac ccgtaaaggg    1440 agacttttt aaataacagt tgagtctttg caagtaaaaa gatttagaga ttattatttt     1500
tcagtgtgca cctactgttt gtatttgcaa actgagcttg ttggagggaa ggcattattt    1560
tttaaaatac ttagtaaatt aaagaacacc aacatgtgaa aaaaaaaaa aaaaaaaaa      1620 aa                                                                   1622
```

<210> SEQ ID NO 13
<211> LENGTH: 286
<212> TYPE: PRT
<213> ORGANISM: Homo sapiens

<400> SEQUENCE: 13

```
Tyr Ile Tyr Thr Ser Gly Thr Thr Gly Leu Pro Lys Ala Ala Met Ile
 1               5                  10                  15

Thr His Gln Arg Ile Trp Tyr Gly Thr Gly Leu Thr Phe Val Ser Gly
            20                  25                  30

Leu Lys Ala Asp Asp Val Ile Tyr Ile Thr Leu Pro Phe Tyr His Ser
        35                  40                  45

Ala Ala Leu Leu Ile Gly Ile His Gly Cys Ile Val Ala Gly Ala Thr
    50                  55                  60

Leu Ala Leu Arg Thr Lys Phe Ser Ala Ser Gln Phe Trp Asp Asp Cys
65                  70                  75                  80

Arg Lys Tyr Asn Val Thr Val Ile Gln Tyr Ile Gly Glu Leu Leu Arg
                85                  90                  95

Tyr Leu Cys Asn Ser Pro Gln Lys Pro Asn Asp Arg Asp His Lys Val
            100                 105                 110

Arg Leu Ala Leu Gly Asn Gly Leu Arg Gly Asp Val Trp Arg Gln Phe
        115                 120                 125

Val Lys Arg Phe Gly Asp Ile Cys Ile Tyr Glu Phe Tyr Ala Ala Thr
    130                 135                 140

Glu Gly Asn Ile Gly Phe Met Asn Tyr Ala Arg Lys Val Gly Ala Val
145                 150                 155                 160

Gly Arg Val Asn Tyr Leu Gln Lys Ile Ile Thr Tyr Asp Leu Ile
                165                 170                 175

Lys Tyr Asp Val Glu Lys Asp Glu Pro Val Arg Asp Glu Asn Gly Tyr
            180                 185                 190

Cys Val Arg Val Pro Lys Gly Glu Val Gly Leu Leu Val Cys Lys Ile
        195                 200                 205

Thr Gln Leu Thr Pro Phe Asn Gly Tyr Ala Gly Ala Lys Ala Gln Thr
    210                 215                 220

Glu Lys Lys Lys Leu Arg Asp Val Phe Lys Lys Gly Asp Leu Tyr Phe
225                 230                 235                 240

Asn Ser Gly Asp Leu Leu Met Val Asp His Glu Asn Phe Ile Tyr Phe
```

```
                      245                 250                 255
His Asp Arg Val Gly Asp Thr Phe Arg Trp Lys Gly Glu Asn Val Ala
                260                 265                 270
Thr Thr Glu Val Ala Asp Ile Val Gly Leu Val Asp Phe Phe
        275                 280                 285

<210> SEQ ID NO 14
<211> LENGTH: 753
<212> TYPE: DNA
<213> ORGANISM: Homo sapiens

<400> SEQUENCE: 14
caattcggga cccccagggg cactgtatgg ccacatctcc aggtgagcca ggggaagttg      60
ctaaaggatg tcttccggcc tggggatgtt ttcttcaaca ctggggacct gctggtctgc    120
gatgaccaag gttttctccg cttccatgat cgtactggag acaccttcag gtggaaaggg    180
gagaatgtgg ccacaaccga ggtggcagag gtcttcgagg ccctagattt tcttcaggag    240
gtgaacgtct atggagtcac tgtgccaggg catgaaggca gggctggaat ggcagcccta    300
gttctgcgtc cccccacgc tttggacctt atgcagctct acacccacgt gtctgagaac    360
ttgccacctt atgcccggcc ccgattcctc aggctccagg agtctttggc caccacagag    420
accttcaaac agcagaaagt tcggatggca atgagggct cgaccccag cccctgtct    480
gacccactgt acgttctgga ccaggctgta ggtgcctacc tgcccctcac aactgcccgg    540
tacagcgccc tcctggcagg aaaccttcga atctgagaac ttccacacct gaggcacctg    600
agagaggaac tctgtggggt ggggccgtt gcaggtgtac tgggctgtca gggatctttt    660
ctataccaga actgcggtca ctattttgta ataaatgtgg ctggagctga tccagctgtc    720
tctgacctac aaaaaaaaaa aaaaaaaaaa aaa                                   753

<210> SEQ ID NO 15
<211> LENGTH: 191
<212> TYPE: PRT
<213> ORGANISM: Homo sapiens

<400> SEQUENCE: 15

Gln Phe Gly Thr Pro Arg Gly Thr Val Trp Pro His Leu Gln Val Ser
 1               5                  10                  15

Gln Gly Lys Leu Leu Lys Asp Val Phe Arg Pro Gly Asp Val Phe Phe
                20                  25                  30

Asn Thr Gly Asp Leu Leu Val Cys Asp Asp Gln Gly Phe Leu Arg Phe
            35                  40                  45

His Asp Arg Thr Gly Asp Thr Phe Arg Trp Lys Gly Glu Asn Val Ala
        50                  55                  60

Thr Thr Glu Val Ala Glu Val Phe Glu Ala Leu Asp Phe Leu Gln Glu
65                  70                  75                  80

Val Asn Val Tyr Gly Val Thr Val Pro Gly His Glu Gly Arg Ala Gly
                85                  90                  95

Met Ala Ala Leu Val Leu Arg Pro Pro His Ala Leu Asp Leu Met Gln
            100                 105                 110

Leu Tyr Thr His Val Ser Glu Asn Leu Pro Pro Tyr Ala Arg Pro Arg
        115                 120                 125

Phe Leu Arg Leu Gln Glu Ser Leu Ala Thr Thr Glu Thr Phe Lys Gln
    130                 135                 140

Gln Lys Val Arg Met Ala Asn Glu Gly Phe Asp Pro Ser Thr Leu Ser
145                 150                 155                 160
```

```
Asp Pro Leu Tyr Val Leu Asp Gln Ala Val Gly Ala Tyr Leu Pro Leu
            165                 170                 175

Thr Thr Ala Arg Tyr Ser Ala Leu Leu Ala Gly Asn Leu Arg Ile
        180                 185                 190

<210> SEQ ID NO 16
<211> LENGTH: 734
<212> TYPE: DNA
<213> ORGANISM: Homo sapiens
<220> FEATURE:
<221> NAME/KEY: misc_feature
<222> LOCATION: (1)...(733)
<223> OTHER INFORMATION: n = A,T,C or G

<400> SEQUENCE: 16
tcaagtacaa ctgcacgatt gtcatancat tggtgaactg tgccgntacc tcctgaacca      60
gccaccgcgg gaggcagaaa accagcacca ggttcgcatg cactaggca atggcctccg      120
gcagtccatc tggaccaact tttccagccg cttccacata ccccaggtgg ctgagtttyta    180
cggggccaca gagtgcaact gtagcctggg caacttcgac agccaggtgg gggcctgtgg     240
tttcaatagc cgcatcctgt ccttcgtgta ccccatccgg ttggtacgtg tcaacgagga    300
caccatggag ctgatccggg ggcccgacgg cgtctgcatt ccctgccagc caggtgagcc    360
gggccagctg gtgggccgca tcatccagaa agaccccctg cgccgcttcg atggctacct    420
caaccagggc gccaacaaca agaagattgc caaggatgtc ttcaagaagg gggaccaggc    480
ctaccttact ggtgatgtgc tggtgatgga cgagctgggc tacctgtact ccgagaccg    540
cactggggac acgttccgct ggaaaggtga aacgtgtcc accaccgagg tggaaggcac    600
actcagccgc ctgctggaca tggctgacgt ggccgtgtat ggtgtcgagg tgccaggaac    660
cgagggccgg gccggaatgg ctgctgtggc cagccccact ggcaactgtg acctgggagc    720
gctttgctca ggtc                                                       734

<210> SEQ ID NO 17
<211> LENGTH: 213
<212> TYPE: PRT
<213> ORGANISM: Homo sapiens

<400> SEQUENCE: 17

Ile Gly Glu Leu Cys Arg Tyr Leu Leu Asn Gln Pro Arg Glu Ala
 1               5                  10                  15

Glu Asn Gln His Gln Val Arg Met Ala Leu Gly Asn Gly Leu Arg Gln
                20                  25                  30

Ser Ile Trp Thr Asn Phe Ser Arg Phe His Ile Pro Gln Val Ala
            35                  40                  45

Glu Phe Tyr Gly Ala Thr Glu Cys Asn Cys Ser Leu Gly Asn Phe Asp
     50                  55                  60

Ser Gln Val Gly Ala Cys Gly Phe Asn Ser Arg Ile Leu Ser Phe Val
 65                  70                  75                  80

Tyr Pro Ile Arg Leu Val Arg Val Asn Glu Asp Thr Met Glu Leu Ile
                85                  90                  95

Arg Gly Pro Asp Gly Val Cys Ile Pro Cys Gln Pro Gly Glu Pro Gly
                100                 105                 110

Gln Leu Val Gly Arg Ile Ile Gln Lys Asp Pro Leu Arg Arg Phe Asp
            115                 120                 125

Gly Tyr Leu Asn Gln Gly Ala Asn Asn Lys Lys Ile Ala Lys Asp Val
        130                 135                 140
```

```
Phe Lys Lys Gly Asp Gln Ala Tyr Leu Thr Gly Asp Val Leu Val Met
145                 150                 155                 160

Asp Glu Leu Gly Tyr Leu Tyr Phe Arg Asp Arg Thr Gly Asp Thr Phe
            165                 170                 175

Arg Trp Lys Gly Glu Asn Val Ser Thr Thr Glu Val Glu Gly Thr Leu
            180                 185                 190

Ser Arg Leu Leu Asp Met Ala Asp Val Ala Val Tyr Gly Val Glu Val
            195                 200                 205

Pro Gly Thr Glu Gly
    210
```

<210> SEQ ID NO 18
<211> LENGTH: 1278
<212> TYPE: DNA
<213> ORGANISM: Homo sapiens
<220> FEATURE:
<221> NAME/KEY: misc_feature
<222> LOCATION: (1)...(1278)
<223> OTHER INFORMATION: n = A,T,C or G

<400> SEQUENCE: 18

```
cntgcctctt gtaccacgtg atgggacttt gtcgttggga tcctcggctg cttagatctc    60
ggagccacct gtgttctggc ccccaagttc tctacttcct gcttctggga tgactgtcgg   120
cagcatggcg tgacagtgat cctgtatgtg ggcgagctcc tgcgntactt gtgtaacatt   180
ccccagcaac cagaggaccg gacacataca gtccgcctgg caatgggcaa tggactacgg   240
gctgatgtgt ggggagacct tccagcagcg tttcggtcct atttcggatc tngggaagtc   300
ttacgggcty ccacagaagg gcaacatggg gctttagttc aactattgtt ggggcgctg    360
cggggscctg grggcaaaga tggagcttgc ctcctccgaa tgctgtcccc ctttgagctg   420
gtgcagttcg acatggaggc ggcggagcct gtgaggggaca tcagggcttt ctgcatccct   480
gtagggctag gggagccggg gctgctgttg accaaggtgg taagccagca accctttcgtg  540
ggctaccgcg gccccccgaga gctgtcggaa cggaagctgg tgcgcaacgt gcggcaatcg  600
ggcgacgttt actacaacac cggggacgta ctggccatgg accgcgaagg cttcctctac  660
ttccgcgacc gactcgggga caccttccga tggaagggcg agaacgtgtc cacgcacgag  720
gtggagggcg tgttgtcgca ggtggacttc ttgcaacagg ttaacgtgta tggcgtgtgc  780
gtgccaggtt gtgagggtaa ggtgggcatg gctgctgtgg cattagcccc cggccagact  840
ttcgacgggg agaagttgta ccagcacgtt cgcgcttggc tccctgccta cgctaccccc  900
catttcatcc gcatccagga cgccatggag gtcaccagca cgttcaaact gatgaagacc  960
cggttggtgc gtgagggctt caatgtgggg atcgtggttg accctctgtt tgtactggac 1020
aaccgggccc agtccttccg gcccctgacg gcagaaatgt accaggctgt gtgtgaggga 1080
acctggaggc tctgatcacc tggccaaccc actggggtag ggatcaaagc cagccacccc 1140
cacccccaaca cactcggtgt ccctttcatc ctgggcctgt gtgaatccca gcctggccat 1200
accctcaacc tcagtgggct ggaaatgaca gtgggccctg tagcagtggc agaataaact 1260
cagmtgygtt cacagaaa                                               1278
```

<210> SEQ ID NO 19
<211> LENGTH: 199
<212> TYPE: PRT
<213> ORGANISM: Homo sapiens

<400> SEQUENCE: 19

Glu Gly Gln His Gly Ala Leu Val Gln Leu Leu Leu Gly Ala Leu Arg
1               5                   10                  15

Gly Pro Gly Gly Lys Asp Gly Ala Cys Leu Leu Arg Met Leu Ser Pro
            20                  25                  30

Phe Glu Leu Val Gln Phe Asp Met Glu Ala Ala Glu Pro Val Arg Asp
        35                  40                  45

Asn Gln Gly Phe Cys Ile Pro Val Gly Leu Gly Glu Pro Gly Leu Leu
    50                  55                  60

Leu Thr Lys Val Val Ser Gln Gln Pro Phe Val Gly Tyr Arg Gly Pro
65              70                  75                  80

Arg Glu Leu Ser Glu Arg Lys Leu Val Arg Asn Val Arg Gln Ser Gly
                85                  90                  95

Asp Val Tyr Tyr Asn Thr Gly Asp Val Leu Ala Met Asp Arg Glu Gly
            100                 105                 110

Phe Leu Tyr Phe Arg Asp Arg Leu Gly Asp Thr Phe Arg Trp Lys Gly
            115                 120                 125

Glu Asn Val Ser Thr His Glu Val Glu Gly Val Leu Ser Gln Val Asp
    130                 135                 140

Phe Leu Gln Gln Val Asn Val Tyr Gly Val Cys Val Pro Gly Cys Glu
145                 150                 155                 160

Gly Lys Val Gly Met Ala Ala Val Ala Leu Ala Pro Gly Gln Thr Phe
                165                 170                 175

Asp Gly Glu Lys Leu Tyr Gln His Val Arg Ala Trp Leu Pro Ala Tyr
            180                 185                 190

Ala Thr Pro His Phe Ile Arg
            195

<210> SEQ ID NO 20
<211> LENGTH: 1361
<212> TYPE: DNA
<213> ORGANISM: Homo sapiens

<400> SEQUENCE: 20
cgcttgtgtg ttaaagaaga aattttcagc aagccagttt tggagtgact gcaagaagta      60
tgatgtgact gtgtttcagt atattggaga actttgtcgc tacctttgca aacaatctaa     120
gagagaagga gaaaggatca taaggtgcg tttggcaatt ggaaatggca tacggagtga     180
tgtatggaga gaatttttag acagatttgg aaatataaag gtgtgtgaac tttatgcagc     240
taccgaatca agcatatctt tcatgaacta cactgggaga attggagcaa ttgggagaac     300
aaatttgttt tacaaacttc tttccacttt tgacttaata aagtatgact ttcagaaaga     360
tgaacccatg agaaatgagc agggttgggt attcatgaga aaaggagac ctggacttct      420 catttctcga gtgaatgcaa aaaatcccctt ctttggctat gctgggcctt ataagcacac     480
aaaagacaaa ttgctttgtg atgtttttaa gaagggagat gtttacctta atactggaga     540
cttaatagtc caggatcagg acaatttcct ttatttttgg gaccgtactg agacactttt     600
cagatggaaa ggagaaaatg tcgcaaccac tgaggttgct gatgttattg gaatgttgga     660
tttcatacag gaagcaaacg tctatggtgt ggctatatca ggttatgaag gaagagcagg     720
aatggcttct attatttaa aaccaaatac atctttagat ttggaaaaag tttatgaaca     780
agttgtaaca tttctaccag cttatgcttt tccacgattt ttaagaattc aggaaaaaat     840
ggaagcaaca ggaacattca aactattgaa gcatcagttg gtggaagatg gatttaatcc     900
actgaaaatt tctgaaccac tttacttcat ggataacttg aaaaagtctt atgttctact     960

-continued

```
gaccagggaa ctttatgatc aaataatgtt aggggaaata aaactttaag atttttatat    1020
ctagaacttt catatgcttt cttaggaaga gtgagagggg ggtatatgat tctttatgaa    1080
atggggaaag ggagctaaca ttaattatgc atgtactata tttccttaat atgagagata    1140
attttttaat tgcataagaa ttttaattc ttttaattga tataaacaga gttgattatc      1200
ctttttatct atttggagat tcagtgcata actaagtatt ttccttaata ctaaagattt    1260
taaataataa atagtggcta gcggtttgga caatcactaa aaatgtactt tctaataagt    1320
aaaatttcta attttgaata aaagattaaa ttttactgaa a                        1361
```

<210> SEQ ID NO 21
<211> LENGTH: 335
<212> TYPE: PRT
<213> ORGANISM: Homo sapiens

<400> SEQUENCE: 21

```
Ala Cys Val Leu Lys Lys Lys Phe Ser Ala Ser Gln Phe Trp Ser Asp
 1               5                  10                  15

Cys Lys Lys Tyr Asp Val Thr Val Phe Gln Tyr Ile Gly Glu Leu Cys
            20                  25                  30

Arg Tyr Leu Cys Lys Gln Ser Lys Arg Glu Gly Glu Lys Asp His Lys
        35                  40                  45

Val Arg Leu Ala Ile Gly Asn Gly Ile Arg Ser Asp Val Trp Arg Glu
    50                  55                  60

Phe Leu Asp Arg Phe Gly Asn Ile Lys Val Cys Glu Leu Tyr Ala Ala
65                  70                  75                  80

Thr Glu Ser Ser Ile Ser Phe Met Asn Tyr Thr Gly Arg Ile Gly Ala
                85                  90                  95

Ile Gly Arg Thr Asn Leu Phe Tyr Lys Leu Leu Ser Thr Phe Asp Leu
            100                 105                 110

Ile Lys Tyr Asp Phe Gln Lys Asp Glu Pro Met Arg Asn Glu Gln Gly
        115                 120                 125

Trp Val Phe Met Arg Lys Arg Pro Gly Leu Leu Ile Ser Arg Val
    130                 135                 140

Asn Ala Lys Asn Pro Phe Phe Gly Tyr Ala Gly Pro Tyr Lys His Thr
145                 150                 155                 160

Lys Asp Lys Leu Leu Cys Asp Val Phe Lys Lys Gly Asp Val Tyr Leu
                165                 170                 175

Asn Thr Gly Asp Leu Ile Val Gln Asp Gln Asp Asn Phe Leu Tyr Phe
            180                 185                 190

Trp Asp Arg Thr Gly Asp Thr Phe Arg Trp Lys Gly Glu Asn Val Ala
        195                 200                 205

Thr Thr Glu Val Ala Asp Val Ile Gly Met Leu Asp Phe Ile Gln Glu
    210                 215                 220

Ala Asn Val Tyr Gly Val Ala Ile Ser Gly Tyr Glu Gly Arg Ala Gly
225                 230                 235                 240

Met Ala Ser Ile Ile Leu Lys Pro Asn Thr Ser Leu Asp Leu Glu Lys
                245                 250                 255

Val Tyr Glu Gln Val Val Thr Phe Leu Pro Ala Tyr Ala Cys Pro Arg
            260                 265                 270

Phe Leu Arg Ile Gln Glu Lys Met Glu Ala Thr Gly Thr Phe Lys Leu
        275                 280                 285

Leu Lys His Gln Leu Val Glu Asp Gly Phe Asn Pro Leu Lys Ile Ser
    290                 295                 300
```

-continued

```
Glu Pro Leu Tyr Phe Met Asp Asn Leu Lys Lys Ser Tyr Val Leu Leu
305                 310                 315                 320

Thr Arg Glu Leu Tyr Asp Gln Ile Met Leu Gly Glu Ile Lys Leu
                325                 330                 335
```

<210> SEQ ID NO 22
<211> LENGTH: 2007
<212> TYPE: DNA
<213> ORGANISM: Mycobacterium tuberculosis

<400> SEQUENCE: 22

```
tagtcgataa cgtcaaggac gctctgcggg cctgcgcacc ttcctgaggt tggtcgacaa      60
ccaattcgac atttcgcaaa cgaatcgagg cttacgtgt ccgattacta cggcggcgca     120
cacacaacgg tcaggctgat cgacctggca actcggatgc cgcgagtgtt ggcggacacg     180
ccggtgattg tgcgtggggc aatgaccggg ctgctggccc ggccgaattc caaggcgtcg     240
atcggcacgg tgttccagga ccgggccgct cgctacggtg accgagtctt cctgaaattc     300
ggcgatcagc agctgaccta ccgcgacgct aacgccaccg ccaaccggta cgccgcggtg     360
ttggccgccc gcggcgtcgg ccccggcgac gtcgttggca tcatgttgcg taactcaccc     420
agcacagtct tggcgatgct ggccacggtc aagtgcggcg ctatcgccgg catgctcaac     480
taccaccagc gcggcgaggt gttggcgcac agcctgggtc tgctggacgc gaaggtactg     540
atcgcagagt ccgacttggt cagcgccgtc gccgaatgcg gcgcctcgcg cggccgggta     600
gcgggcgacg tgctgaccgt cgaggacgtg gagcgattcg ccacaacggc gcccgccacc     660
aacccggcgt cggcgtcggc ggtgcaagcc aaagacaccg cgttctacat cttcacctcg     720
ggcaccaccg gatttcccaa ggccagtgtc atgacgcatc atcggtggct gcgggcgctg     780
gccgtcttcg gagggatggg gctgcggctg aagggttccg acacgctcta cagctgcctg     840
ccgctgtacc acaacaacgc gttaacggtc gcggtgtcgt cggtgatcaa ttctggggcg     900
accctggcgc tgggtaagtc gttttcggcg tcgcggttct gggatgaggt gattgccaac     960
cgggcgacgg cgttcgtcta catcggcgaa atctgccgtt atctgctcaa ccagccggcc    1020
aagccgaccg accgtgccca ccaggtgcgg gtgatctgcg gtaacgggct gcggccggag    1080
atctgggatg agttcaccac ccgcttcggg gtcgcgcggg tgtgcgagtt ctacgccgcc    1140
agcgaaggca actcggcctt tatcaacatc ttcaacgtgc ccaggaccgc cggggtatcg    1200
ccgatgccgc ttgcctttgt ggaatacgac ctggacaccg cgatccgct gcgggatgcg    1260 agcgggcgag tgcgtcgggt acccgacggt gaacccggcc tgttgcttag ccgggtcaac    1320
cggctgcagc cgttcgacgg ctacaccgac ccggttgcca gcgaaaagaa gttggtgcgc    1380
aacgcttttc gagatggcga ctgttggttc aacaccggtg acgtgatgag cccgcagggc    1440
atgggccatg ccgccttcgt cgatcggctg gcgacacct tccgctgaa gggcgagaat    1500 gtcgccacca ctcaggtcga agcggcactg gcctccgacc agaccgtcga ggagtgcacg    1560
gtctacggcg tccagattcc gcgcaccggc gggcgcgccg aatgccgc gatcacactg    1620 cgcgctggcg ccgaattcga cggccaggcg ctggcccgaa cggtttacgg tcacttgccc    1680
ggctatgcac ttccgctctt tgttcgggta gtggggtcgc tggcgcacac cacgacgttc    1740
aagagtcgca aggtggagtt cgcaaccag gcctatggcg ccgacatcga ggatccgctg    1800
tacgtactgg ccgccccgga cgaaggatat gtgccgtact acgccgaata ccctgaggag    1860
gtttcgctcg gaaggcgacc gcagggctag cggattccgg gcgcagtctc gatacccgca    1920
```

-continued

```
ctggacgctc gacggtaacc aggcactatg gatgcgtgcg ttcaacaccg ccggcctcag    1980
ccggtcgttc aacaccgccg gcgttag                                        2007
```

<210> SEQ ID NO 23
<211> LENGTH: 597
<212> TYPE: PRT
<213> ORGANISM: Mycobacterium tuberculosis

<400> SEQUENCE: 23

| Met | Ser | Asp | Tyr | Tyr | Gly | Gly | Ala | His | Thr | Thr | Val | Arg | Leu | Ile | Asp |
|---|---|---|---|---|---|---|---|---|---|---|---|---|---|---|---|
| 1 | | | | 5 | | | | | 10 | | | | | 15 | |

Leu Ala Thr Arg Met Pro Arg Val Leu Ala Asp Thr Pro Val Ile Val
            20                  25                  30

Arg Gly Ala Met Thr Gly Leu Leu Ala Arg Pro Asn Ser Lys Ala Ser
        35                  40                  45

Ile Gly Thr Val Phe Gln Asp Arg Ala Ala Arg Tyr Gly Asp Arg Val
    50                  55                  60

Phe Leu Lys Phe Gly Asp Gln Gln Leu Thr Tyr Arg Asp Ala Asn Ala
65                  70                  75                  80

Thr Ala Asn Arg Tyr Ala Ala Val Leu Ala Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser

```
            355                 360                 365
Pro Met Pro Leu Ala Phe Val Glu Tyr Asp Leu Asp Thr Gly Asp Pro
    370                 375                 380

Leu Arg Asp Ala Ser Gly Arg Val Arg Val Pro Asp Gly Glu Pro
385                 390                 395                 400

Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
        435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
                485                 490                 495

Thr Gly Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
            580                 585                 590

Arg Arg Pro Gln Gly
        595

<210> SEQ ID NO 24
<211> LENGTH: 2221
<212> TYPE: DNA
<213> ORGANISM: Drosophila melanogaster

<400> SEQUENCE: 24
gctctctggg cctatatcaa gctgctgagg tacacgaagc gccatgagcg gctcaactac      60
acggtggcgg acgtcttcga acgaaatgtt caggcccatc cggacaaggt ggctgtggtc     120
agtgagacgc aacgctggac cttccgtcag gtgaacgagc atgcgaacaa ggtggccaat     180
gtgctgcagg ctcagggcta caaaaagggc gatgtggtgg ccctgttgct ggagaaccgc     240
gccgagtacg tggccacctg gctgggtctc tccaagatcg tgtgatcac accgctgatc      300 aacacgaatc tgcgcggtcc ctccctgctg cacagcatca cggtggccca ttgctcggct     360
ctcatttacg gcgaggactt cctggaagct gtcaccgacg tggccaagga tctgccagcg     420
aacctcacac tcttccagtt caacaacgag aacaacaaca gcgagacgga aagaacata      480 ccgcaggcca agaatctgaa cgcgctgctg accacggcca gctatgagaa gcctaacaag     540
acgcaggtta accaccacga caagctggtc tacatctaca cctccggcac cacaggattg     600
ccaaaggctg cggttatctc tcactcccgt tatctgttta cgctgctgg catccactac     660 accatgggtt ccaggagga ggacatcttc tacacgccct tgcctttgta ccacaccgct     720
```

-continued

```
ggtggcatta tgtgcatggg tcagtcggtg ctctttggct ccacggtctc cattcgcaag    780
aagttctcgg catccaacta tttcgccgac tgcgccaagt ataatgcaac tattggtcag    840
tatatcggtg agatggctcg ctacattcta gctacgaaac cctcggaata cgaccagaaa    900
caccgagtgc gtctggtctt tggaaacgga ctgcgaccgc agatttggcc acagtttgtg    960
cagcgcttca acattgccaa ggttggcgag ttctacggcg ccaccgaggg taatgcgaac   1020
atcatgaatc atgacaacac ggtgggcgcc atcggctttg tgtcgcgcat cctgcccaag   1080
atctacccaa tctcgatcat tcgcgccgat ccggacaccg agagcccat  tagagatagg   1140 aatggcctat gccaactgtg cgctcccaac gagccaggcg tattcatcgg caagatcgtc   1200
aaaggaaatc cttctcgcga attcctcgga tacgtcgatg aaaaggcctc cgcgaagaag   1260
attgttaagg atgtgttcaa gcatggcgat atggctttca tctccggaga tctgctggtt   1320
gccgacgaga agggttatct gtacttcaag gatcgcaccg tgacaccttc cgctggaag    1380 ggcgagaatg tttccaccag cgaggtggag gcgcaagtca gcaatgtggc cggttacaag   1440
gataccgtcg tttacggcgt aaccattccg cacaccgagg gaagggccgg catggccgcc   1500
atctatgatc cggagcgaga attggacctc gacgtcttcg ccgctagctt ggccaaggtg   1560
ctgcccgcgt acgctcgtcc ccagatcatt cgattgctca ccaaggtgga cctgactgga   1620
acctttaagc tgcgcaaggt agacctgcag aaggagggct acgatccgaa cgcgatcaag   1680
gacgcgctgt actaccagac ttccaagggt cggtacgagc tgctcacgcc ccaggtttac   1740
gaccaggtgc agcgcaacga aatccgcttc taagagctgc aatagagttg tgtctgaacc   1800 ttgcctttg  cccaatatgc tgttaattag tttgtaaggc taagtgtagt agaggaaaat   1860 cggggggaaat cggcagcaaa gatcattcag cctaggagag atgcatccga agcacatttc   1920
catgtcaaca atgcactttt gtatatcgta agcatatata tatcgtatat cgtaaacgta   1980
gttgtatctg catttgtgta gatgatagcc tcctatacgc atttcaattg tttttagcgt   2040
gctaaagaac cttgttaaat gcaatttcag ctattgttta gtcagttta  gtggcattta   2100 cacttccatt ctcgttgcgt ttcgtttttt cctgtacata tgagaagctc tgatgttttt   2160
gtatcaaata aagttttttc cttcaccacg gaccacgtga aaaaaaaaa  aaaaaaaa     2220 a                                                                  2221
```

<210> SEQ ID NO 25
<211> LENGTH: 590
<212> TYPE: PRT
<213> ORGANISM: Drosophila melanogaster

<400> SEQUENCE: 25

```
Ala Leu Trp Ala Tyr Ile Lys Leu Leu Arg Tyr Thr Lys Arg His Glu
 1               5                  10                  15

Arg Leu Asn Tyr Thr Val Ala Asp Val Phe Glu Arg Asn Val Gln Ala
            20                  25                  30

His Pro Asp Lys Val Ala Val Ser Glu Thr Gln Arg Trp Thr Phe
        35                  40                  45

Arg Gln Val Asn Glu His Ala Asn Lys Val Ala Asn Val Leu Gln Ala
    50                  55                  60

Gln Gly Tyr Lys Lys Gly Asp Val Val Ala Leu Leu Glu Asn Arg
65                  70                  75                  80

Ala Glu Tyr Val Ala Thr Trp Leu Gly Leu Ser Lys Ile Gly Val Ile
                85                  90                  95

Thr Pro Leu Ile Asn Thr Asn Leu Arg Gly Pro Ser Leu Leu His Ser
```

```
                100             105             110
Ile Thr Val Ala His Cys Ser Ala Leu Ile Tyr Gly Glu Asp Phe Leu
            115             120             125

Glu Ala Val Thr Asp Val Ala Lys Asp Leu Pro Ala Asn Leu Thr Leu
130             135             140

Phe Gln Phe Asn Asn Glu Asn Asn Ser Glu Thr Glu Lys Asn Ile
145             150             155             160

Pro Gln Ala Lys Asn Leu Asn Ala Leu Leu Thr Thr Ala Ser Tyr Glu
            165             170             175

Lys Pro Asn Lys Thr Gln Val Asn His His Asp Lys Leu Val Tyr Ile
            180             185             190

Tyr Thr Ser Gly Thr Thr Gly Leu Pro Lys Ala Ala Val Ile Ser His
            195             200             205

Ser Arg Tyr Leu Phe Ile Ala Ala Gly Ile His Tyr Thr Met Gly Phe
210             215             220

Gln Glu Glu Asp Ile Phe Tyr Thr Pro Leu Pro Leu Tyr His Thr Ala
225             230             235             240

Gly Gly Ile Met Cys Met Gly Gln Ser Val Leu Phe Gly Ser Thr Val
            245             250             255

Ser Ile Arg Lys Lys Phe Ser Ala Ser Asn Tyr Phe Ala Asp Cys Ala
            260             265             270

Lys Tyr Asn Ala Thr Ile Gly Gln Tyr Ile Gly Glu Met Ala Arg Tyr
            275             280             285

Ile Leu Ala Thr Lys Pro Ser Glu Tyr Asp Gln Lys His Arg Val Arg
            290             295             300

Leu Val Phe Gly Asn Gly Leu Arg Pro Gln Ile Trp Pro Gln Phe Val
305             310             315             320

Gln Arg Phe Asn Ile Ala Lys Val Gly Glu Phe Tyr Gly Ala Thr Glu
            325             330             335

Gly Asn Ala Asn Ile Met Asn His Asp Asn Thr Val Gly Ala Ile Gly
            340             345             350

Phe Val Ser Arg Ile Leu Pro Lys Ile Tyr Pro Ile Ser Ile Ile Arg
            355             360             365

Ala Asp Pro Asp Thr Gly Glu Pro Ile Arg Asp Arg Asn Gly Leu Cys
370             375             380

Gln Leu Cys Ala Pro Asn Glu Pro Gly Val Phe Ile Gly Lys Ile Val
385             390             395             400

Lys Gly Asn Pro Ser Arg Glu Phe Leu Gly Tyr Val Asp Glu Lys Ala
            405             410             415

Ser Ala Lys Lys Ile Val Lys Asp Val Phe Lys His Gly Asp Met Ala
            420             425             430

Phe Ile Ser Gly Asp Leu Leu Val Ala Asp Glu Lys Gly Tyr Leu Tyr
            435             440             445

Phe Lys Asp Arg Thr Gly Asp Thr Phe Arg Trp Lys Gly Glu Asn Val
450             455             460

Ser Thr Ser Glu Val Glu Ala Gln Val Ser Asn Val Ala Gly Tyr Lys
465             470             475             480

Asp Thr Val Val Tyr Gly Val Thr Ile Pro His Thr Glu Gly Arg Ala
            485             490             495

Gly Met Ala Ala Ile Tyr Asp Pro Glu Arg Glu Leu Asp Leu Asp Val
            500             505             510

Phe Ala Ala Ser Leu Ala Lys Val Leu Pro Ala Tyr Ala Arg Pro Gln
            515             520             525
```

```
Ile Ile Arg Leu Leu Thr Lys Val Asp Leu Thr Gly Thr Phe Lys Leu
        530                 535                 540
Arg Lys Val Asp Leu Gln Lys Glu Gly Tyr Asp Pro Asn Ala Ile Lys
545                 550                 555                 560
Asp Ala Leu Tyr Tyr Gln Thr Ser Lys Gly Arg Tyr Glu Leu Leu Thr
                565                 570                 575
Pro Gln Val Tyr Asp Gln Val Gln Arg Asn Glu Ile Arg Phe
            580                 585                 590
```

<210> SEQ ID NO 26
<211> LENGTH: 173
<212> TYPE: DNA
<213> ORGANISM: Danio rerio

<400> SEQUENCE: 26

```
agtgtagata ccacaggaac gtttaaaatc cagaagacca gactgcaaag ggaaggatac        60
gatccacggc tcacaactga ccagatctac ttcctaaact ccagagcagg gcgttacgag       120
cttgtcaacg aggagctgta caatgcattt gaacaagggc aggatttccc ttt             173
```

<210> SEQ ID NO 27
<211> LENGTH: 57
<212> TYPE: PRT
<213> ORGANISM: Danio rerio

<400> SEQUENCE: 27

```
Ser Val Asp Thr Thr Gly Thr Phe Lys Ile Gln Lys Thr Arg Leu Gln
 1               5                  10                  15
Arg Glu Gly Tyr Asp Pro Arg Leu Thr Thr Asp Gln Ile Tyr Phe Leu
                20                  25                  30
Asn Ser Arg Ala Gly Arg Tyr Glu Leu Val Asn Glu Glu Leu Tyr Asn
            35                  40                  45
Ala Phe Glu Gln Gly Gln Asp Phe Pro
        50                  55
```

<210> SEQ ID NO 28
<211> LENGTH: 1953
<212> TYPE: DNA
<213> ORGANISM: Caenorhabditis elegans

<400> SEQUENCE: 28

```
atgaagctgg aggagcttgt gacagttatg cttctcacag tggctgtcat tgctcagaat        60
cttccgattg gagtaatatt ggctggagtt cttattttat acatcacagt ggttcatgga       120
gatttcattt atagaagtta tcttacgttg aataggatt taacaggatt ggctctaatt       180
attgaagtca aaatcgacct atggtggagg ttgcatcaga ataaaggaat ccatgaactg       240
tttttggata ttgtgaaaaa gaatccaaat aagccggcga tgattgacat cgagacgaat       300
acaacagaaa catacgcaga gttcaatgca cattgtaata gatatgccaa ttatttccag       360
ggtcttggct atcgatccgg agacgttgtc gccttgtaca tggagaactc ggtcgagttt       420
gtggccgcgt ggatgggact cgcaaaaatc ggagttgtaa cggcttggat caactcgaat       480
ttgaaaagag agcaacttgt tcattgtatc actgcgagca agacaaaggc gattatcaca       540
agtgtaacac ttcagaatat tatgcttgat gctatcgatc agaagctgtt tgatgttgag       600
ggaattgagg tttactctgt cggagagccc aagaagaatt ctggattcaa gaatctcaag       660
aagaagttgg atgctcaaat tactacggaa ccaaagaccc ttgacatagt agattttaaa       720
```

-continued

```
agtattcttt gcttcatcta tacaagtggt actactggaa tgccaaaagc cgctgtcatg      780
aagcacttca gatattactc gattgccgtt ggagccgcaa atcattcgg atccgccct       840 tctgatcgta tgtacgtctc gatgccaatt tatcacactg cagctggaat tcttggagtt    900
gggcaagctc tgttgggtgg atcatcgtgt gtcattagaa aaaaattctc ggctagcaac    960
ttttggaggg attgtgtaaa gtatgattgt acagtttcac aatacattgg agagatttgt   1020
cggtacttgt tggctcagcc agttgtggaa gaggaatcca ggcatagaat gagattgttg   1080
gttggaaacg gactccgtgc tgaaatctgg caaccatttg tagatcgatt ccgtgtcaga   1140
attggagaac tttatggttc aactgaagga acttcatctc tcgtgaacat tgacggacat   1200
gtcggagctt gcggattctt gccaatatcc ccattaacaa agaaaatgca tccggttcga   1260
ttaattaagg ttgatgatgt cactggagaa gcaatccgaa cttccgatgg actttgcatt   1320
gcatgtaatc caggagagtc tggagcaatg gtgtcgacga tcagaaaaaa taatccatta   1380
ttgcaattcg agggatatct gaataagaag gaaacgaata aaaagattat cagagatgtc   1440
ttcgcaaagg gagatagttg cttttttgact ggagatcttc ttcattggga tcgtcttggt   1500
tatgtatatt tcaaggatcg tactggagat actttccgtt ggaagggaga gaatgtgtcg   1560
actactgaag tcgaggcaat tcttcatcca attactggat tgtctgatgc aactgtttat   1620
ggtgtagagg ttcctcaaag agagggaaga gttggaatgg cgtcagttgt tcgagttgta   1680
tcgcatgagg aagatgaaac tcaatttgtt catagagttg gagcaagact tgcctcttcg   1740
cttaccagct acgcgattcc tcagtttatg cgaatttgtc aggatgttga gaaaacaggt   1800
acattcaaac ttgtgaagac gaatctacaa cgattaggta tcatggatgc tccttcagat   1860
tcaatttaca tctacaattc tgaaaatcgc aattttgtgc cgttcgacaa tgatttgagg   1920
tgcaaggtct cactgggaag ttatccattt taa                                 1953
```

```
<210> SEQ ID NO 29
<211> LENGTH: 650
<212> TYPE: PRT
<213> ORGANISM: Caenorhabditis elegans

<400> SEQUENCE: 29

Met Lys Leu Glu Glu Leu Val Thr Val Met Leu Leu Thr Val Ala Val
 1               5                  10                  15

Ile Ala Gln Asn Leu Pro Ile Gly Val Ile Leu Ala Gly Val Leu Ile
                20                  25                  30

Leu Tyr Ile Thr Val Val His Gly Asp Phe Ile Tyr Arg Ser Tyr Leu
            35                  40                  45

Thr Leu Asn Arg Asp Leu Thr Gly Leu Ala Leu Ile Ile Glu Val Lys
        50                  55                  60

Ile Asp Leu Trp Trp Arg Leu His Gln Asn Lys Gly Ile His Glu Leu
65                  70                  75                  80

Phe Leu Asp Ile Val Lys Lys Asn Pro Asn Lys Pro Ala Met Ile Asp
                85                  90                  95

Ile Glu Thr Asn Thr Thr Glu Thr Tyr Ala Glu Phe Asn Ala His Cys
            100                 105                 110

Asn Arg Tyr Ala Asn Tyr Phe Gln Gly Leu Gly Tyr Arg Ser Gly Asp
        115                 120                 125

Val Val Ala Leu Tyr Met Glu Asn Ser Val Glu Phe Val Ala Ala Trp
    130                 135                 140

Met Gly Leu Ala Lys Ile Gly Val Val Thr Ala Trp Ile Asn Ser Asn
145                 150                 155                 160
```

```
Leu Lys Arg Glu Gln Leu Val His Cys Ile Thr Ala Ser Lys Thr Lys
                165                 170                 175

Ala Ile Ile Thr Ser Val Thr Leu Gln Asn Ile Met Leu Asp Ala Ile
            180                 185                 190

Asp Gln Lys Leu Phe Asp Val Glu Gly Ile Glu Val Tyr Ser Val Gly
        195                 200                 205

Glu Pro Lys Lys Asn Ser Gly Phe Lys Asn Leu Lys Lys Leu Asp
    210                 215                 220

Ala Gln Ile Thr Thr Glu Pro Lys Thr Leu Asp Ile Val Asp Phe Lys
225                 230                 235                 240

Ser Ile Leu Cys Phe Ile Tyr Thr Ser Gly Thr Thr Gly Met Pro Lys
                245                 250                 255

Ala Ala Val Met Lys His Phe Arg Tyr Tyr Ser Ile Ala Val Gly Ala
                260                 265                 270

Ala Lys Ser Phe Gly Ile Arg Pro Ser Asp Arg Met Tyr Val Ser Met
            275                 280                 285

Pro Ile Tyr His Thr Ala Ala Gly Ile Leu Gly Val Gly Gln Ala Leu
        290                 295                 300

Leu Gly Gly Ser Ser Cys Val Ile Arg Lys Lys Phe Ser Ala Ser Asn
305                 310                 315                 320

Phe Trp Arg Asp Cys Val Lys Tyr Asp Cys Thr Val Ser Gln Tyr Ile
                325                 330                 335

Gly Glu Ile Cys Arg Tyr Leu Leu Ala Gln Pro Val Val Glu Glu Glu
                340                 345                 350

Ser Arg His Arg Met Arg Leu Leu Val Gly Asn Gly Leu Arg Ala Glu
            355                 360                 365

Ile Trp Gln Pro Phe Val Asp Arg Phe Arg Val Arg Ile Gly Glu Leu
        370                 375                 380

Tyr Gly Ser Thr Glu Gly Thr Ser Ser Leu Val Asn Ile Asp Gly His
385                 390                 395                 400

Val Gly Ala Cys Gly Phe Leu Pro Ile Ser Pro Leu Thr Lys Lys Met
                405                 410                 415

His Pro Val Arg Leu Ile Lys Val Asp Asp Val Thr Gly Glu Ala Ile
                420                 425                 430

Arg Thr Ser Asp Gly Leu Cys Ile Ala Cys Asn Pro Gly Glu Ser Gly
            435                 440                 445

Ala Met Val Ser Thr Ile Arg Lys Asn Asn Pro Leu Leu Gln Phe Glu
        450                 455                 460

Gly Tyr Leu Asn Lys Lys Glu Thr Asn Lys Lys Ile Ile Arg Asp Val
465                 470                 475                 480

Phe Ala Lys Gly Asp Ser Cys Phe Leu Thr Gly Asp Leu Leu His Trp
                485                 490                 495

Asp Arg Leu Gly Tyr Val Tyr Phe Lys Asp Arg Thr Gly Asp Thr Phe
                500                 505                 510

Arg Trp Lys Gly Glu Asn Val Ser Thr Glu Val Glu Ala Ile Leu
            515                 520                 525

His Pro Ile Thr Gly Leu Ser Asp Ala Thr Val Tyr Gly Val Glu Val
        530                 535                 540

Pro Gln Arg Glu Gly Arg Val Gly Met Ala Ser Val Val Arg Val Val
545                 550                 555                 560

Ser His Glu Glu Asp Glu Thr Gln Phe Val His Arg Val Gly Ala Arg
                565                 570                 575
```

| Leu | Ala | Ser | Ser | Leu | Thr | Ser | Tyr | Ala | Ile | Pro | Gln | Phe | Met | Arg | Ile |
|---|---|---|---|---|---|---|---|---|---|---|---|---|---|---|---|
|  |  |  | 580 |  |  |  | 585 |  |  |  |  | 590 |  |  |  |

| Cys | Gln | Asp | Val | Glu | Lys | Thr | Gly | Thr | Phe | Lys | Leu | Val | Lys | Thr | Asn |
|---|---|---|---|---|---|---|---|---|---|---|---|---|---|---|---|
|  |  | 595 |  |  |  |  | 600 |  |  |  |  | 605 |  |  |  |

| Leu | Gln | Arg | Leu | Gly | Ile | Met | Asp | Ala | Pro | Ser | Asp | Ser | Ile | Tyr | Ile |
|---|---|---|---|---|---|---|---|---|---|---|---|---|---|---|---|
|  | 610 |  |  |  |  | 615 |  |  |  |  | 620 |  |  |  |  |

| Tyr | Asn | Ser | Glu | Asn | Arg | Asn | Phe | Val | Pro | Phe | Asp | Asn | Asp | Leu | Arg |
|---|---|---|---|---|---|---|---|---|---|---|---|---|---|---|---|
| 625 |  |  |  |  | 630 |  |  |  |  | 635 |  |  |  |  | 640 |

| Cys | Lys | Val | Ser | Leu | Gly | Ser | Tyr | Pro | Phe |
|---|---|---|---|---|---|---|---|---|---|
|  |  |  | 645 |  |  |  |  | 650 |  |

<210> SEQ ID NO 30
<211> LENGTH: 1968
<212> TYPE: DNA
<213> ORGANISM: Caenorhabditis elegans

<400> SEQUENCE: 30

```
atgagggaaa tgccggacag tcccaagttt gcgttagtca cgtttgttgt gtatgcagtg     60
gttttgtaca atgtcaacag cgttttctgg aaatttgtat tcatcggata tgttgtattt    120
aggctgcttc gcactgattt tggaagaaga gcacttgcca cgttacctag agattttgcg    180
ggactgaagc tcttaatatc ggttaagtcg acaattcgtg gcttgttcaa gaaagatcgc    240
ccaattcatg aaatcttttt gaatcaggtg aaacagcatc caaacaaagt ggcgattatt    300
gaaattgaaa gtggtaggca gttgacgtat caagaattga atgcgttagc taatcagtat    360
gctaaccttt acgtgagtga aggttacaaa atgggcgacg ttgtcgcttt gtttatggaa    420
aatagcatcg acttctttgc aatttggctg gactttcca agattggagt cgtgtcggcg    480
ttcatcaact caaacttgaa gttggagcca ttggcacatt cgattaatgt ttcgaagtgc    540
aaatcatgca ttaccaatat caatctgttg ccgatgttca agccgctcg tgaaaagaat    600
ctgatcagtg acgagatcca cgtgtttctg gctggaactc aggttgatgg acgtcataga    660
agtcttcagc aagatctcca tcttttctct gaggatgaac ctccagttat agacggactc    720
aattttagaa gcgttctgtg ttatatttac acttccggta ctaccggaaa tccaaagcca    780
gccgtcatta aacacttccg ttacttctgg attgcgatgg gagcaggaaa agcatttgga    840
attaataagt cagacgttgt gtacattacg atgccaatgt atcactctgc cgccggtatc    900
atgggtattg gatcattaat tgcattcggg tcgaccgctg ttattaggaa aaagttttcg    960
gcaagcaact tctggaaaga ttgcgtcaag tacaacgtca cagcgacaca gtacattgga   1020
gaaatctgca ggtatcttct ggcagcgaat ccatgtcctg aagagaaaca cacaacgtg    1080
cgattgatgt ggggaaatgg tttgagagga caaatttgga aagagtttgt aggaagattt   1140
ggaattaaga aaattggaga gttgtacggc tcaacagaag gaaactccaa tattgttaac   1200
gtggataacc atgttggagc ttgtggattc atgccaattt atccccatat ggatccctc   1260
tacccagttc gacttattaa ggttgataga gccactggag agcttgaacg tgataagaac   1320
ggactctgtg tgccgtgtgt gcctggtgaa actggggaaa tggttggcgt tatcaaggag   1380
aaagatattc ttctaaagtt cgaaggatat gtcagcgaag gggatactgc aaagaaaatc   1440
tacagagatg tgttcaagca tggagataag gtgtttgcaa gtggagatat tcttcattgg   1500
gatgatcttg atacttgta ctttgtggac cgttgtggag acactttccg ttggaaaggg   1560
gagaacgtgt caactactga agttgaggga attcttcagc ctgtgatgga tgtggaagat   1620
gcaactgttt atggagtcac tgtcggtaaa atggaggggc gtgccggaat ggctggtatt   1680
```

```
gtcgtcaagg atggaacgga tgttgagaaa ttcatcgccg atattacttc tcgactgacc   1740
gaaaatctgg cgtcttacgc aatccctgtt ttcattcggc tgtgcaagga agttgatcga   1800
accggaacct tcaaactcaa gaagactgat cttcaaaaac aaggttacga cctggttgct   1860
tgtaaaggag acccaattta ctactggtca gctgcagaaa atcctacaa accactgact   1920 gacaaaatgc aacaggatat tgacactggt gtttatgatc gcatttaa                1968
```

<210> SEQ ID NO 31
<211> LENGTH: 655
<212> TYPE: PRT
<213> ORGANISM: Caenorhabditis elegans

<400> SEQUENCE: 31

```
Met Arg Glu Met Pro Asp Ser Pro Lys Phe Ala Leu Val Thr Phe Val
  1               5                  10                  15

Val Tyr Ala Val Val Leu Tyr Asn Val Asn Ser Val Phe Trp Lys Phe
             20                  25                  30

Val Phe Ile Gly Tyr Val Val Phe Arg Leu Leu Arg Thr Asp Phe Gly
         35                  40                  45

Arg Arg Ala Leu Ala Thr Leu Pro Arg Asp Phe Ala Gly Leu Lys Leu
     50                  55                  60

Leu Ile Ser Val Lys Ser Thr Ile Arg Gly Leu Phe Lys Lys Asp Arg
 65                  70                  75                  80

Pro Ile His Glu Ile Phe Leu Asn Gln Val Lys Gln His Pro Asn Lys
                 85                  90                  95

Val Ala Ile Ile Glu Ile Glu Ser Gly Arg Gln Leu Thr Tyr Gln Glu
            100                 105                 110

Leu Asn Ala Leu Ala Asn Gln Tyr Ala Asn Leu Tyr Val Ser Glu Gly
        115                 120                 125

Tyr Lys Met Gly Asp Val Val Ala Leu Phe Met Glu Asn Ser Ile Asp
    130                 135                 140

Phe Phe Ala Ile Trp Leu Gly Leu Ser Lys Ile Gly Val Val Ser Ala
145                 150                 155                 160

Phe Ile Asn Ser Asn Leu Lys Leu Glu Pro Leu Ala His Ser Ile Asn
                165                 170                 175

Val Ser Lys Cys Lys Ser Cys Ile Thr Asn Ile Asn Leu Leu Pro Met
            180                 185                 190

Phe Lys Ala Ala Arg Glu Lys Asn Leu Ile Ser Asp Glu Ile His Val
        195                 200                 205

Phe Leu Ala Gly Thr Gln Val Asp Gly Arg His Arg Ser Leu Gln Gln
    210                 215                 220

Asp Leu His Leu Phe Ser Glu Asp Glu Pro Pro Val Ile Asp Gly Leu
225                 230                 235                 240

Asn Phe Arg Ser Val Leu Cys Tyr Ile Tyr Thr Ser Gly Thr Thr Gly
                245                 250                 255

Asn Pro Lys Pro Ala Val Ile Lys His Phe Arg Tyr Phe Trp Ile Ala
            260                 265                 270

Met Gly Ala Gly Lys Ala Phe Gly Ile Asn Lys Ser Asp Val Val Tyr
        275                 280                 285

Ile Thr Met Pro Met Tyr His Ser Ala Ala Gly Ile Met Gly Ile Gly
    290                 295                 300

Ser Leu Ile Ala Phe Gly Ser Thr Ala Val Ile Arg Lys Lys Phe Ser
305                 310                 315                 320

Ala Ser Asn Phe Trp Lys Asp Cys Val Lys Tyr Asn Val Thr Ala Thr
```

```
                    325                 330                 335
Gln Tyr Ile Gly Glu Ile Cys Arg Tyr Leu Leu Ala Ala Asn Pro Cys
                340                 345                 350

Pro Glu Glu Lys Gln His Asn Val Arg Leu Met Trp Gly Asn Gly Leu
            355                 360                 365

Arg Gly Gln Ile Trp Lys Glu Phe Val Gly Arg Phe Gly Ile Lys Lys
        370                 375                 380

Ile Gly Glu Leu Tyr Gly Ser Thr Glu Gly Asn Ser Asn Ile Val Asn
385                 390                 395                 400

Val Asp Asn His Val Gly Ala Cys Gly Phe Met Pro Ile Tyr Pro His
                405                 410                 415

Ile Gly Ser Leu Tyr Pro Val Arg Leu Ile Lys Val Asp Arg Ala Thr
                420                 425                 430

Gly Glu Leu Glu Arg Asp Lys Asn Gly Leu Cys Val Pro Cys Val Pro
            435                 440                 445

Gly Glu Thr Gly Glu Met Val Gly Val Ile Lys Glu Lys Asp Ile Leu
        450                 455                 460

Leu Lys Phe Glu Gly Tyr Val Ser Glu Gly Asp Thr Ala Lys Lys Ile
465                 470                 475                 480

Tyr Arg Asp Val Phe Lys His Gly Asp Lys Val Phe Ala Ser Gly Asp
                485                 490                 495

Ile Leu His Trp Asp Asp Leu Gly Tyr Leu Tyr Phe Val Asp Arg Cys
                500                 505                 510

Gly Asp Thr Phe Arg Trp Lys Gly Glu Asn Val Ser Thr Thr Glu Val
            515                 520                 525

Glu Gly Ile Leu Gln Pro Val Met Asp Val Glu Asp Ala Thr Val Tyr
        530                 535                 540

Gly Val Thr Val Gly Lys Met Glu Gly Arg Ala Gly Met Ala Gly Ile
545                 550                 555                 560

Val Val Lys Asp Gly Thr Asp Val Glu Lys Phe Ile Ala Asp Ile Thr
                565                 570                 575

Ser Arg Leu Thr Glu Asn Leu Ala Ser Tyr Ala Ile Pro Val Phe Ile
                580                 585                 590

Arg Leu Cys Lys Glu Val Asp Arg Thr Gly Thr Phe Lys Leu Lys Lys
            595                 600                 605

Thr Asp Leu Gln Lys Gln Gly Tyr Asp Leu Val Ala Cys Lys Gly Asp
        610                 615                 620

Pro Ile Tyr Tyr Trp Ser Ala Ala Glu Lys Ser Tyr Lys Pro Leu Thr
625                 630                 635                 640

Asp Lys Met Gln Gln Asp Ile Asp Thr Gly Val Tyr Asp Arg Ile
                645                 650                 655

<210> SEQ ID NO 32
<211> LENGTH: 1932
<212> TYPE: DNA
<213> ORGANISM: Cochliobolu heterostrophus

<400> SEQUENCE: 32
atggcgtgta tgcatcaggc tcagctatac aatgatctag aggaattgct aactggtcca      60
tcagtaccca tcgttgctgg agctgctgga gctgcagctc tcactgccta cattaacgcc     120
aaataccaca tagcccatga tctcaagacc ctcggtggtg gattgacaca atcgtccgaa     180
gcgattgatt tcataaaccg ccgcgtcgca caaaagcgcg tcctcacgca ccacatcttc     240
caggagcagg tccaaaaaca atcaaatcat ccctttctta tctttgaggg caagacatgg     300
```

-continued

```
tcttacaagg agttctctga ggcatacacg agggtcgcga actggctgat tgatgagctg      360
gacgtacaag tagggagat ggtcgcaatt gatggcggaa atagtgcaga gcacctgatg       420
ctttggcttg cacttgatgc aatcggtgcg gctacgagtt ttttgaactg gaacctgaca      480
ggggcagggt taattcattg cataaagcta tgcgaatgtc gattcgttat cgcagacatc      540
gatattaaag cgaacattga accgtgccgt ggcgaactgg aggagacggg catcaacatt     600
cactactatg acccatcctt catctcatcg ctaccgaata acacgccaat tcccgacagc      660
cgcactgaga acattgaatt agattcagta cgaggactga tatacacatc tggaaccact     720
ggtctaccta aggcgtgtt tataagcact ggccgcgagc ttaggactga ctggtcgatt      780
tcaaagtatc taaatctcaa gcccacggat cgaatgtata catgtatgcc gctctaccat    840
gccgctgcac acagcctctg tacagcatca gttattcatg gtggaggtac cgtggtattg    900
agcaggaaat tctcacacaa gaagttctgg cctgaagttg tggcttcgga agcaaatatc     960
attcagtacg ttggtgaatt aggtcgatat ctcctgaatg gtccaaagag tccttacgac    1020
agggcccata aagtccagat ggcgtggggc aatggcatgc gtccagacgt gtgggaagcg   1080
tttcgtgaac gcttcaacat accaattatt catgagctct atgccgcaac cgatgggctc    1140
gggtcaatga ccaatcgtaa cgcgggccct tttacagcaa actgtattgc gctgcgaggg    1200
ctgatctggc actggaaatt tcgaaatcag gaagtgctgg tcaagatgga tctcgatact   1260
gatgagatca tgagagatcg caatgggttt gcgatacgat gcgctgtcaa tgaacctgga    1320
cagatgcttt ttcggctgac acccgaaact ctggctggtg caccaagcta ctacaacaac    1380
gaaacggcca cacagagcag gcggattaca gatgtgtttc aaaagggtga cctgtggttc    1440
aagtccggtg acatgctacg gcaagacgcc gaaggccgcg tctactttgt cgatcgacta    1500
ggcgatacgt tccgctggaa atccgaaaac gtttctacca atgaagtcgc ggacgtgatg    1560
ggcacatttc ctcagattgc tgaaacgaat gtatacggtg tccttgtgcc gggtaacgat    1620
ggtcgagtgc gcagcctcaa ttgtcatggc agacggcgtg acagagtcga cattcgcttc    1680
gctgcccttg caaagcacgc ccgagatcgg ttaccgggtt atgctgtacc actgtttctg    1740
agggtaactc cagcacttga atatacgggc acattaaaga ttcagaaagg acgcctcaag    1800
caggaaggta tagacccaga taagatttcc ggcgaagata agttatactg gctgccgcct    1860
ggtagcgata tatatttacc atttggaaag atggagtggc agggaattgt agataagcgt    1920
atacggctgt ga                                                         1932
```

<210> SEQ ID NO 33
<211> LENGTH: 643
<212> TYPE: PRT
<213> ORGANISM: Cochliobolu heterostrophus

<400> SEQUENCE: 33

```
Met Ala Cys Met His Gln Ala Gln Leu Tyr Asn Asp Leu Glu Glu Leu
  1               5                  10                  15

Leu Thr Gly Pro Ser Val Pro Ile Val Ala Gly Ala Gly Ala Ala
                 20                  25                  30

Ala Leu Thr Ala Tyr Ile Asn Ala Lys Tyr His Ile Ala His Asp Leu
             35                  40                  45

Lys Thr Leu Gly Gly Gly Leu Thr Gln Ser Ser Glu Ala Ile Asp Phe
         50                  55                  60

Ile Asn Arg Arg Val Ala Gln Lys Arg Val Leu Thr His Ile Phe
 65                  70                  75                  80
```

```
Gln Glu Gln Val Gln Lys Gln Ser Asn His Pro Phe Leu Ile Phe Glu
                 85                  90                  95
Gly Lys Thr Trp Ser Tyr Lys Glu Phe Ser Glu Ala Tyr Thr Arg Val
            100                 105                 110
Ala Asn Trp Leu Ile Asp Glu Leu Asp Val Gln Val Gly Glu Met Val
        115                 120                 125
Ala Ile Asp Gly Gly Asn Ser Ala Glu His Leu Met Leu Trp Leu Ala
    130                 135                 140
Leu Asp Ala Ile Gly Ala Ala Thr Ser Phe Leu Asn Trp Asn Leu Thr
145                 150                 155                 160
Gly Ala Gly Leu Ile His Cys Ile Lys Leu Cys Glu Cys Arg Phe Val
                165                 170                 175
Ile Ala Asp Ile Asp Ile Lys Ala Asn Ile Glu Pro Cys Arg Gly Glu
            180                 185                 190
Leu Glu Glu Thr Gly Ile Asn Ile His Tyr Tyr Asp Pro Ser Phe Ile
        195                 200                 205
Ser Ser Leu Pro Asn Asn Thr Pro Ile Pro Asp Ser Arg Thr Glu Asn
    210                 215                 220
Ile Glu Leu Asp Ser Val Arg Gly Leu Ile Tyr Thr Ser Gly Thr Thr
225                 230                 235                 240
Gly Leu Pro Lys Gly Val Phe Ile Ser Thr Gly Arg Glu Leu Arg Thr
                245                 250                 255
Asp Trp Ser Ile Ser Lys Tyr Leu Asn Leu Lys Pro Thr Asp Arg Met
            260                 265                 270
Tyr Thr Cys Met Pro Leu Tyr His Ala Ala His Ser Leu Cys Thr
        275                 280                 285
Ala Ser Val Ile His Gly Gly Thr Val Val Leu Ser Arg Lys Phe
    290                 295                 300
Ser His Lys Lys Phe Trp Pro Glu Val Val Ala Ser Glu Ala Asn Ile
305                 310                 315                 320
Ile Gln Tyr Val Gly Glu Leu Gly Arg Tyr Leu Leu Asn Gly Pro Lys
                325                 330                 335
Ser Pro Tyr Asp Arg Ala His Lys Val Gln Met Ala Trp Gly Asn Gly
            340                 345                 350
Met Arg Pro Asp Val Trp Glu Ala Phe Arg Glu Arg Phe Asn Ile Pro
        355                 360                 365
Ile Ile His Glu Leu Tyr Ala Ala Thr Asp Gly Leu Gly Ser Met Thr
    370                 375                 380
Asn Arg Asn Ala Gly Pro Phe Thr Ala Asn Cys Ile Ala Leu Arg Gly
385                 390                 395                 400
Leu Ile Trp His Trp Lys Phe Arg Asn Gln Glu Val Leu Val Lys Met
                405                 410                 415
Asp Leu Asp Thr Asp Glu Ile Met Arg Asp Arg Asn Gly Phe Ala Ile
            420                 425                 430
Arg Cys Ala Val Asn Glu Pro Gly Gln Met Leu Phe Arg Leu Thr Pro
        435                 440                 445
Glu Thr Leu Ala Gly Ala Pro Ser Tyr Tyr Asn Asn Glu Thr Ala Thr
    450                 455                 460
Gln Ser Arg Arg Ile Thr Asp Val Phe Gln Lys Gly Asp Leu Trp Phe
465                 470                 475                 480
Lys Ser Gly Asp Met Leu Arg Gln Asp Ala Glu Gly Arg Val Tyr Phe
                485                 490                 495
```

-continued

```
Val Asp Arg Leu Gly Asp Thr Phe Arg Trp Lys Ser Glu Asn Val Ser
            500                 505                 510

Thr Asn Glu Val Ala Asp Val Met Gly Thr Phe Pro Gln Ile Ala Glu
        515                 520                 525

Thr Asn Val Tyr Gly Val Leu Val Pro Gly Asn Asp Gly Arg Val Arg
    530                 535                 540

Ser Leu Asn Cys His Gly Arg Arg Arg Asp Arg Val Asp Ile Arg Phe
545                 550                 555                 560

Ala Ala Leu Ala Lys His Ala Arg Asp Arg Leu Pro Gly Tyr Ala Val
                565                 570                 575

Pro Leu Phe Leu Arg Val Thr Pro Ala Leu Glu Tyr Thr Gly Thr Leu
            580                 585                 590

Lys Ile Gln Lys Gly Arg Leu Lys Gln Glu Gly Ile Asp Pro Asp Lys
        595                 600                 605

Ile Ser Gly Glu Asp Lys Leu Tyr Trp Leu Pro Pro Gly Ser Asp Ile
    610                 615                 620

Tyr Leu Pro Phe Gly Lys Met Glu Trp Gln Gly Ile Val Asp Lys Arg
625                 630                 635                 640

Ile Arg Leu

<210> SEQ ID NO 34
<211> LENGTH: 522
<212> TYPE: DNA
<213> ORGANISM: Magnaporthe grisea
<220> FEATURE:
<221> NAME/KEY: misc_feature
<222> LOCATION: (1)...(522)
<223> OTHER INFORMATION: n = A,T,C or G

<400> SEQUENCE: 34
gcaaaggccg acgcgtggct gcggacgggt aacgtgatca gggcggacaa cgaagggcga     60
ctcttcttcc acgaccggat cggagacacg ttccgatgga agggagagac ngtcagcaca    120
caagaggtca gtttggtgct cggacgacac gactcaatca aggaggccaa cgtgtacggc    180
gtgacggtgc cgaaccacga cgggcgggcc ggctgcgctg cgctcacgct atcagacgct    240
ctggcgactg aaaagaagct gggcgatgag ctgctaaagg gattggctac tcactcgtcg    300
acttcgcttc ccaagtttgc ggtgccgcag ttcctacggg tggtgcgcgg cgagatgcag    360
tcaacgggca ccaacaagca acagaagcac gacctgaggg tgcagggtgt agagccgggc    420
aaggtgggcg tagacgaggt gtactggttg cggggaggga catatgtacc attcggaaca    480
gaggattggg atgggttgaa gaagggtctt gtgaagttgt ga                       522

<210> SEQ ID NO 35
<211> LENGTH: 173
<212> TYPE: PRT
<213> ORGANISM: Magnaporthe grisea

<400> SEQUENCE: 35

Ala Lys Ala Asp Ala Trp Leu Arg Thr Gly Asn Val Ile Arg Ala Asp
 1               5                  10                  15

Asn Glu Gly Arg Leu Phe Phe His Asp Arg Ile Gly Asp Thr Phe Arg
            20                  25                  30

Trp Lys Gly Glu Thr Val Ser Thr Gln Glu Val Ser Leu Val Leu Gly
        35                  40                  45

Arg His Asp Ser Ile Lys Glu Ala Asn Val Tyr Gly Val Thr Val Pro
    50                  55                  60
```

```
Asn His Asp Gly Arg Ala Gly Cys Ala Ala Leu Thr Leu Ser Asp Ala
 65                  70                  75                  80

Leu Ala Thr Glu Lys Lys Leu Gly Asp Glu Leu Leu Lys Gly Leu Ala
                 85                  90                  95

Thr His Ser Ser Thr Ser Leu Pro Lys Phe Ala Val Pro Gln Phe Leu
                100                 105                 110

Arg Val Val Arg Gly Glu Met Gln Ser Thr Gly Thr Asn Lys Gln Gln
            115                 120                 125

Lys His Asp Leu Arg Val Gln Gly Val Glu Pro Gly Lys Val Gly Val
        130                 135                 140

Asp Glu Val Tyr Trp Leu Arg Gly Gly Thr Tyr Val Pro Phe Gly Thr
145                 150                 155                 160

Glu Asp Trp Asp Gly Leu Lys Lys Gly Leu Val Lys Leu
                165                 170
```

<210> SEQ ID NO 36
<211> LENGTH: 1794
<212> TYPE: DNA
<213> ORGANISM: Mycobacterium tuberculosis

<400> SEQUENCE: 36

| | | | | | |
|---|---|---|---|---|---|
| gtgtccgatt | actacggcgg | cgcacacaca | acggtcaggc | tgatcgacct | ggcaactcgg | 60 |
| atgccgcgag | tgttggcgga | cacgccggtg | attgtgcgtg | gggcaatgac | cgggctgctg | 120 |
| gcccggccga | attccaaggc | gtcgatcggc | acggtgttcc | aggaccgggc | cgctcgctac | 180 |
| ggtgaccgag | tcttcctgaa | attcggcgat | cagcagctga | cctaccgcga | cgctaacgcc | 240 |
| accgccaacc | ggtacgccgc | ggtgttggcc | gcccgcggcg | tcggccccgg | cgacgtcgtt | 300 |
| ggcatcatgt | tgcgtaactc | acccagcaca | gtcttggcga | tgctggccac | ggtcaagtgc | 360 |
| ggcgctatcg | ccggcatgct | caactaccac | cagcgcggcg | aggtgttggc | gcacagcctg | 420 |
| ggtctgctgg | acgcgaaggt | actgatcgca | gagtccgact | tggtcagcgc | cgtcgccgaa | 480 |
| tgcggcgcct | cgcgcggccg | ggtagcgggc | gacgtgctga | ccgtcgagga | cgtggagcga | 540 |
| ttcgccacaa | cggcgcccgc | caccaacccg | gcgtcggcgt | cggcggtgca | agccaaagac | 600 |
| accgcgttct | acatcttcac | ctcgggcacc | accggatttc | caaggccag | tgtcatgacg | 660 |
| catcatcggt | ggctgcgggc | gctggccgtc | ttcggaggga | tggggctgcg | gctgaagggt | 720 |
| tccgacacgc | tctacagctg | cctgccgctg | taccacaaca | acgcgttaac | ggtcgcggtg | 780 |
| tcgtcggtga | tcaattctgg | ggcgaccctg | gcgctgggta | agtcgttttc | ggcgtcgcgg | 840 |
| ttctgggatg | aggtgattgc | caaccgggcg | acggcgttcg | tctacatcgg | cgaaatctgc | 900 |
| cgttatctgc | tcaaccagcc | ggccaagccg | accgaccgtg | cccaccaggt | gcgggtgatc | 960 |
| tgcggtaacg | ggctgcggcc | ggagatctgg | gatgagttca | ccacccgctt | cggggtcgcg | 1020 |
| cgggtgtgcg | agttctacgc | cgccagcgaa | ggcaactcgg | cctttatcaa | catcttcaac | 1080 |
| gtgcccagga | ccgccgggt | atcgccgatg | ccgcttgcct | tgtggaata | cgacctggac | 1140 |
| accggcgatc | cgctgcggga | tgcgagcggg | cgagtgcgtc | gggtacccga | cggtgaaccc | 1200 |
| ggcctgttgc | ttagccgggt | caaccggctg | cagccgttcg | acggctacac | cgacccggtt | 1260 |
| gccagcgaaa | agaagttggt | gcgcaacgct | tttcgagatg | cgactgttg | gttcaacacc | 1320 |
| ggtgacgtga | tgagcccgca | gggcatgggc | catgccgcct | tcgtcgatcg | gctgggcgac | 1380 |
| accttccgct | ggaagggcga | gaatgtcgcc | accactcagg | tcgaagcggc | actggcctcc | 1440 |
| gaccagaccg | tcgaggagtg | cacggtctac | ggcgtccaga | ttccgcgcac | cggcgggcgc | 1500 |

```
gccggaatgg ccgcgatcac actgcgcgct ggcgccgaat cgacggcca ggcgctggcc      1560 cgaacggttt acgtcactt gcccggctat gcacttccgc tctttgttcg ggtagtgggg      1620
tcgctggcgc acaccacgac gttcaagagt cgcaaggtgg agttgcgcaa ccaggcctat      1680
ggcgccgaca tcgaggatcc gctgtacgta ctggccggcc cggacgaagg atatgtgccg      1740
tactacgccg aataccctga ggaggtttcg ctcggaaggc gaccgcaggg ctag            1794
```

<210> SEQ ID NO 37
<211> LENGTH: 597
<212> TYPE: PRT
<213> ORGANISM: Mycobacterium tuberculosis

<400> SEQUENCE: 37

```
Met Ser Asp Tyr Tyr Gly Gly Ala His Thr Thr Val Arg Leu Ile Asp
 1               5                  10                  15

Leu Ala Thr Arg Met Pro Arg Val Leu Ala Asp Thr Pro Val Ile Val
             20                  25                  30

Arg Gly Ala Met Thr Gly Leu Leu Ala Arg Pro Asn Ser Lys Ala Ser
         35                  40                  45

Ile Gly Thr Val Phe Gln Asp Arg Ala Ala Arg Tyr Gly Asp Arg Val
     50                  55                  60

Phe Leu Lys Phe Gly Asp Gln Gln Leu Thr Tyr Arg Asp Ala Asn Ala
 65                  70                  75                  80

Thr Ala Asn Arg Tyr Ala Ala Val Leu Ala Ala Arg Gly Val Gly Pro
                 85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
```

-continued

```
                        325                     330                     335
Phe Gly Val Ala Arg Val Cys Glu Phe Tyr Ala Ala Ser Glu Gly Asn
                340                     345                     350
Ser Ala Phe Ile Asn Ile Phe Asn Val Pro Arg Thr Ala Gly Val Ser
                355                     360                     365
Pro Met Pro Leu Ala Phe Val Glu Tyr Asp Leu Asp Thr Gly Asp Pro
            370                     375                     380
Leu Arg Asp Ala Ser Gly Arg Val Arg Arg Val Pro Asp Gly Glu Pro
385                     390                     395                     400
Gly Leu Leu Leu Ser Arg Val Asn Arg Leu Gln Pro Phe Asp Gly Tyr
                    405                     410                     415
Thr Asp Pro Val Ala Ser Glu Lys Lys Leu Val Arg Asn Ala Phe Arg
                420                     425                     430
Asp Gly Asp Cys Trp Phe Asn Thr Gly Asp Val Met Ser Pro Gln Gly
            435                     440                     445
Met Gly His Ala Ala Phe Val Asp Arg Leu Gly Asp Thr Phe Arg Trp
        450                     455                     460
Lys Gly Glu Asn Val Ala Thr Thr Gln Val Glu Ala Ala Leu Ala Ser
465                     470                     475                     480
Asp Gln Thr Val Glu Glu Cys Thr Val Tyr Gly Val Gln Ile Pro Arg
                485                     490                     495
Thr Gly Gly Arg Ala Gly Met Ala Ala Ile Thr Leu Arg Ala Gly Ala
                500                     505                     510
Glu Phe Asp Gly Gln Ala Leu Ala Arg Thr Val Tyr Gly His Leu Pro
            515                     520                     525
Gly Tyr Ala Leu Pro Leu Phe Val Arg Val Val Gly Ser Leu Ala His
        530                     535                     540
Thr Thr Thr Phe Lys Ser Arg Lys Val Glu Leu Arg Asn Gln Ala Tyr
545                     550                     555                     560
Gly Ala Asp Ile Glu Asp Pro Leu Tyr Val Leu Ala Gly Pro Asp Glu
                565                     570                     575
Gly Tyr Val Pro Tyr Tyr Ala Glu Tyr Pro Glu Glu Val Ser Leu Gly
                580                     585                     590
Arg Arg Pro Gln Gly
            595
```

POLYNUCLEOTIDES ENCODING FATTY ACID TRANSPORT PROTEINS

RELATED APPLICATIONS

This application claims the benefit of U.S. Provisional Application No. 60/071,374, filed Jan. 15, 1998, U.S. Provisional Application No. 60/093,491 filed Jul. 20, 1998 and U.S. Provisional Application No. 60/110,941 filed Dec. 4, 1998. The teachings of each of these applications are incorporated herein by reference in their entirety.

GOVERNMENT SUPPORT

The invention was supported, in whole or in part, by National Institutes of Health Grant DK 47618 and National Institutes of Health Grant 5 T32 CA 09541. The United States Government has certain rights in the invention.

BACKGROUND OF THE INVENTION

Long chain fatty acids (LCFAs) are an important source of energy for most organisms. They also function as blood hormones, regulating key metabolic functions such as hepatic glucose production. Although LCFAs can diffuse through the hydrophobic core of the plasma membrane into cells, this nonspecific transport cannot account for the high affinity and specific transport of LCFAs exhibited by cells such as cardiac muscle, hepatocytes, enterocytes, and adipocytes. The molecular mechanisms of LCFA transport remains largely unknown. Identifying these mechanisms can lead to pharmaceuticals that modulate fatty acid uptake by various organs, thereby alleviating certain medical conditions (e.g. obesity).

SUMMARY OF THE INVENTION

Described herein are members of a diverse family of fatty acid transport proteins (FATPs) which are evolutionarily conserved; these FATPs are plasma membrane proteins which mediate transport of LCFAs across the membranes and into cells. Members of the FATP family described herein are present in a wide variety of organisms, from mycobacteria to humans, and exhibit very different expression patterns in tissues. FATP family members are expressed in prokaryotic and eukaryotic organisms and comprise characteristic amino acid domains or sequences which are highly conserved across family members.

As described herein, four novel mouse FATPs, referred to as mmFATP2, mmFATP3, mmFATP4 and mmFATP5, and five human FATPs, referred to as, hsFATP2, hsFATP3, hsFATP4, hsFATP5 and hsFATP6, have been identified. Human FATPs 2–5 have orthologs in mice; the sixth human FATP (hsFATP6) does not as yet have a mouse ortholog. The expression patterns of these FATPs vary, as described below.

The present invention relates to FATP family members from prokaryotes and eukaryotes, nucleic acids (DNA, RNA) encoding FATPs, and nucleic acids which are useful as probes or primers (e.g., for use in hybridization methods, amplification methods) for example, in methods of detecting FATP-encoding genes, producing FATPs, and purifying or isolating FATP-encoding DNA or RNA. Also the subject of this invention are antibodies (polyclonal or monoclonal) which bind an FATP or FATPs; methods of identifying additional FATP family members (for example, orthologs of those FATPs described herein by amino acid sequence) and variant alleles of known FATP genes; methods of identifying compounds which bind to an FATP or to a polypeptide comprising a portion of a FATP, or modulate or alter (enhance or inhibit) FATP function; compounds which modulate or alter FATP function; methods of modulating or altering (enhancing or inhibiting) FATP function and, thus, LCFA uptake into tissues of a mammal (e.g., human) by administering a compound or molecule (a drug or agent) which increases or reduces FATP activity; and methods of targeting compounds to tissues by administering a complex of the compound to be targeted to tissues and a component which is bound by an FATP present on cells of the tissues to which the compound is to be targeted. For example, a complex of a drug to be delivered to the liver and a component which is bound by an FATP present on liver cells (e.g., FATP5) can be administered. In a further embodiment, LCFA uptake by the liver is modulated or altered (enhanced or reduced), in an individual. For example, a drug which inhibits the function of an FATP present in liver (e.g., FATP5) is administered to an individual who is diabetic, in order to reduce LCFA uptake by liver cells and, thus reduce insulin resistance.

The present invention, thus, provides methods which are useful to alter, particularly reduce, LCFA uptake in individuals and, as a result, to alter (particularly reduce), availability of the LCFAs for further metabolism. In a specific embodiment, the present invention provides methods useful to reduce LCFA uptake and, thus, fatty acid metabolism in individuals, with the result that caloric availability from fats is reduced, and circulating fatty acid levels are lower than they otherwise would be. These methods are useful, for example, as a means of weight control in individuals, (e.g., humans) and as a means of preventing elevated serum lipid levels or reducing serum lipid levels in humans.

The identification of this evolutionarily conserved fatty acid transporter family will allow a better understanding of the mechanisms whereby LCFAs traverse the lipid bilayer as well as yield insight into the control of energy homeostasis and its dysregulation in diseases such as diabetes and obesity.

BRIEF DESCRIPTION OF THE DRAWINGS

FIG. 2 is a phylogenetic tree showing the relationships among the FATP family members and VLACs, based on the 360 amino acid signature sequence of FATP.

FIG. 4A).

FIGS. 5A and 5B are the mmFATP3 DNA sequence (SEQ ID NO:6).

FIG. 6 is the mmFATP3 protein sequence (SEQ ID NO:7).

FIGS. 7A and 7B are the mmFATP4 DNA sequence (SEQ ID NO:8).

FIG. 8 is the mmFATP4 protein sequence (SEQ ID NO:9).

FIGS. 9A and 9B are the mmFATP5 DNA sequence (SEQ ID NO:10).

FIG. 10 is the mmFATP5 protein sequence (SEQ ID NO:11).

FIGS. 11A and 11B are the hsFATP2 DNA sequence (SEQ ID NO:12).

FIG. 12 is the hsFATP2 protein sequence (SEQ ID NO:13).

FIGS. 13A and 13B are the hsFATP3 DNA sequence (SEQ ID NO:14).

FIG. 14 is the hsFATP3 protein sequence (SEQ ID NO:15).

FIGS. 15A and 15B are the hsFATP4 DNA sequence (SEQ ID NO:16).

FIG. 16 is the hsFATP4 protein sequence (SEQ ID NO:17).

FIGS. 17A and 17B are the hsFATP5 DNA sequence (SEQ ID NO:18).

FIG. 18 is the hsFATP5 protein sequence (SEQ ID NO:19).

FIGS. 19A and 19B are the hsFATP6 DNA sequence (SEQ ID NO:20).

FIG. 20 is the hsFATP6 protein sequence (SEQ ID NO:21).

FIGS. 21A and 21B are the mtFATP DNA sequence (SEQ ID NO.22).

FIG. 22 is the mtFATP protein sequence (SEQ ID NO:23).

FIGS. 23A and 23B is a partial DNA sequence encoding a FATP of *Drosophila melanogaster* (SEQ ID NO:24).

FIG. 24 is a partial amino acid sequence of a *Drosophila melanogaster* FATP (SEQ ID NO:25).

FIG. 25 is a partial DNA sequence encoding a FATP of *Danio rerio* (SEQ ID NO:26).

FIG. 26 is a partial amino acid sequence of a *Danio rerio* (zebrafish) FATP (SEQ ID NO:27).

FIGS. 27A and 27B is a DNA sequence encoding FATPa of *Caenorhabditis elegans* (SEQ ID NO:28).

FIG. 28 is an amino acid sequence of *Caenorhabditis elegans* FATPa (SEQ ID NO:29).

FIGS. 29A and 29B is a DNA sequence encoding a FATPb of *Caenorhabditis elegans* (SEQ ID NO:30).

FIG. 30 is a amino acid sequence of *Caenorhabditis elegans* FATPb (SEQ ID NO:31).

FIGS. 31A and 31B is a DNA sequence encoding a FATP of *Cochliobolu heterostrophus* (SEQ ID NO:32).

FIG. 32 is an amino acid sequence of a *Cochliobolu heterostrophus* FATP (SEQ ID NO:33).

FIG. 33 is a partial DNA sequence encoding a FATP of *Magnaporthe grisea* (SEQ ID NO:34).

FIG. 34 is a partial amino acid sequence of a *Magnaporthe grisea* FATP (SEQ ID NO:35).

FIGS. 35A and 35B is a DNA sequence of a *Mycobacterium tuberculosis* FATP (SEQ ID NO:36).

FIG. 36 is an amino acid sequence of a *Mycobacterium tuberculosis* FATP (SEQ ID NO:37).

DETAILED DESCRIPTION OF THE INVENTION

Figure 1:
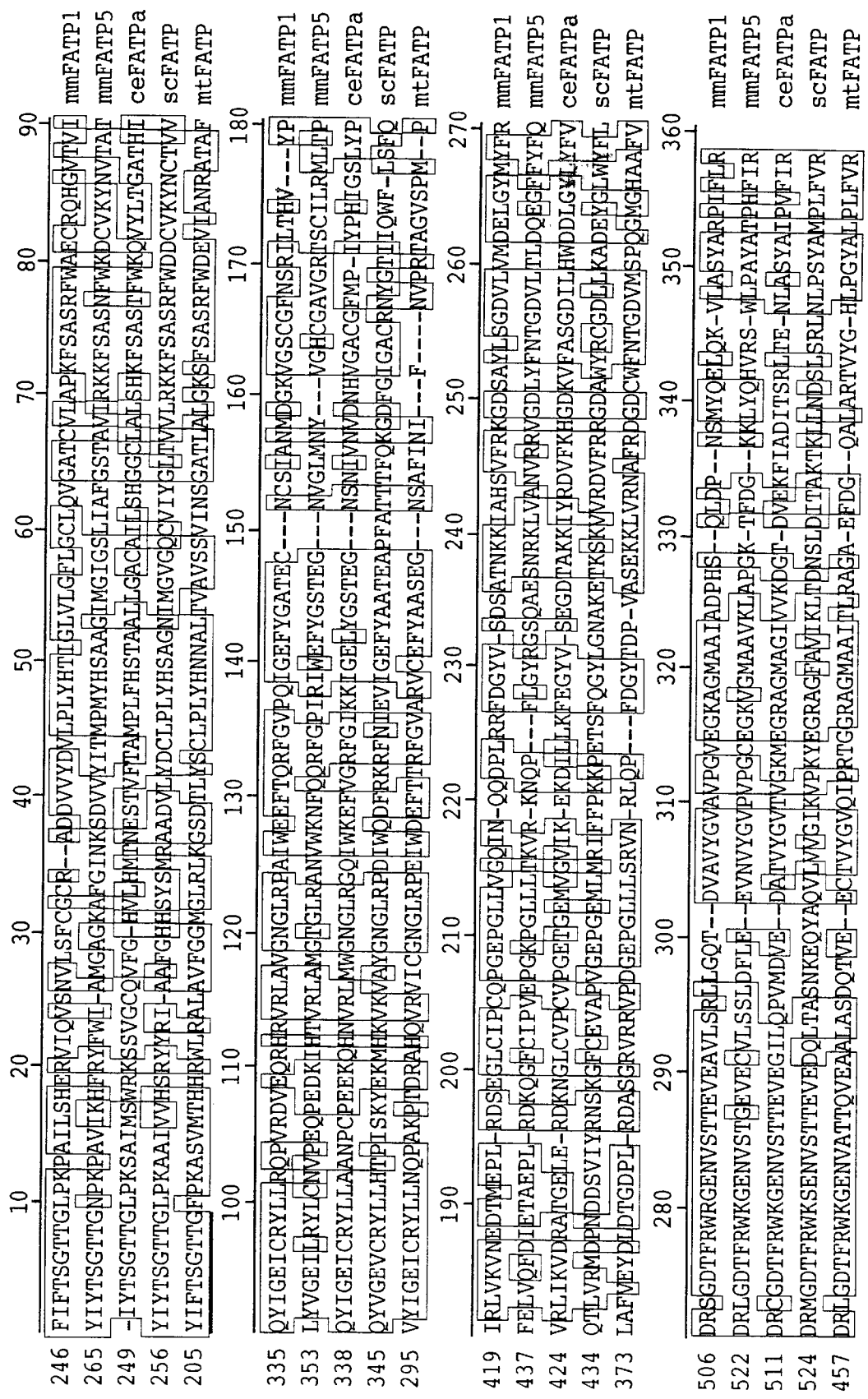
FIG. 1 shows the amino acid sequences of mmFATP1 (SEQ ID NO:1), mmFATP5 (SEQ ID NO:2), ceFATPA (SEQ ID NO:3), scFATP (SEQ ID NO:4), and mtFATP (SEQ ID NO:5).

As described herein, FATPs are a large evolutionarily conserved family of proteins that mediate the transport of LCFAs into cells. The family includes proteins which are conserved from mycobacteria to humans and exhibit very different expression patterns in tissues. Specific embodiments described include FATPs from mice, humans, nematodes, fungi, and mycobacteria. The term "fatty acid transport proteins" ("FATPs") as used herein, refers to the proteins described herein as FATP1, FATP2, FATP3, FATP4, FATP5 and FATP6, which have been described in one or more species of mammals, as well as mtFATP, ceFATPa, ceFATPb, dmFATP, drFATP, mgFATP, and chFATP and other proteins sharing at least about 50% amino acid sequence similarity, preferably at least about 60% sequence similarity, more preferably at least about 70% sequence similarity, and still more preferably, at least about 80% sequence similarity, and most preferably, at least about 90% sequence similarity in the approximately 360 amino acid signature sequence. The approximately 360 amino acid FATP signature sequence is shown in FIG. 1. The nomenclature used herein to refer to FATPs includes a species-specific prefix (e.g., mm, *Mus musculus*; hs or h, Homo sapiens or human; mt *M. tuberculosis*; ce, *C. elegans*; sc, *Saccharomyces cerevisiae*) and a number such that mammalian homologues in different species share the same number. For example, hsFATP4 and mmFATP4 are the human and mouse orthologs.

Expression patterns of human and mouse FATPs have been assessed and are described below. Briefly, results of these assessments show that FATP5 is a liver-specific gene. FATP2 is highly expressed in liver and kidney.

Long chain fatty acids (LCFAs) are an important energy source for pro- and eukaryotes and are involved in diverse cellular processes, such as membrane synthesis, intracellular signaling, protein modification, and transcriptional regulation. In developed Western countries, human dietary lipids are mainly di- and triglycerides and account for approximately 40% of caloric intake (Weisburger, J. H. (1997) *J. Am. Diet. Assoc.* 97:S16–S23). These lipids are broken down into fatty acids and glycerol by pancreatic lipases in the small intestine (Chapus, C., Rovery, M., Sarda, L & Verger, R. (1988) *Biochimie* 70:1223–34); LCFAs are then transported into brush border cells, where the majority is re-esterified and secreted into the lymphatic system as chylomicrons (Green, P. H. & Riley, J. W. (1981) *Aust. N.Z.J. Med.* 11:84–90). Fatty acids are liberated from lipoproteins by the enzyme lipoprotein lipase, which is bound to the luminal side of endothelial cells (Scow, R. O. & Blachette-Mackie, E. J. (1992) *Mol. Cell. Biochem* 116:181–191). "Free" fatty acids in the circulation are bound to serum albumin (Spector, A. A. (1984) *Clin. Physiol. Biochem* 2:123–134) and are rapidly incorporated by adipocytes, hepatocytes, and cardiac muscle cells. The latter derive 60–90% of their energy through the oxidation of LCFAs (Neely, J. F. Rovetto, M. J. & Oram, J. F. (1972) *Prog. Cardiovasc. Dis*: 15:289–329). Although saturable and specific uptake of LCFAs has been demonstrated for intestinal cells, hepatocytes, cardiac myocytes, and adipocytes, the molecular mechanisms of LCFA transport across the plasma membrane have remained controversial (Hui, T. Y. & Bernlohr, D. A. (1997) *Front. Biosci.* 15:d222–31–d231; Schaffer, J. E. & Lodish, H. F, (1995) *Trends Cardiovasc. Med.* 5:218–224). Described herein is a large family of highly homologous mammalian LCFA transporters which show wide expression. Further described are novel members of this family in other species, including mycobacterial, fungal and nematode FATPs.

The discovery of a diverse but highly homologous family of FATPs is reminiscent of the glucose transporter family. In a manner similar to the FATPs, the glucose transporters have very divergent patterns of tissue expression (McGowan, K. M., Long, S. D. & Pekala, P. H. (1995) *Pharmacol. Ther.* 66:465–505). The FATPs, like glucose transporters, may also differ in their substrate specificities, uptake kinetics, and hormonal regulation (Thorens, B. (1996) *Am. J. Physiol.* 270:G541–G553). Indeed, the levels of fatty acids in the blood, like those of glucose, can be regulated by insulin and are dysregulated in diseases such as noninsulin-dependent diabetes and obesity (Boden, G. (1997) *Diabetes* 46:3–10). The underlying mechanisms for the regulation of free fatty acid concentrations in the blood are not understood, but could be explained by hormonal modulation of FATPs.

Insulin-resistance is thought to be the major defect in non insulin-dependent diabetes mellitus (NIDDM) and is one of the earliest manifestations of NIDDM (McGarry (1992) *Science* 258:766–770). Free fatty acids (FFAs) may provide an explanation for why obesity is a risk factor for NIDDM. Plasma levels of FFAs are elevated in diabetic patients (Reaven et al. (1988) *Diabetes* 37:1020). Elevated plasma free fatty acids (FFAs) have been demonstrated to induce insulin-resistance in whole animals and humans (Boden (1998) *Front. Biosci.* 3:D169–D175). This insulin-resistance is likely mediated by effects of FFAs on a variety of issues. FFAs added to adipocytes in vitro induce insulin resistance in this cell type as evidenced by inhibition of insulin-induced glucose transport (Van Epps-Fung et al. (1997) *Endocrinology* 138:4338–4345). Rats fed a high fat diet developed skeletal muscle insulin resistance as evidenced by a decrease in insulin-induced glucose uptake by skeletal muscle (Han et al., (1997) *Diabetes* 46:1761–1767). In addition, elevated plasma FFAs increase insulin-suppressed endogenous glucose production in the liver (Boden (1998) *Front. Biosci.* 3:D169–D175), thus increasing hepatic glucose output. It has been postulated that the adverse effects of plasma free fatty acids are due to the FFAs being taken up into the cell, leading to an increase in intracellular long chain fatty acyl CoA; intracellular long chain acyl CoAs are thought to mediate the effects of FFAs inside the cell. Thus, fatty acid induced insulin-resistance may be prevented by blocking uptake of FFAs into select tissues, in particular liver (by blocking FATP2 and/or FATP5), adipocyte (by blocking FATP1), and skeletal muscle (by blocking FATP1). Blocking intestinal fat absorption (by blocking FATP4) is also expected to reduce plasma FFA levels and thus improve insulin resistance.

During the pathogenesis of NIDDM insulin-resistance can initially be counteracted by increasing insulin output by the pancreatic beta cell. Ultimately, this compensation fails, beta cell function decreases and overt diabetes results (McGarry (1992) *Science* 258: 766–770). Manipulating beta cell function is a second point where fatty acid transporter blockers may be beneficial for diabetes. While no FATP homolog has been identified so far that is expressed in the beta cell of the pancreas, the data described below suggest the existence of such a transporter and the sequence information included herein provides the means to identify such a transporter by degenerate PCR, using primers to regions conserved in all FATP family members or by low stringency hybridization. It has been demonstrated that exposure of pancreatic beta-cells to FFAs increases the basal rate of insulin secretion; this in turn leads to a decrease in the intracellular stores of insulin, resulting in decreased capacity for insulin secretion after chronic exposure (Bollheimer et al., (1998) *J. Clin. Invest.* 101:1094–1101). The effects of FFAs are again likely to be mediated by intracellular long chain fatty acyl CoA molecules (Liu et al., (1998) *J. Clin. Invest.* 101:1870–1875). FFAs have also been demonstrated to increase beta cell apoptosis (Shimabukuro et al., (1998) *Proc. Nat. Acad. Sci. USA* 95:2498–2502), possibly contributing to the decrease in beta cell numbers in late stage NIDDM.

Another finding with potentially broad implications is the identification of a FATP homologue in *M tuberculosis*. Tuberculosis causes more deaths worldwide than any other infectious agent and drug-resistant tuberculosis is re-emerging as a problem in industrialized nations (Bloom, B. R. & Small, P. M. (1998) *N. Engl. J. Med.* 338:677–678). *Mycobacterium tuberculosis* has about 250 enzymes involved in fatty acid metabolism, compared with only about 50 in *E. coli*. It has been suggested that, living as a pathogen, the mycobacteria are largely lipolytic, rather than lipogenic, relying on the lipds within mammalian cells and the tubercle (Cole, S. T. et al., *Nature* 393:537–544 (1998)). The de novo synthesis of fatty acids in *Mycobacterium leprae* is insufficient to maintain growth (Wheeler, P. R., Bulmer, K & Ratledge, C. (1990) *J. Gene. Microbiol.* 136:211–217). Thus, it is reasonable to expect that inhibitors of mtFATP will serve as therapeutics for tuberculosis. FATPs expressed in mycobacteria can be targeted to reduce or prevent replication of mycobacteria (e.g., to reduce or prevent replication of *M. tuberculosis*) and, thus, reduce or prevent their adverse effects. For example, a FATP or FATPs expressed by *M. tuberculosis* can be targeted and inhibited, thus reducing or preventing growth of this pathogen (and tuberculosis in humans and other mammals). An inhibitor of an *M. tuberculosis* FATP can be identified, using methods described herein (e.g., expressing the FATP in an appropriate host cell, such as *E. coli* or COS cells; contacting the cells with an agent or drug to be assessed for its ability to inhibit the FATP and, as a result, mycobacterial growth, and assessing its effects on growth). A drug or agent identified in this manner can be further tested for its ability to inhibit a *M. tuberculosis* FATP and *M. tuberculosis* infection in an appropriate animal model or in humans. A method of inhibiting mycobacterial growth, particularly growth of *M. tuberculosis*, and compounds useful as drugs for doing so are also the subject of this invention.

An isolated polynucleotide encoding mtFATP, like other polynucleotides encoding FATPs of the FATP family, can be incorporated into vectors, nucleic acids of viruses, and other nucleic acid constructs that can be used in various types of host cells to produce mtFATP. This mtFATP can be used, as it appears on the surface of cells, or in various artificial membrane systems, to assess fatty acid transport function, to identify ligands and molecules that are modulators of fatty acid transport activity. Molecules found to be inhibitors of mtFATP function can be incorporated into pharmaceutical compositions to administer to a human for the treatment of tuberculosis.

Particular embodiments of the invention are polynucleotides encoding a FATP of *Cochliobolus* (*Helminthosporium*) *heterostrophus* or portions or variants thereof, the isolated or recombinantly produced FATP, methods for assessing whether an agent binds to the chFATP, and further methods for assessing the effect of an agent being tested for its ability to modulate fatty acid transport activity. *Cochliobolus heterostrophus* is an ascomycete that is the cause of southern corn leaf blight, an economically important threat to the corn crop in the United States. The related species *C. sativus* causes crown rot and common root rot in wheat and barley. One or more FATPs of *C. heterostrophus* can be targeted for the identification of an inhibitor of chFATP function, which can be then be used as an agent effective against infection of plants by *C. heterostrophus* and related organisms. Methods described herein that were applied in studying the expression of a FATP gene and the function of the FATP in its natural site of expression or in a host cell, can be used in the study of the chFATP gene and protein.

*Magnaporthe grisea* (rice blast) is an economically important fungal pathogen of rice. Further embodiments of the invention are nucleic acid molecules encoding a FATP of

*Magnaporthe grisea*, portions thereof, or variants thereof, isolated mgFATP, nucleic acid constructs, and engineered cells expressing mgFATP. Other aspects of the invention are assays to identify an agent which binds to mgFATP and assays to identify an agent which modulates the function of mgFATP in cells in which mgFATP is expressed or in artificial membrane systems. Agents identified as inhibiting mgFATP activity can be developed into anti-fungal agents to be used to treat rice infected with rice blast.

*Caenorhabditis elegans* is a nematode related to plant pathogens and human parasites. An isolated polynucleotide which encodes ceFATP, like other polynucleotides encoding FATPs of the FATP family described herein, can be incorporated into nucleic acid vectors and other constructs that can be used in various types of cells to produce ceFATP. ceFATP as it occurs in cells or as it can be isolated or incorporated into various artificial or reconstructed membrane systems, can be used to assess fatty acid transport, and to identify ligands and agents that modulate fatty acid transport activity. Agents found by such assays to be inhibitors of ceFATP activity can be incorporated into compositions for the treatment of diseases caused by genetically related organisms with a FATP of similar sensitivity to the agents.

One aspect of the invention relates to isolated nucleic acids that encode a FATP as described herein, such as those FATPs having an amino acid sequence shown in the figures, and nucleic acids closely related thereto as described herein.

Using the information provided herein, such as a nucleic acid sequence set forth in FIGS. 5A–5B (SEQ ID NO:6), FIGS. 7A and 7B (SEQ ID NO:8), FIGS. 9A–9B (SEQ IDNO:10), FIGS. 11A–11B (SEQ IDNO:12), FIGS. 13A and 13B (SEQ ID NO:14), and FIGS. 15A–15B (SEQ ID NO:16), FIGS. 17A and 17B (SEQ ID NO:18, FIGS. 19A and 19B (SEQ ID NO:20), and FIGS. 21A and 21B (SEQ ID NO:22), a nucleic acid of the invention encoding a FATP polypeptide may be obtained using standard cloning and screening methods, such as those for cloning and sequencing cDNA library fragments, followed by obtaining a full length clone. For example, to obtain a nucleic acid of the invention, a library of clones of cDNA of human or other mammalian DNA can be probed with a labeled oligonucleotide, such as a radiolabeled oligonucleotide, preferably about 17 nucleotides or longer, derived from a partial sequence. Clones carrying DNA identical to that of the probe can then be distinguished using stringent (also, "high stringency") hybridization conditions. By sequencing the individual clones thus identified with sequencing primers designed from the original sequence it is then possible to extend the sequence in both directions to determine the full length sequence. Suitable techniques are described, for example, in *Current Protocols in Molecular Biology* (F. M. Ausubel et al, eds), containing supplements through Supplement 42, 1998, John Wiley and Sons, Inc., especially chapters 5, 6, and 7. Embodiments of the invention include isolated nucleic acid molecules comprising any of the following nucleotide sequences: 1.) a nucleotide sequence which encodes a protein comprising the amino acid sequence of ceFATPa (SEQ ID NO:29), mgFATP (SEQ ID NO:35), ceFATP6 (SEQ ID NO:31), mmFATP3 (SEQ ID NO:7), mmFATP4 (SEQ ID NO:9), mmFATP5 (SEQ ID NO:11), hsFATP2 (SEQ ID NO:13), hsFATP3 (SEQ ID NO:15), hsFATP4 (SEQ ID NO:17), hsFATP5 (SEQ ID NO:19), hsFATP6 (SEQ ID NO:21), chFATP (SEQ ID NO:33), mtFATP (SEQ ID NO:23); 2.) nucleotide sequences described herein, such as those encoding hsFATP2, hsFATP3, hsFATP4, hsFATP5, hsFATP6, mmFATP3, mmFATP4, mmFATP5, or mtFATP, respectively); 3.) a nucleotide sequence which is complementary to the nucleotide sequences appearing herein; 4.) a nucleotide sequence which consists of the coding region for a FATP as described herein.

The invention further relates to nucleic acids (nucleic acid molecules or polynucleotides) having nucleotide sequences identical over their entire length to those nucleotide sequences shown in the figures. It further relates to DNA, which due to the degeneracy of the genetic code, encodes a FATP encoded by one of the FATP-encoding DNAs, whose amino acid sequence is provided herein. Also provided by the invention are nucleic acids having the coding sequences for the mature polypeptides or fragments in reading frame with other coding sequences, such as those encoding a leader or secretory sequence, a pre-, or pro- or prepro-protein sequence. The nucleic acids of the invention encompass nucleic acids that include a single continuous region or discontinuous regions encoding the polypeptide, together with additional regions, that may also contain coding or non-coding sequences. The nucleic acids may also contain non-coding sequences, including, for example, but not limited to, non-coding 5' and 3' sequences, such as the transcribed, non-translated sequences, termination signals, ribosome binding sites, sequences that stabilize mRNA, introns, polyadenylation signals, and additional coding sequences which encode additional amino acids. For example, a marker sequence that facilitates purification of the fused polypeptide can be encoded. In certain embodiments of the invention, the marker sequence can be a hexahistidine peptide, as provided in the pQE vector (Qiagen, Inc.) and described in Gentz et al., *Proc. Natl. Acad. Sci. USA* 86: 821–824 (1989), or an HA tag (Wilson et al., *Cell* 37: 767 (1984)), or a sequence encoding glutathione S-transferase of *Schistosoma japonicum* (vectors available from Pharmacia; see Smith, D. B. and Johnson K. S., Gene 67:31 (1988) and Kaelin, W. G. et al., *Cell* 70:351 (1992)). Nucleic acids of the invention also include, but are not limited to, nucleic acids comprising a structural gene and its naturally associated sequences that control gene expression.

The invention further relates to variants, including naturally-occurring allelic variants, of those nucleic acids described specifically herein by DNA sequence, that encode variants of such polypeptides as those having the amino acid sequences shown in FIG. 28 (SEQ ID NO:29), FIG. 30 (SEQ ID NO:31), FIG. 32 (SEQ ID NO:33), FIG. 34 (SEQ ID NO:35), FIG. 6 (SEQ ID NO:7), FIG. 8 (SEQ ID NO:9), FIG. 10 (SEQ ID NO:11), FIG. 12 (SEQ ID NO:13) FIG. 4 (SEQ ID NO:15), FIG. 16 (SEQ ID NO:17), FIG. 18 (SEQ ID NO:19), FIG. 20 (SEQ ID NO:21), and FIG. 22 (SEQ ID NO:23). Such variants include nucleic acids encoding variants of the above-listed amino acid sequences, wherein those variants have several, such as 5 to 10, 1 to 5, or 3, 2 or 1 amino acids substituted, deleted, or added, in any combination. Variants include polynucleotides encoding polypeptides with at least 95% but less than 100% amino acid sequence identity to the polypeptides described herein by amino acid sequence. Variant polynucleotides hybridize, under low to high stringency conditions, to the alleles described herein by DNA sequence. In one embodiment, nucleic acid variants have silent substitutions, additions and deletions that do not alter the properties and activities of the encoded FATP.

Orthologous genes are gene loci in different species that are sufficiently similar to each other in their nucleotide sequences to suggest that they originated from a common ancestral gene. Orthologous genes arise when a lineage splits into two species, rather than when a gene is duplicated within a genome. Proteins that are orthologs are encoded by genes of two different species, wherein the genes are said to be orthologous.

The invention further relates to polynucleotides encoding polypeptides which are orthologous to those polypeptides having a specific amino acid sequence described herein. These polynucleotides, which can be called ortholog polynucleotides, encode orthologous polypeptides that can range in amino acid sequence identity to a reference amino acid sequence described herein, from about 65% to less than 100%, but preferably 70% to 80%, more preferably 80% to 90%, and still more preferably 90% to less than 100%. Orthologous polypeptides can also be those polypeptides that range in amino acid sequence similarity to a reference amino acid sequence described herein from about 75% to 100%, within the signature sequence. The amino acid sequence similarity between the signature sequences of orthologous polypeptides is preferably 80%, more preferably 90%, and still more preferably, 95%. The ortholog polynucleotides encode polypeptides that have similar functional characteristics (e.g., fatty acid transport activity) and similar tissue distribution, as appropriate to the organism from which the ortholog polynucleotides can be isolated.

Ortholog polynucleotides can be isolated from (e.g., by cloning or nucleic acid amplification methods) a great number of species, as shown by the sample of FATPs from evolutionarily divergent species described herein. Ortholog polynucleotides corresponding to those having the nucleotide sequences shown in the figures are those which can be isolated from mammals such as rat, dog, chimpanzee, monkey, baboon, pig, rabbit and guinea pig, for example.

Further variants that are fragments of the nucleic acids of the invention may be used to synthesize full-length nucleic acids of the invention, such as by use as primers in a polymerase chain reaction. As used herein, the term primer refers to a single-stranded oligonucleotide which acts as a point of initiation of template-directed DNA synthesis under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term primer site refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

Further embodiments of the invention are nucleic acids that are at least 80% identical over their entire length to a nucleic acid described herein. Additional embodiments are nucleic acids, and the complements of such nucleic acids, having at least 90% nucleotide sequence identity to the above-described sequences, and nucleic acids having at least 95% nucleotide sequence identity. In preferred embodiments, DNA of the present invention has 97% nucleotide sequence identity, 98% nucleotide sequence identity, or at least 99% nucleotide sequence identity with the DNA whose sequences are presented herein.

Other embodiments of the invention are nucleic acids that are at least 80% identical in nucleotide sequence to a nucleic acid encoding a polypeptide having an amino acid sequence as set forth in herein, and nucleic acids that are complementary to such nucleic acids. Specific embodiments are nucleic acids having at least 90% nucleotide sequence identity to a nucleic acid encoding a polypeptide having an amino acid sequence as described in the list above, nucleic acids having at least 95% sequence identity, and nucleic acids having at least 97% sequence identity.

The terms "complementary" or "complementarity" as used herein, refer to the natural binding of polynucleotides under permissive salt and temperature conditions by base-pairing. Complementarity between two single-stranded molecules may be "partial" in which only some of the nucleic acids bind, or it may be complete when total complementarity exists between the single-stranded molecules (that is, when A-T and G-C base pairing is 100% complete). The degree of complementarity between nucleic acid strands has significant effects on the efficiency and strength of hybridization between nucleic acid strands. This is of particular importance in amplification reactions, which depend on binding between nucleic acid strands.

The invention further includes nucleic acids that hybridize to the above-described nucleic acids, especially those nucleic acids that hybridize under stringent hybridization conditions. "Stringent hybridization conditions" or "high stringency conditions" generally occur within a range from about $T_m$ minus 5° C. (5° C. below the strand dissociation temperature or melting temperature ($T_m$) of the probe nucleic acid molecule) to about 20° C. to 25° C. below $T_m$. As will be understood by those of skill in the art, the stringency of hybridization may be altered in order to identify or detect molecules having identical or related polynucleotide sequences. An example of high stringency hybridization follows. Hybridization solution is (6×SSC/10 mM EDTA/0.5% SDS/5×Denhardt's solution/100 $\mu$g/ml sheared and denatured salmon sperm DNA). Hybridization is at 64–65° C. for 16 hours. The hybridized blot is washed two times with 2×SSC/0.5% SDS solution at room temperature for 15 minutes each, and two times with 0.2×SSC/0.5% SDS at 65° C., for one hour each. Further examples of high stringency conditions can be found on pages 2.10.1–2.10.16 (see particularly 2.10.8–11) and pages 6.3.1–6 in *Current Protocols in Molecular Biology* (Ausubel, F. M. et al., eds., containing supplements up through Supplement 42, 1998). Examples of high, medium, and low stringency conditions can be found on pages 36 and 37 of WO 98/40404, which are incorporated herein by reference.

The invention further relates to nucleic acids obtainable by screening an appropriate library with a probe having a nucleotide sequence such as one set forth herein, or a probe which is a sufficiently long portion of these sequences; and isolating the nucleic acid. Such probes generally can comprise at least 15 nucleotides. Nucleic acids obtainable by such screenings may include RNAs, cDNAs and genomic DNA, for example, encoding FATPs of the FATP family described herein.

Further uses for the nucleic acid molecules of the invention, whether encoding a full-length FATP or whether comprising a contiguous portion of a nucleic acid molecule described herein by sequence include use as markers for tissues in which the corresponding protein is preferentially expressed (to identify constitutively expressed proteins or proteins produced at a particular stage of tissue differentiation or stage of development of a disease state); as molecular weight markers on southern gels; as chromosome markers or tags (when labeled, for example with biotin, a radioactive label or a fluorescent label) to identify chromosomes or to map related gene positions; to compare with endogenous DNA sequences in a mammal to identify potential genetic disorders; as probes to hybridize and thus identify, related DNA sequences; as a source of information to derive PCR primers for genetic fingerprinting; as a probe to "subtract-out" known sequences in the process of discovering other novel nucleic acid molecules; for selecting and making oligomers for attachment to a "gene chip" or other support, to be used, for example, for examination of expression patterns; to raise anti-protein antibodies using DNA immunization techniques; and as an antigen to raise anti-DNA antibodies or to elicit another immune response.

Further methods to obtain nucleic acids encoding FATPs of the FATP family include PCR and variations thereof (e.g., "RACE" PCR and semi-specific PCR methods). Portions of the nucleic acids having a nucleotide sequence set forth herein, (especially "flanking sequences" on either side of a coding region) can be used as primers in methods using the polymerase chain reaction, to produce DNA from an appropriate template nucleic acid.

Once a fragment of the FATP gene is generated by PCR, it can be sequenced, and the sequence of the product can be compared to other DNA sequences, for example, by using the BLAST Network Service at the National Center for Biotechnology Information. The boundaries of the open reading frame can then be identified using semi-specific PCR or other suitable methods such as library screening. Once the 5' initiator methionine codon and the 3' stop codon have been identified, a PCR product encoding the full-length gene can be generated using genomic DNA as a template, with primers complementary to the extreme 5' and 3' ends of the gene or to their flanking sequences. The full-length genes can then be cloned into expression vectors for the production of functional proteins.

The invention also relates to isolated proteins or polypeptides such as those encoded by nucleic acids of the present invention. Isolated proteins can be purified from a natural source or can be made recombinantly. Proteins or polypeptides referred to herein as "isolated" are proteins or polypeptides that exist in a state different from the state in which they exist in cells in which they are normally expressed in an organism, and include proteins or polypeptides obtained by methods described herein, similar methods or other suitable methods, and also include essentially pure proteins or polypeptides, proteins or polypeptides produced by chemical synthesis or by combinations of biological and chemical methods, and recombinant proteins or polypeptides which are isolated. Thus, the term "isolated" as used herein, indicates that the polypeptide in question exists in a physical milieu distinct from that in which it occurs in nature. Thus, "isolated" includes existing in membrane fragments and vesicles membrane fractions, liposomes, lipid bilayers and other artificial membrane systems. An isolated FATP may be substantially isolated with respect to the complex cellular milieu in which it naturally occurs, and may even be purified essentially to homogeneity, for example as determined by PAGE or column chromatography (for example, HPLC), but may also have further cofactors or molecular stabilizers, such as detergents, added to the purified protein to enhance activity. In one embodiment, proteins or polypeptides are isolated to a state at least about 75% pure; more preferably at least about 85% pure, and still more preferably at least about 95% pure, as determined by Coomassie blue staining of proteins on SDS-polyacrylamide gels. Proteins or polypeptides referred to herein as "recombinant" are proteins or polypeptides produced by the expression of recombinant nucleic acids.

In a preferred embodiment, an isolated polypeptide comprising a FATP, a functional portion thereof, or a functional equivalent of the FATP, has at least one function characteristic of a FATP, for example, transport activity, binding function (e.g., a domain which binds to AMP), or antigenic function (e.g., binding of antibodies that also bind to a naturally-occurring FATP, as that function is found in an antigenic determinant). Functional equivalents can have activities that are quantitatively similar to, greater than, or less than, the reference protein. These proteins include, for example, naturally occurring FATPs that can be purified from tissues in which they are produced (including polymorphic or allelic variants), variants (e.g., mutants) of those proteins and/or portions thereof. Such variants include mutants differing by the addition, deletion or substitution of one or more amino acid residues, or modified polypeptides in which one or more residues are modified, and mutants comprising one or more modified residues. Portions or fragments of a FATP can range in size from four amino acid residues to the entire amino acid sequence minus one amino acid.

The isolated proteins of the invention preferably include mammalian fatty acid transport proteins of the FATP family of homologous proteins. In one embodiment, the extent of amino acid sequence similarity between a polypeptide having one of the amino acid sequences shown, for example, in FIGS. 1, 6, 8, 10, 12, 14, 16, 18, 20, or 22 and the respective functional equivalents of these polypeptides is at least about 88%. In other embodiments, the degree of amino acid sequence similarity between a FATP and its respective functional equivalent is at least about 91%, at least about 94%, or at least about 97%.

The polypeptides of the invention also include those FATPs encoded by polynucleotides which are orthologous to those polynucleotides, the sequences of which are described herein in whole or in part. FATPs which are orthologs to those described herein by amino acid sequence, in whole or in part, are, for example fatty acid transport proteins 1–6 of dog, rat chimpanzee, monkey, rabbit, guinea pig, baboon and pig, and are also embodiments of the invention.

To determine the percent identity or similarity of two amino acid sequences or of two nucleic acid sequences, the sequences are aligned for optimal comparison purposes (e.g., gaps can be introduced in one or both of a first and a second amino acid or nucleic acid sequence for optimal alignment, and non-homologous (dissimilar) sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "similarity"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the polypeptides described herein by amino acid sequence. Similarity for a polypeptide is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent is found in Bowie et al., *Science* 247:1306–1310 (1990).

The comparison of sequences and determination of percent identity and similarity between two sequences can be accomplished using a mathematical algorithm. (*Computational Molecular Biology*, Lesk, A. M.,ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereaux, J., eds., M. Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, word length=12 to obtain nucleotide sequences homologous to (with calculatably significant similarity to) the nucleic acid molecules of the invention. BLAST protein searches can be performed with the XBLAST program, score=50, word length=3 to obtain amino acid sequences homologous to the proteins of the invention. To obtain gapped alignments for comparison purposes, Gapped BLAST can be utilized as described in Altschul et al., (*Nucleic Acids Res.* 25 (17):3389–3402 (1997)). When utilizing BLAST and gapped BLAST programs, the default parameters of the respective programs (e.g., XBLAST and NBLAST) can be used. See http://www.ncbi.nlm.nih.gov.

Similarity for nucleotide and amino acid sequences can be defined in terms of the parameters set by the Advanced Blast search available from NCBI (the National Center for Biotechnology Information; see, for Advanced BLAST page, www.ncbi.nlm.nih.gov/cgi-bin/BLAST/nph-newblast?Jform=1). These default parameters, recommended for a query molecule of length greater than 85 amino acid residues or nucleotides have been set as follows: gap existence cost, 11, per residue gap cost, 1; lambda ratio, 0.85. Further explanation of version 2.0 of BLAST can be found on related website pages and in Altschul, S. F. et al., *Nucleic Acids Res.* 25:3389–3402 (1997).

The invention further relates to fusion proteins, comprising a FATP or functional portion thereof (as described above) as a first moiety, linked to second moiety not occurring in the FATP as found in nature. Thus, the second moiety can be, for example, an amino acid, peptide or polypeptide. The first moiety can be in an N-terminal location, C-terminal location or internal to the fusion protein. In one embodiment, the fusion protein comprises a FATP as the first moiety, and a second moiety comprising a linker sequence and an affinity ligand. Fusion proteins can be produced by a variety of methods. For example, a fusion protein can be produced by the insertion of a FATP gene or portion thereof into a suitable expression vector, such as Bluescript SK+/−(Stratagene), pGEX-4T-2 (Pharmacia), pET-24(+) (Novagen), or vectors of similar construction. The resulting construct can be introduced into a suitable host cell for expression. Upon expression, fusion protein can be purified from cells by means of a suitable affinity matrix (See e.g., *Current Protocols in Molecular Biology*, Ausubel, F. M. et al., eds., Vol. 2, pp. 16.4.1–16.7.8, containing supplements up through Supplement 42, 1998).

The invention also relates to enzymatically produced, synthetically produced, or recombinantly produced portions of a fatty acid transport protein. Portions of a FATP can be made which have full or partial function on their own, or which when mixed together (though fully, partially, or nonfunctional alone), spontaneously assemble with one or more other polypeptides to reconstitute a functional protein having at least one function characteristic of a FATP.

Fragments of a FATP can be produced by direct peptide synthesis, for example those using solid-phase techniques (Roberge, J. Y. et al., *Science* 269:202–204 (1995); Merrifield, J., *J Am. Chem. Soc.* 85:2149–2154 (1963)). Protein synthesis can be performed using manual techniques or by automation. Automated synthesis can be carried out using, for instance, an Applied Biosystems 431A Peptide Synthesizer (Perkin Elmer). Various fragments of a FATP can be synthesized separately and combined using chemical methods.

One aspect of the invention is a peptide or polypeptide having the amino acid sequence of a portion of a fatty acid transport protein which is hydrophilic rather than hydrophobic, and ordinarily can be detected as facing the outside of the cell membrane. Such a peptide or polypeptide can be thought of as being an extracellular domain of the FATP, or a mimetic of said extracellular domain. It is known, for example, that a portion of human FATP4 that includes a highly conserved motif is involved in AMP-CoA binding function (Stuhlsatz-Krouper, S. M. et al., *J. Biol. Chem.* 44:28642–28650 (1998)).

The term "mimetic" as used herein, refers to a molecule, the structure of which is developed from knowledge of the structure of the FATP of interest, or one or more portions thereof, and, as such, is able to effect some or all of the functions of a FATP.

Portions of an FATP can be prepared by enzymatic cleavage of the isolated protein, or can be made by chemical synthesis methods. Portions of a FATP can also be made by recombinant DNA methods in which restriction fragments, or fragments that may have undergone further enzymatic processing, or synthetically made DNAs are joined together to construct an altered FATP gene. The gene can be made such that it encodes one or more desired portions of a FATP. These portions of FATP can be entirely homologous to a known FATP, or can be altered in amino acid sequence relative to naturally occurring FATPs to enhance or introduce desired properties such as solubility, stability, or affinity to a ligand. A further feature of the gene can be a sequence encoding an N-terminal signal peptide directed to the plasma membrane.

A polypeptide or peptide comprising all or a portion of a FATP extracellular domain can be used in a pharmaceutical composition. When administered to a mammal by an appropriate route, the polypeptide or peptide can bind to fatty acids and compete with the native FATPs in the membrane of cells, thereby making fewer fatty acid molecules available as substrates for transport into cells, and reducing fatty acid uptake.

Another aspect of the invention relates to a method of producing a fatty acid transport protein, variants or portions thereof, and to expression systems and host cells containing a vector appropriate for expression of a fatty acid transport protein.

Cells that express a FATP, a variant or a portion thereof, or an ortholog of a FATP described herein by amino acid sequence, can be made and maintained in culture, under conditions suitable for expression, to produce protein in the cells for cell-based assays, or to produce protein for isolation. These cells can be procaryotic or eucaryotic. Examples of procaryotic cells that can be used for expression include *Escherichia coli, Bacillus subtilis* and other bacteria. Examples of eucaryotic cells that can be used for expression include yeasts such as *Saccharomyces cerevisiae, Schizosaccharomyces pombe, Pichia pastoris* and other lower eucaryotic cells, and cells of higher eucaryotes such as those from insects and mammals, such as primary cells and cell lines such as CHO, HeLa, 3T3 and BHK cells, COS cells, 293 cells, and Jurkat cells. (See, e.g., Ausubel, F. M. et al., eds. *Current Protocols in Molecular Biology*, Greene Publishing Associates and John Wiley & Sons, Inc., containing Supplements up through Supplement 42, 1998)).

In one embodiment, host cells that produce a recombinant FATP, or a portion thereof, a variant, or an ortholog of a FATP described herein by amino acid sequence, can be made as follows. A gene encoding a FATP, variant or a portion thereof can be inserted into a nucleic acid vector, e.g., a DNA vector, such as a plasmid, phage, cosmid, phagemid, virus, virus-derived vector (e.g., SV40, vaccinia, adenovirus, fowl pox virus, pseudorabies viruses, retroviruses) or other suitable replicon, which can be present in a single copy or multiple copies, or the gene can be integrated in a host cell chromosome. A suitable replicon or integrated gene can contain all or part of the coding sequence for a FATP or variant, operably linked to one or more expression control regions whereby the coding sequence is under the control of transcription signals and linked to appropriate translation signals to permit translation. The vector can be introduced into cells by a method appropriate to the type of host cells (e.g., transfection, electroporation, infection). For expression from the FATP gene, the host cells can be maintained under appropriate conditions (e.g., in the presence of inducer, normal growth conditions, etc.). Proteins or polypeptides thus produced can be recovered (e.g., from the cells, as in a membrane fraction, from the periplasmic space of bacteria, from culture medium) using suitable techniques. Appropriate membrane targeting signals may be incorporated into the expressed polypeptide. These signals may be endogenous to the polypeptide or they may be heterologous signals.

Polypeptides of the invention can be recovered and purified from cell cultures (or from their primary cell source) by well-known methods, including ammonium sulfate or ethanol precipitation, acid extraction, anion or cation exchange chromatography, phosphocellulose chromatography, hydrophobic interaction chromatography, affinity chromatography, hydroxylapatite chromatography and high performance liquid chromatography. Known methods for refolding protein can be used to regenerate active conformation if the polypeptide is denatured during isolation or purification.

In a further aspect of the invention are methods for assessing the transport function of any of the fatty acid transport proteins or polypeptides described herein, including orthologs, and in variations of these, methods for identifying an inhibitor (or an enhancer) of such function and methods for assessing the transport function in the presence of a candidate inhibitor or a known inhibitor.

A variety of systems comprising living cells can be used for these methods. Cells to be used in fatty acid transport assays, and further in methods for identifying an inhibitor or enhancer of this function, express one or more FATPs. Cells for use in cell-based assays described herein can be drawn from a variety of sources, such as isolated primary cells of various organs and tissues wherein one or more FATPs are naturally expressed. In some cases, the cells can be from adult organs, and in some cases, from embryonic or fetal organs, such as heart, lung, liver, skeletal muscle, kidney and the like. Cells for this purpose can also include cells cultured as fragments of organs or in conditions simulating the cell type and/or tissue organization of organs, in which artificial materials may be used as substrates for cell growth. Other types of cells suitable for this purpose include cells of a cell strain or cell line (ordinarily comprising cells considered to be "transformed") transfected to express one or more FATPs.

A further embodiment of the invention is a method for detecting, in a sample of cells, a fatty acid transport protein, a portion or fragment thereof, a fusion protein comprising a FATP or a portion thereof, or an ortholog as described herein, wherein the cells can be, for instance, cells of a tissue, primary culture cells, or cells of a cell line, including cells into which nucleic acid has been introduced. The method comprises adding to the sample an agent that specifically binds to the protein, and detecting the agent specifically bound to the protein. Appropriate washing steps can be added to reduce nonspecific binding to the agent. The agent can be, for example, an antibody, a ligand or a substrate mimic. The agent can have incorporated into it, or have bound to it, covalently or by high affinity non-covalent interactions, for instance, a label that facilitates detection of the agent to which it is bound, wherein the label can be, but is not limited to, a phosphorescent label, a fluorescent label, a biotin or avidin label, or a radioactive label. The means of detection of a fatty acid transport protein can vary, as appropriate to the agent and label used. For example, for an antibody that binds to the fatty acid transport protein, the means of detection may call for binding a second antibody, which has been conjugated to an enzyme, to the antibody which binds the fatty acid transport protein, and detecting the presence of the second antibody by means of the enzymatic activity of the conjugated enzyme.

Similar principles can also be applied to a cell lysate or a more purified preparation of proteins from cells that may comprise a fatty acid transport protein of interest, for example in the methods of immunoprecipitation, immunoblotting, immunoaffinity methods, that in addition to detection of the particular FATP, can also be used in purification steps, and qualitative and quantitative immunoassays. See, for instance, chapters 11 through 14 in *Antibodies: A Laboratory Manual*, E. Harlow and D. Lane, eds., Cold Spring Harbor Laboratory, 1988.

Isolated fatty acid transport protein or, an antigenically similar portion thereof, especially a portion that is soluble, can be used in a method to select and identify molecules which bind specifically to the FATP. Fusion proteins comprising all of, or a portion of, the fatty acid transport protein linked to a second moiety not occurring in the FATP as found in nature, can be prepared for use in another embodiment of the method. Suitable fusion proteins for this purpose include those in which the second moiety comprises an affinity ligand (e.g., an enzyme, antigen, epitope). FATP fusion proteins can be produced by the insertion of a gene encoding the FATP or a variant thereof, or a suitable portion of such gene into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix.

In one embodiment, the fusion protein can be immobilized on a suitable affinity matrix under conditions sufficient to bind the affinity ligand portion of the fusion protein to the matrix, and is contacted with one or more candidate binding agents (e.g., a mixture of peptides) to be tested, under conditions suitable for binding of the binding agents to the FATP portion of the bound fusion protein. Next, the affinity matrix with bound fusion protein can be washed with a suitable wash buffer to remove unbound candidate binding agents and non-specifically bound candidate binding agents. Those agents which remain bound can be released by contacting the affinity matrix with fusion protein bound thereto with a suitable elution buffer. Wash buffer can be formulated to permit binding of the fusion protein to the affinity matrix, without significantly disrupting binding of specifically bound binding agents. In this aspect, elution buffer can be formulated to permit retention of the fusion protein by the affinity matrix, but can be formulated to interfere with binding of the candidate binding agents to the target portion of the fusion protein. For example, a change in the ionic strength or pH of the elution buffer can lead to release of specifically bound agent, or the elution buffer can comprise a release component or components designed to disrupt binding of specifically bound agent to the target portion of the fusion protein.

Immobilization can be performed prior to, simultaneous with, or after, contacting the fusion protein with candidate binding agent, as appropriate. Various permutations of the method are possible, depending upon factors such as the candidate molecules tested, the affinity matrix-ligand pair selected, and elution buffer formulation. For example, after the wash step, fusion protein with binding agent molecules bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with the candidate agent bound thereto. Bound agent molecules can then be released from the fusion protein or its cleavage product by an appropriate method, such as extraction.

One or more candidate binding agents can be tested simultaneously. Where a mixture of candidate binding agents is tested, those found to bind by the foregoing processes can be separated (as appropriate) and identified by suitable methods (e.g., PCR, sequencing, chromatography). Large libraries of candidate binding agents (e.g., peptides, RNA oligonucleotides) produced by combinatorial chemical synthesis or by other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rutter, W. J. et al. U.S. Pat. No. 5,010,175; Huebner, V. D. et al., U.S. Pat. No. 5,182,366; and Geysen, H. M., U.S. Pat. No. 4,833,092). Random sequence RNA libraries (see Ellington, A. D. et al., *Nature* 346:818–822 (1990); Bock, L. C. et al., *Nature* 355:584–566 (1992); and Szostak, J. W., *Trends in Biochem. Sci.* 17:89–93 (March, 1992)) can also be screened according to the present method to select RNA molecules which bind to a target FATP or FATP fusion protein. Where binding agents selected from a combinatorial library by the present method carry unique tags, identification of individual biomolecules by chromatographic methods is possible. Where binding agents do not carry tags, chromatographic separation, followed by mass spectrometry to ascertain structure, can be used to identify binding agents selected by the method, for example.

The invention also comprises a method for identifying an agent which inhibits interaction between a fatty acid transport protein and a ligand of said protein. The FATP can be one described by amino acid sequence herein, a portion or fragment thereof, a variant thereof, or an ortholog thereof, or a FATP fusion protein. Here, a ligand can be, for instance, a substrate, or a substrate mimic, an antibody, or a compound, such as a peptide, that binds with specificity to a site on the protein. The method comprises combining, not limited to a particular order, the fatty acid protein, the ligand of the protein, and a candidate agent to be assessed for its ability to inhibit interaction between the protein and the ligand, under conditions appropriate for interaction between the protein and the ligand (e.g., pH, salt, temperature conditions conducive to appropriate conformation and molecular interactions); determining the extent to which the protein and ligand interact; and comparing (1) the extent of protein-ligand interaction in the presence of candidate agent with (2) the extent of protein-ligand interaction in the absence of candidate agent, wherein if (1) is less than (2), then the candidate agent is one which inhibits interaction between the protein and the ligand.

The method can be facilitated, for example, by using an experimental system which employs a solid support (column chromatography matrix, wall of a plate, microtiter wells, column pore glass, pins to be submerged in a solution, beads, etc.) to which the protein can be attached. Accordingly, in one embodiment, the protein can be fixed to a solid phase directly or indirectly, by a linker. The candidate agent to be tested is added under conditions conducive for interaction and binding to the protein. The ligand is added to the solid phase system under conditions appropriate for binding. Excess ligand is removed, as by a series of washes done under conditions that do not disrupt protein-ligand interactions. Detection of bound ligand can be facilitated by using a ligand that carries a label (e.g., fluorescent, chemiluminescent, radioactive). In a control experiment, protein and ligand are allowed to interact in the absence of any candidate agent, under conditions otherwise identical to those used for the "test" conditions where candidate inhibiting agent is present, and any washes used in the test conditions are also used in the control. The extent to which ligand binds to the protein in the presence of candidate agent is compared to the extent to which ligand binds to the protein in the absence of the candidate agent. If the extent to which interaction of the protein and the ligand occurs is less in the presence of the candidate agent than in the absence of the candidate agent, the candidate agent is an agent which inhibits interaction between the protein and the ligand of the protein.

In a further embodiment, an inhibitor (or an enhancer) of a fatty acid transport protein can be identified. The method comprises steps which are, or are variations of the following: contacting the cells with fatty acid, wherein the fatty acid can be labeled for convenience of detection; contacting a first aliquot of the cells with an agent being tested as an inhibitor (or enhancer) of fatty acid uptake while maintaining a second aliquot of cells under the same conditions but without contact with the agent; and measuring (e.g., quantitating) fatty acid in the first and second aliquots of cells; wherein a lesser quantity of fatty acid in the first aliquot compared to that in the second aliquot is indicative that the agent is an inhibitor of fatty acid uptake by a fatty acid transport protein. A greater quantity of fatty acid in the first aliquot compared to that in the second aliquot is indicative that the agent is an enhancer of fatty acid uptake by a fatty acid transport protein.

A particular embodiment of identifying an inhibitor or enhancer of fatty acid transport function employs the above steps, but also employs additional steps preceding those given above: introducing into cells of a cell strain or cell line ("host cells" for the intended introduction of, or after the introduction of, a vector) a vector comprising a fatty acid transport protein gene, wherein expression of the gene can be regulatable or constitutive, and providing conditions to the host cells under which expression of the gene can occur.

The terms "contacting" and "combining" as used herein in the context of bringing molecules into close proximity to each other, can be accomplished by conventional means. For example, when referring to molecules that are soluble, contacting is achieved by adding the molecules together in a solution. "Contacting" can also be adding an agent to a test system, such as a vessel containing cells in tissue culture.

The term "inhibitor" or "antagonist", as used herein, refers to an agent which blocks, diminishes, inhibits, hinders, limits, decreases, reduces, restricts or interferes with fatty acid transport into the cytoplasm of a cell, or alternatively and additionally, prevents or impedes the cellular effects associated with fatty acid transport. The term "enhancer" or "agonist", as used herein, refers to an agent which augments, enhances, or increases fatty acid transport into the cytoplasm of a cell. An antagonist will decrease fatty acid concentration, fatty acid metabolism and byproduct levels in the cell, leading to phenotypic and molecular changes.

In order to produce a "host cell" type suitable for fatty acid uptake assays and for assays derived therefrom for identifying inhibitors or enhancers thereof, a nucleic acid vector can be constructed to comprise a gene encoding a fatty acid transport protein, for example, human FATP2, FATP3, FATP4, FATP5, FATP6, a mutant or variant thereof, an ortholog of the human proteins, such as mouse orthologs or orthologs found in other mammals, or a FATP family protein of origin in an organism other than a mammal. The gene of the vector can be regulatable, such as by the placement of the gene under the control of an inducible or repressible promoter in the vector (e.g., inducible or repressible by a change in growth conditions of the host cell harboring the vector, such as addition of inducer, binding or functional removal of repressor from the cell millieu, or change in temperature) such that expression of the FATP gene can be turned on or initiated by causing a change in growth conditions, thereby causing the protein encoded by the gene to be produced, in host cells comprising the vector, as a plasma membrane protein. Alternatively, the FATP gene can be constitutively expressed.

A vector comprising an FATP gene, such as a vector described herein, can be introduced into host cells by a means appropriate to the vector and to the host cell type. For example, commonly used methods such as electroporation, transfection, for instance, transfection using $CaCl_2$, and transduction (as for a virus or bacteriophage) can be used. Host cells can be, for example, mammalian cells such as primary culture cells or cells of cell lines such as COS cells, 293 cells or Jurkat cells. Host cells can also be, in some cases, cells derived from insects, cells of insect cell lines, bacterial cells, such as *E. coli*, or yeast cells, such as *S. cerevisiae*. It is preferred that the fatty acid transport protein whose function is to be assessed, with or without a candidate inhibitor or enhancer, be produced in host cells whose ancestor cells originated in a species related to the species of origin of the FATP gene encoding the fatty acid transport protein. For example, it is preferable that tests of function or of inhibition or enhancement of a mammalian FATP be carried out in host mammalian cells producing the FATP, rather than bacterial cells or yeast cells.

Host cells comprising a vector comprising a regulatable FATP gene can be treated so as to allow expression of the FATP gene and production of the encoded protein (e.g., by contacting the cells with an inducer compound that effects transcription from an inducible promoter operably linked to the FATP gene).

The test agent (e.g., an agonist or antagonist) is added to the cells to be used in a fatty acid transport assay, in the presence or absence of test agent, under conditions suitable for production and/or maintenance of the expressed FATP in a conformation appropriate for association of the FATP with test agent and substrate. For example, conditions under which an agent is assessed, such as media and temperature requirements, can, initially, be similar to those necessary for transport of typical fatty acid substrates across the plasma membrane. One of ordinary skill in the art will know how to vary experimental conditions depending upon the biochemical nature of the test agent. The test agent can be added to the cells in the presence of fatty acid, or in the absence of fatty acid substrate, with the fatty acid substrate being added following the addition of the test agent. The concentration at which the test agent can be evaluated can be varied, as appropriate, to test for an increased effect with increasing concentrations.

Test agents to be assessed for their effects on fatty acid transport can be any chemical (element, molecule, compound), made synthetically, made by recombinant techniques or isolated from a natural source. For example, test agents can be peptides, polypeptides, peptoids, sugars, hormones, or nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates of cells, bacterial, animal or plant, or can be the cell lysates themselves. Presentation of test compounds to the test system can be in either an isolated form or as mixtures of compounds, especially in initial screening steps.

Thus, the invention relates to a method for identifying agents which alter fatty acid transport, the method comprising providing the test agent to the cell (wherein "cell" includes the plural, and can include cells of a cell strain, cell line or culture of primary cells or organ culture, for example), under conditions suitable for binding to its target, whether to the FATP itself or to another target on or in the cell, wherein the transformed cell comprises a FATP.

In greater detail, to test one or more agents or compounds (e.g., a mixture of compounds can conveniently be screened initially) for inhibition of the transport function of a fatty acid transport protein, the agent(s) can be contacted with the cells. The cells can be contacted with a labeled fatty acid. The fatty acid can be, for example, a known substrate of the fatty acid transport protein such as oleate or palmitate. The fatty acid can itself be labeled with a radioactive isotope, (e.g., $^3$H or $^{14}$C) or can have a radioactively labeled adduct attached. In other variations, the fatty acid can have chemically attached to it a fluorescent label, or a substrate for an enzyme occurring within the cells, wherein the substrate yields a detectable product, such as a highly colored or fluorescent product. Addition of candidate inhibitors and labeled substrate to the cells comprising fatty acid transport protein can be in either order or can be simultaneous.

A second aliquot of cells, which can be called "control" cells (a "first" aliquot of cells can be called "test" cells), is treated, if necessary (as in the case of transformed "host" cells), so as to allow expression of the FATP gene, and is contacted with the labeled substrate of the fatty acid transport protein. The second aliquot of cells is not contacted with one or more agents to be tested for inhibition of the transport function of the protein produced in the cells, but is otherwise kept under the same culture conditions as the first aliquot of cells.

In a further step of a method to identify inhibitors of a fatty acid transport protein, the labeled fatty acid is measured in the first and second aliquots of cells. A preliminary step of this measurement process can be to separate the external medium from the cells so as to be able to distinguish the labeled fatty acid external to the cells from that which has been transported inside the cells. This can be accomplished, for instance, by removing the cells from their growth container, centrifuging the cell suspension, removing the supernatant and performing one or more wash steps to extensively dilute the remaining medium which may contain labeled fatty acid. Detection of the labeled fatty acid can be by a means appropriate to the label used. For example, for a radioactive label, detection can be by scintillation counting of appropriately prepared samples of cells (e.g., lysates or protein extracts); for a fluorescent label, by measuring fluorescence in the cells by appropriate instrumentation.

If a compound tested as a candidate inhibitor of transport function causes the test cells to have less labeled fatty acid detected in the cells than that detected in the control cells, then the compound is an inhibitor of the fatty acid transport protein. Procedures analogous to those above can be devised for identifying enhancers (agonists of FATPs) of fatty acid transport function wherein if the test cells contain more labeled fatty acid than that detected in the control cells, or if the fatty acid is taken up at a higher rate, then the compound being tested can be concluded to be an enhancer of the fatty acid transport protein.

Another assay to determine whether an agent is an inhibitor (or enhancer) of fatty acid transport employs animals, one or more of which are administered the agent, and one or more of which are maintained under similar conditions, but are not administered the agent. Both groups of animals are given fatty acids (e.g., orally, intravenously, by tube inserted into stomach or intestine), and the fatty acids taken up into a bodily fluid (e.g., serum) or into an organ or tissue of interest are measured from comparable samples taken from each group of animals. The fatty acids may carry a label (e.g., radioactive) to facilitate detection and quantitation of fatty acids taken up into the fluid or tissue being sampled. This type of assay can be used alone or can be used in addition to in vitro assays of a candidate inhibitor or enhancer.

An agent determined to be an inhibitor (or enhancer) of FATP function, such as fatty acid binding and/or fatty acid uptake, can be administered to cells in culture, or in vivo, to a mammal (e.g. human) to inhibit (or enhance) FATP function. Such an agent may be one that acts directly on the FATP (for example, by binding) or can act on an intermediate in a biosynthetic pathway to produce FATP, such as transcription of the FATP gene, processing of the mRNA, or translation of the mRNA. An example of such an agent is antisense oligonucleotide.

Cell-free assays can also be used to measure the transport of fatty acids across a membrane, and therefor also to assess a test treatment or test agent for its effect on the rate or extent of fatty acid transport. An isolated FATP, for example in the presence of a detergent that preserves the native 3-dimensional structure of the FATP, or partially purified FATP, can be used in an artificial membrane system typically used to preserve the native conformation and activity of membrane proteins. Such systems include liposomes, artificial bilayers of phospholipids, isolated plasma membrane such as cell membrane fragments, cell membrane fractions, or cell membrane vesicles, and other systems in which the FATP can be properly oriented within the membrane to have transport activity. Assays for transport activity can be performed using methods analogous to those that can be used in cells engineered to predominantly express one FATP whose function is to be measured. A labeled (e.g., radioactively labeled) fatty acid substrate can be incubated with one side of a bilayer or in a suspension of liposomes constructed to integrate a properly oriented FATP. The accumulation of fatty acids with time can be measured, using appropriate means to detect the label (e.g., scintillation counting of medium on each side of the bilayer, or of the contents of liposomes isolated from the surrounding medium). Assays such as these can be adapted to use for the testing of agents which might interact with the FATP to produce an inhibitory or an enhancing effect on the rate or extent of fatty acid transport. That is, the above-described assay can be done in the presence or absence of the agent to be tested, and the results compared.

Another embodiment of the invention is a method for inhibiting fatty acid uptake in a mammal (e.g., a human), comprising administering to the mammal a therapeutically effective amount of an inhibitor of the transport function of one or more of the fatty acid transport proteins, thereby decreasing fatty acid uptake by cells comprising the fatty acid protein(s). Where it is desirable to reduce the uptake of fatty acids, for example, in the treatment of chronic obesity or as a part of a program of weight control or hyperlipidemia control in a human, one or more inhibitors of one or more of the fatty acid transport proteins can be administered in an effective dose, and by an effective route, for example, orally, or by an indwelling device. The inhibitor can be one identified by methods described herein, or can be one that is, for instance, structurally related to an inhibitor identified by methods described herein (e.g., having chemical adducts to better stabilize or solubilize the inhibitor). The invention further relates to compositions comprising inhibitors of fatty acid uptake in a mammal, which may further comprise pharmaceutical carriers suitable for administration to a subject mammal, such as sterile solubilizing or emulsifying agents.

A further embodiment of the present invention is a method of enhancing or increasing fatty acid uptake, such as enhancing or increasing LCFA uptake in the liver (e.g., by an enhancer of FATP5 transport activity to treat acute liver failure) or in the kidney (e.g., by an enhancer of FATP2 transport activity to treat kidney failure). In this embodiment, a therapeutically effective amount of an enhancer of the transport function of one or more of the fatty acid transport proteins can be administered to a mammalian subject, with the result that fatty acid uptake is enhanced. In this embodiment, one or more enhancers of one or more of fatty acid transport proteins is administered in an effective dose and by a route (e.g., orally or by a device, such as an indwelling catheter or other device) which can deliver doses to the gut. The enhancer of FATP function (e.g., an enhancer of FATP4 function) can be identified by methods described herein or can be one that is structurally similar to an enhancer identified by methods described herein.

The invention further relates to antibodies that bind to an isolated or recombinant fatty acid transport protein of the FATP family, including portions of antibodies, which can specifically recognize and bind to one or more FATPs. The antibodies and portions thereof of the invention include those which bind to one or more FATPs of mouse or other mammalian species. In a preferred embodiment, the antibodies specifically bind to a naturally occurring FATP of humans. The antibodies can be used in methods to detect or to purify a protein of the present invention or a portion thereof by various methods of immunoaffinity chromatography, to inhibit the function of a protein in a method of therapy, or to selectively inactivate an active site, or to study other aspects of the structure of these proteins, for example.

The antibodies of the present invention can be polyclonal or monoclonal. The term antibody is intended to encompass both polyclonal and monoclonal antibodies. Antibodies of the present invention can be raised against an appropriate immunogen, including proteins or polypeptides of the present invention, such as an isolated or recombinant FATP1, FATP2, FATP3, FATP4, FATP5, FATP6, mtFATP, ceFATPa, mgFATP, chFATP, dmFATP, drFATP or portions of any of the foregoing, or synthetic molecules, such as synthetic peptides (e.g., conjugated to a suitable carrier). Preferred embodiments are antibodies that bind to any of the following:, hsFATP2, hsFATP3, hsFATP4, hsFATP5 or hsFATP6 polypeptides. The immunogen can be a polypeptide comprising a portion of a FATP and having at least one function of a fatty acid transport protein, as described herein.

The term antibody is also intended to encompass single chain antibodies, chimeric, humanized or primatized (CDR-grafted) antibodies and the like, as well as chimeric or CDR-grafted single chain antibodies, comprising portions from more than one species. For example, the chimeric antibodies can comprise portions of proteins derived from two different species, joined together chemically by conventional techniques or prepared as a single contiguous protein using genetic engineering techniques (e.g., DNA encoding the protein portions of the chimeric antibody can be expressed to produce a contiguous protein chain. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., U.S. Pat. No. 5,585,089; and Queen et al., European Patent No. EP 0 451 216 B1. See also, Newman, R. et al., *BioTechnology*, 10:1455–1460 (1992), regarding primatized antibody, and Ladner et al., U.S. Pat. No. 4,946,778 and Bird, R. E. et al., *Science*, 242:423–426 (1988) regarding single chain antibodies.)

Whole antibodies and biologically functional fragments thereof are also encompassed by the term antibody. Biologically functional antibody fragments which can be used include those fragments sufficient for binding of the antibody fragment to a FATP to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen (for example, whole cells comprising FATP on the cell surface or purified FATP), and polyclonal and monoclonal antibody production can be performed using any suitable technique. A variety of methods have been described (See e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); Chapter 11 In *Current Protocols In Molecular Biology*, Vol. 2 (containing supplements up through Supplement 42, 1998), Ausubel, F. M. et al., eds., (John Wiley & Sons: New York, N.Y.)). Generally, a hybridoma can be produced by fusing a suitable immortal cell line (e.g., a myeloma cell line such as SP2/0) with antibody producing cells. The antibody producing cells, preferably those obtained from the spleen or lymph nodes, can be obtained from animals immunized with the antigen of interest. Immunization of animals can be by introduction of whole cells comprising fatty acid transport protein on the cell surface. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies (including human antibodies) of the requisite specificity can used, including, for example, methods which select recombinant antibody from a library (e.g., Hoogenboom et al., WO 93/06213; Hoogenboom et al., U.S. Pat. No. 5,565,332; WO 94/13804, published Jun. 23, 1994; and Dower, W. J. et al., U.S. Pat. No. 5,427,908), or which rely upon immunization of transgenic animals (e.g., mice) capable of producing a full repertoire of human antibodies (see e.g., Jakobovits et al., *Proc. Natl. Acad. Sci. USA*, 90: 2551–2555 (1993); Jakobovits et al., *Nature*, 362:255–258 (1993); Lonberg et al., U.S. Pat. No. 5,569,825; Lonberg et al., U.S. Pat. No. 5,545,806; Surani et al., U.S. Pat. No. 5,545,807; and Kucherlapati, R. et al., European Patent No. EP 0 463 151 B1).

An agent can be directed to the liver of a mammal, as FATP5 is expressed in liver but not in other tissue types. A targeting vehicle which specifically binds to FATP5 can be conjugated to a drug for delivery of the drug to the liver, such as a drug to treat hepatitis, Wilson's disease, lipid storage diseases and liver cancer. Targeting vehicles specific to FATP5 can be used in studying tissue samples in vitro.

The invention also relates to compositions comprising a modulator of FATP function. The term "modulate" as used herein refers to the ability of a molecule to alter the function of another molecule. Thus, modulate could mean, for example, inhibit, antagonize, agonize, upregulate, downregulate, induce, or suppress. A modulator has the capability of altering function of its target. Such alteration can be accomplished at any stage of the transcription, translation, expression or function of the protein, so that, for example, modulation of a target gene can be accomplished by modulation of the DNA or RNA encoding the protein, and the protein itself.

Antagonists or agonists (inhibitors or enhancers) of the FATPs of the invention, antibodies that bind a FATP, or mimetics of a FATP can be employed in combination with a non-sterile or sterile carrier or carriers for use with cells, tissues or organisms, such as a pharmaceutical carrier suitable for administration to a mammalian subject. Such compositions comprise, for instance, a media additive or a therapeutically effective amount of an inhibitor or enhancer compound to be identified by an assay of the invention and a pharmaceutically acceptable carrier or excipient. Such carriers may include, but are not limited to, saline, buffered saline, dextrose, water, ethanol, surfactants, such as glycerol, excipients such as lactose and combinations thereof. The formulation can be chosen by one of ordinary skill in the art to suit the mode of administration. The chosen route of administration will be influenced by the predominant tissue or organ location of the FATP whose function is to be inhibited or enhanced. For example, for affecting the function of FATP4, a preferred administration can be oral or through a tube inserted into the stomach (e.g., direct stomach tube or nasopharyngeal tube), or through other means to accomplish delivery to the small intestine. The invention further relates to diagnostic and pharmaceutical packs and kits comprising one or more containers filled with one or more of the ingredients of the aforementioned compositions of the invention.

Compounds of the invention which are FATPs, FATP fusion proteins, FATP mimetics, FATP gene-specific antisense poly- or oligonucleotides, inhibitors or enhancers of a FATP may be employed alone or in conjunction with other compounds, such as therapeutic compounds. The pharmaceutical compositions may be administered in any effective, convenient manner, including administration by topical, oral, anal, vaginal, intravenous, intraperitoneal, intramuscular, subcutaneous, intranasal, transdermal or intradermal routes, among others. In therapy or as a prophylactic, the active agent may be administered to an individual as an injectable composition, for example as a sterile aqueous dispersion, preferably isotonic.

Alternatively, the composition may be formulated for topical application, for example, in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions.

In addition, the amount of the compound will vary depending on the size, age, body weight, general health, sex, and diet of the host, and the time of administration, the biological half-life of the compound, and the particular characteristics and symptoms of the disorder to be treated. Adjustment and manipulation of established dose ranges are well within the ability of those of skill in the art.

A further aspect of the invention is a method to identify a polymorphism, or the presence of an alternative or variant allele of a gene in the genome of an organism (of interest here, genes encoding FATPs). As used herein, polymorphism refers to the occurrence of two or more genetically determined alternative sequences or alleles in a population. A polymorphic locus may be as small as a base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified alleleic form, or the most frequently occurring form can be arbitrarily designated as the reference (usually, "wildtype") form, and other allelic forms are designated as alternative (sometimes, "mutant" or "variant"). Dipolid organisms may be homozygous or heterozygous for allelic forms.

An "allele" or "allelic sequence" is an alternative form of a gene which may result from at least one mutation in the nucleotide sequence. Alleles may result in altered mRNAs or polypeptides whose structure or function may or may not be altered. Any given gene may have none, one, or many allelic forms (polymorphism). Common mutational changes which give rise to alleles are generally ascribed to natural deletions, additions, or substitutions of nucleotides. Each of these types of changes may occur alone, or in combination with the others, one or more times in a given sequence.

Several different types of polymorphisms have been reported. A restriction fragment length polymorphism (RFLP) is a variation in DNA sequence that alters the length of a restriction fragment (Botstein et al., *Am. J. Hum. Genet.* 32:314–331 (1980)). The restriction fragment length polymorphism may create or delete a restriction site, thus changing the length of the restriction fragment. RFLPs have been widely used in human and animal genetic analyses (see WO 90/13668; WO 90/11369; Donis-Keller, *Cell* 51:319–337 (1987); Lander et al., *Genetics* 121:85–99 (1989)). When a heritable trait can be linked to a particular RFLP, the presence of the RFLP in an individual can be used to predict the likelihood that the individual will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307:113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs (short tandem repeats) and VNTRs (variable number tandem repeats). Some single nucleotide polymorphisms occur in protein-coding sequences, in which case, one of the polymorphic forms may give rise to the expression of a defective or other variant protein and, potentially, a genetic disease. Other single nucleotide polymorphisms occur in noncoding regions. Some of these polymorphisms may also result in defective protein expression (e.g., as a result of defective splicing). Other single nucleotide polymorphisms have no phenotypic effects.

Many of the methods described below require amplification of DNA from target samples and purification of the amplified products. This can be accomplished by PCR, for instance. See generally, *PCR Technology, Principles and Applications for DNA Amplification* (ed. H. A. Erlich), Freeman Press, New York, N.Y., 1992; *PCR Protocols: A Guide to Methods and Applications* (eds. Innis, et al.), Academic Press, San Diego, Calif., 1990; Mattila et al., *Nucleic Acids Res.* 19:4967 (1991); Eckert et al., *PCR Methods and Applications* 1:17 (1991); *PCR* (eds. McPherson et al., IRS Press, Oxford); and U.S. Pat. No. 4,683,202.

Other suitable amplification methods include the ligase chain reaction (LCR) (see Wu and Wallace, *Genomics* 4:560 (1989); Landegren et al., *Science* 241:1077 (1988)), transcription amplification (Kwoh et al., *Proc. Natl. Acad. Sci. USA* 86:1173 (1989), self-sustained sequence replication (Guatelli et al., *Proc. Natl. Acad. Sci. USA* 87:1874 (1990), and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Another aspect of the invention is a method for detecting a variant allele of a human FATP gene, comprising preparing amplified, purified FATP DNA from a reference human and amplified, purified, FATP DNA from a "test" human to be compared to the reference as having a variant allele, using the same or comparable amplification procedures, and determining whether the reference DNA and test DNA differ in DNA sequence in the FATP gene, whether in a coding or a noncoding region, wherein, if the test DNA differs in sequence from the reference DNA, the test DNA comprises a variant allele of a human FATP gene. The following is a discussion of some of the methods by which it can be determined whether the reference FATP DNA and test FATP DNA differ in sequence.

Direct Sequencing. The direct analysis of the sequence of variant alleles of the present invention can be accomplished using either the dideoxy chain termination method or the Maxam and Gilbert method (see Sambrook et al., *Molecular Cloning: A Laboratory Manual*, 2nd ed., Cold Spring Harbor Press, New York 1989; Zyskind et al., *Recombinant DNA Laboratory Manual*, Acad. Press, 1988)).

Denaturing Gradient Gel Electrophoresis. Amplification products generated using the polymerase chain reaction can be analyzed by the use of denaturing gradient gel eletrophoresis. Different alleles can be identified based on the different sequence-dependent strand dissociation properties and electrophoretic migration of DNA in solution (chapter 7 in Erlich, ed. *PCR Technology, Principles and Applications for DNA Amplification*, W. H. Freeman and Co., New York, 1992).

Single-strand Conformation Polymorphism Analysis. Alleles of target sequences can be differentiated using single-strand conformation polymorphism analysis, which identifies base differences by alteration in electrophoretic migration of single stranded PCR products, as described in Orita et al., *Proc. Natl. Acad. Sci. USA* 86:2766–2770 (1989). Amplified PCR products can be generated as described above, and heated or otherwise denatured, to form single-stranded amplification products. Single-stranded nucleic acids may refold or form secondary structures which are partially dependent on the base sequence. The different electrophoretic mobilities of single-stranded amplification products can be related to base-sequence differences between alleles of target sequences.

Detection of Binding by Protein That Binds to Mismatches. Amplified DNA comprising the FATP gene or portion of the gene of interest from genomic DNA, for example, of a normal individual, is prepared, using primers designed on the basis of the DNA sequences provided herein. Amplified DNA is also prepared, in a similar manner, from genomic DNA of an individual to be tested for bearing a distinguishable allele. The primers used in PCR carry different labels, for example, primer 1 with biotin, and primer 2 with $^{32}$P. Unused primers are separated form the PCR products, and the products are quantitated. The heteroduplexes are used in a mismatch detection assay using immobilized mismatch binding protein (MutS) bound to nitrocellulose. The presence of biotin-labeled DNA wherein mismatched regions are bound to the nitrocellulose via MutS protein, is detected by visualizing the binding of streptavidin to biotin. See WO 95/12689. MutS protein has also been used in the detection of point mutations in a gel-mobility-shift assay (Lishanski, A. et al., *Proc. Natl. Acad. Sci. USA* 91:2674–2678 (1994)).

Other methods, such as those described below, can be used to distinguish a FATP allele from a reference allele, once a particular allele has been characterized as to DNA sequence.

Allele-specific probes. The design and use of allele-specific probes for analyzing polymorphims is described by e.g., Saiki et al., *Nature* 324:163–166 (1986); Dattagupta, EP 235,726, Saiki, WO 89/11548. Allele-specific probes can be designed so that they hybridize to a segment of a target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Allele-specific Primers. An allele-specific primer hybridizes to a site on target DNA overlapping a polymorphism, and only primes amplification of an allelic form to which the primer exhibits perfect complementarity. See Gibbs, *Nucleic Acid Res.* 17:2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

Gene Chips. Allelic variants can also be identified by hybridization to nucleic acids immobilized on solid supports (gene chips), as described, for example, in WO 95/11995 and U.S. Pat. No. 5,143,854, both of which are incorporated herein by reference. WO 95/11995 describes subarrays that are optimized for detection of a characterized variant allele. Such a subarray contains probes designed to be complementary to a second reference sequence, which is an allelic variant of the first reference sequence.

The present method is illustrated by the following examples, which are not intended to be limiting in any way.

EXEMPLIFICATION

To identify novel FATPs we searched the NCBI expressed sequence tag (EST) database using the FATP protein sequence. This strategy led to the identification of more than 50 murine EST sequences which could be assembled into five distinct continguous DNA sequences (contigs). One of these contigs represented the previously cloned FATP (FATP1). Another was identified as the mouse homologue of the previously cloned rat very long chain acyl Co-A synthase (FATP2). The other three contigs represented new genes (FATP3 to 5). Screening of mouse fetal 10.5 day embryo and adult liver cDNA libraries resulted in full length clones for FATP2 and FATP5 and nearly complete sequences for FATP3 and FATP4. Human homologues for each of the murine genes were also identified. Additionally, a sixth human gene was present in the EST database. It is not clear if this gene does not occur in the mouse or is merely not present in the mouse database. Sequences conserved among the 5 murine FATP genes were used to carryout database searches to include other organisms. This resulted in identification of the previously described FATP homologue in S. cerevisiae and of novel genes in fugu, C. elegans, Mycobacterium tuberculosis, Deinoccococcus radiodurans, and Archaebacterium fulgidus.

In order to compare FATPs from different species we propose that the FATP genes be given a species specific prefix (mm, mus musculus; hs, homo sapiens; mt, mycobacterium tuberculosis; ce caenorbiditis elegans) and numbered such that mammalian homologues in different species share the same number but differ in their prefix. Thus, the gene cloned by Schaeffer and Lodish would be designated mmFATP1, the mouse homologue of the rat VLACS would be designated mmFATP2, and the remaining genes would be numbered successively, starting with mmFATP2. For multiple fatty acid transporters in a single non-mammalian species for which the corresponding mammalian FATP counterpart cannot be identified we suggest a small letter suffix, e.g. ceFATPa and ceFATPb for the two C. elegans genes. Faergeman et al. have described three regions of very strong sequence conservation between the yeast FATP gene and the mouse FATP gene. The sequences of mmFATP1, mmFATP5, ceFATPa, scFATP, and mtFATP were compared over a 360 amino acid stretch which includes these regions. The DNAstar program was used to determine a consensus sequence for this region and align these genes with that sequence (FIG. 1). Over this interval, the mouse genes are approximately 70% identical to the consensus, the yeast and C. elegans genes 60% identical and the mycobacterial gene 55% identical. When compared to the database, only one region shows homology to other proteins. This small stretch of amino acids (underlined in FIG. 1) is found in AMP binding proteins. The other regions in this sequence including stretches of amino acids over 90% identical from mycobacteria to mice are not found in any other class of proteins. This FATP "signature sequence" of 360 amino acids was used to construct a phylogenetic tree (FIG. 2). As expected, mFATP2 is closer to mmFATP2 than hsFATP2. The fugu gene seems to be most homologous to mmFATP1 and the C. elegans genes are most closely related to each other. Very surprisingly, the mycobacterial gene seems to be more similar to mice genes than to the putative FATPs of other lower organisms.

Figures 3A, 3B, 3C, 3D, 3E:
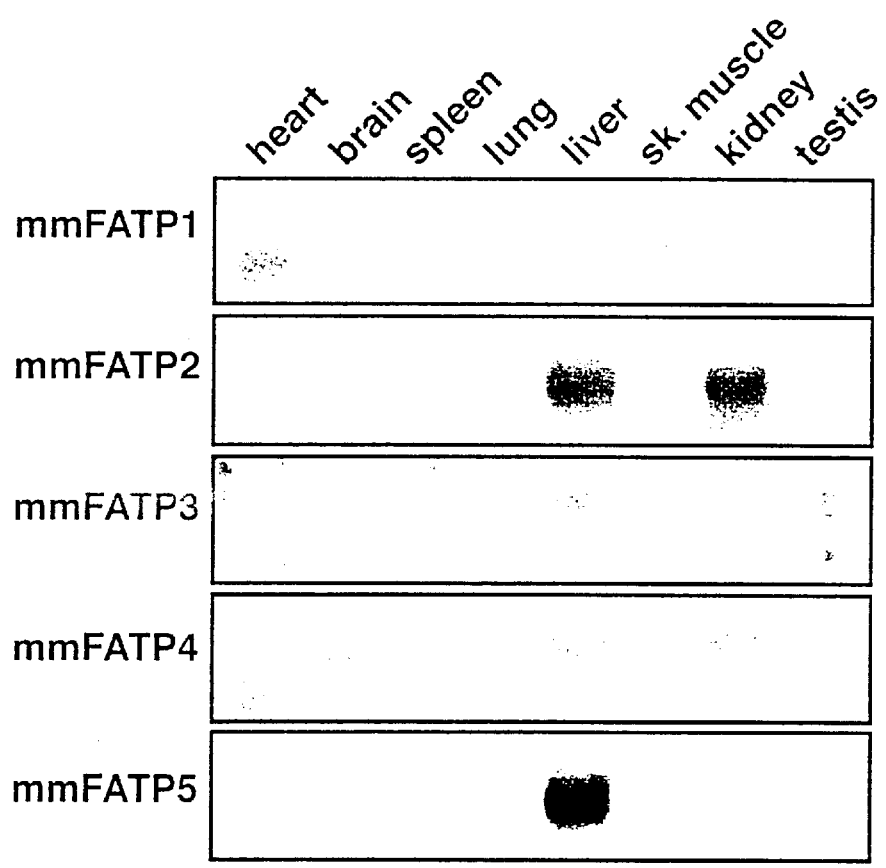
FIGS. 3A–3E are photographs of the results of northern analysis of issue distribution of the murine FATP genes.
Figure 4A:
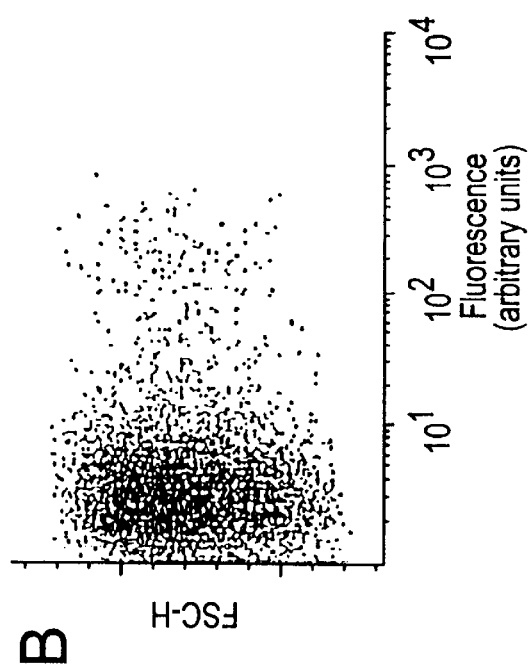
FIGS. 4A–4D shows results of FACs analysis of uptake of a BODIPY-labeled analog of a long chain fatty acid by COS cells transiently transfected with mmFATP1, mmFTP2, or mmFATP5 (FIGS. 4B, 4C, and 4D, respectively) and by control (untransfected COS cells.
Figure 4B:
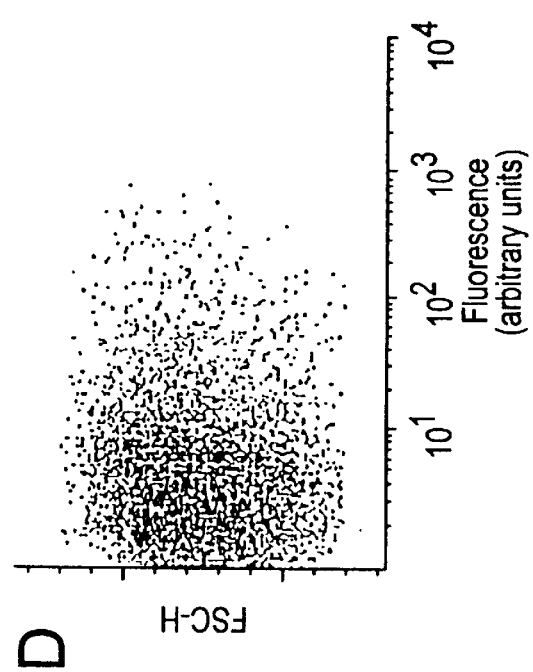
Figure 4C:
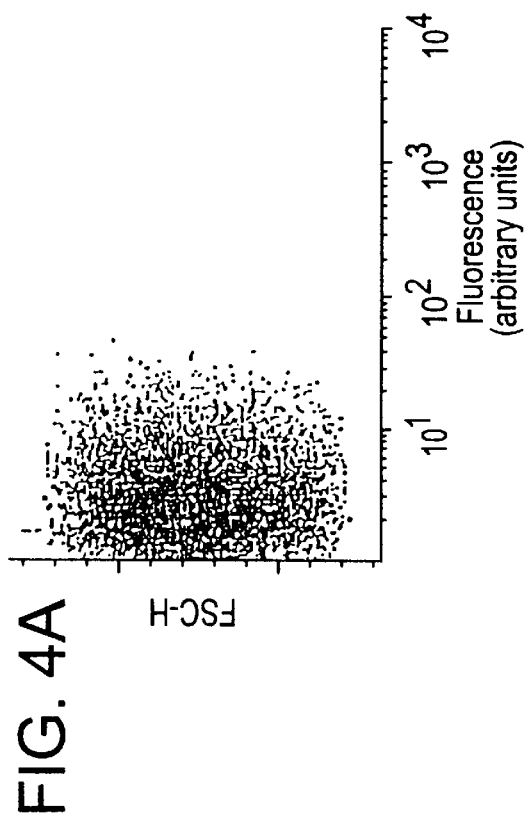
Figure 4D:
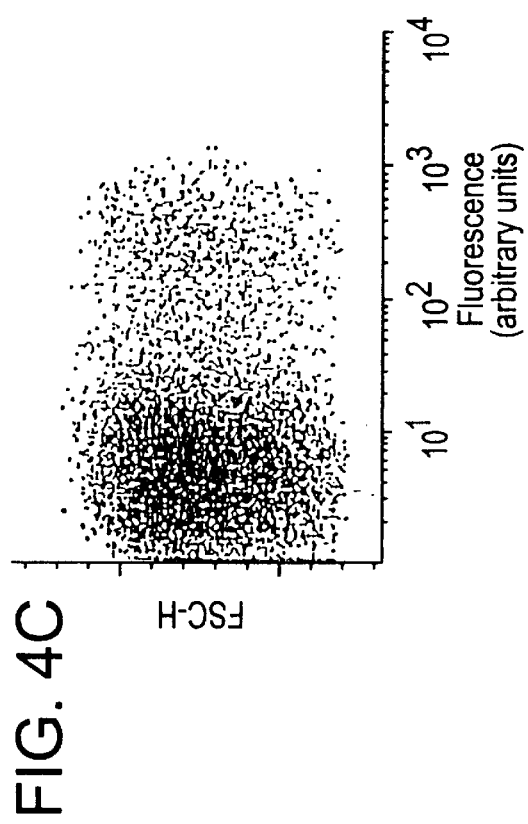

The tissue distribution of the murine genes was studied by northern analysis. Results are shown in FIG. 3. Probes from the 3' untranslated region of these genes which shared no appreciable homology among each other were used to avoid cross-hybridization of these genes. The expression pattern of mmFATP1 agrees with that previously found by Schaeffer and Lodish. mmFATP2 is expressed exclusively in liver and kidney, which corresponds with the reported tissue distribution of the rat homologue (VLACS), as assessed by western blot. mmFATP3 is expressed in lung, liver and testis, mmFATP4 in heart brain lung liver and kidney, and mmFATP5 is exclusively expressed in liver. The human homologue of mmFATP5, hsFATPs, is liver specific in humans and cannot be detected in a wide array of other tissues, including fetal liver. To assess whether the newly identified mouse genes are functional fatty acid transporters, Cos cells were transiently transfected with the genes and the uptake of a Bodipy-labeled analog of a long chain fatty acid by FACS was measured. When overexpressed in Cos cells, mmFATP1, mmFATP2 and mmFATP5 increase uptake of the Bodipy-labeled lauric acid (FIG. 4). Interestingly, when others et al. transfected the rat homologue of mmFATP2 into Cos cells, they observed an increase in very long chain acyl-CoA synthase activity, leading to the assumption that the protein was a VLACS. It appears that the increase in VLACS activity may be explained by previous data demonstrating that exogenously applied long chain fatty acids directly activate transcription of the long-chain acyl-CoA synthase gene. Thus, overexpression of mmFATP2 (or the rat homologue) may increase fatty acid uptake of cells from the media and subsequently lead to activation of VLACS gene expression.

All references cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated nucleic acid comprising the nucleotide sequence of SEQ ID NO.: 6 or the complement thereof.

2. An isolated nucleic acid which encodes a polypeptide comprising the amino acid sequence of SEQ ID NO.: 7 or the complement thereof.

3. An isolated nucleic acid which hybridizes to a nucleic acid comprising the nucleotide sequence of SEQ ID NO.: 6 under stringency conditions of 6×SSC at 65° C., followed by two or more washes in 0.2×SSC/0.5% SDS at 65° C.

4. An isolated nucleic acid consisting of the nucleotide sequence of SEQ ID NO.: 6 or the complement thereof.

5. An isolated nucleic acid which encodes a polypeptide consisting of the amino acid sequence of SEQ ID NO.: 7 or the complement thereof.

6. An isolated nucleic acid consisting of a nucleotide sequence having at least 95% identity to a nucleotide sequence of claim 1.

7. An isolated nucleic acid encoding a fusion polypeptide, wherein the isolated nucleic acid comprises the nucleotide sequence of SEQ ID NO.: 6.

8. A vector comprising a nucleic acid of any one of claims 1, 2, 3, 4, 5, 6, or, 7.

9. An isolated host cell transfected with the vector of claim 8.

10. A method of producing an isolated polypeptide comprising the step of culturing the host cell of claim 9 under conditions in which the nucleic acid is expressed, thereby producing the polypeptide.

11. An isolated nucleic acid comprising the nucleotide sequence of SEQ ID NO.: 8 or the complement thereof.

12. An isolated nucleic acid which encodes a polypeptide comprising the amino acid sequence of SEQ ID NO.: 9 or the complement thereof.

13. An isolated nucleic acid which hybridizes to a nucleic acid comprising the nucleotide sequence of SEQ ID NO.: 8 under stringency conditions of 6×SSC at 65° C., followed by two or more washes in 0.2×SSC/0.5% SDS at 65° C.

14. An isolated nucleic acid consisting of the nucleotide sequence of SEQ ID NO.: 8 or the complement thereof.

15. An isolated nucleic acid which encodes a polypeptide consisting of the amino acid sequence of SEQ ID NO.: 9 or the complement thereof.

16. An isolated nucleic acid consisting of a nucleotide sequence having at least 95% identity to a nucleotide sequence of claim 11.

17. An isolated nucleic acid encoding a fusion polypeptide, wherein the isolated nucleic acid comprises the nucleotide sequence of SEQ ID NO.: 8.

18. A vector comprising a nucleic acid of any one of claims 11, 12, 13, 14, 15, 16, or 17.

19. An isolated host cell transfected with the vector of claim 18.

20. A method of producing an isolated polypeptide comprising the step of culturing the host cell of claim 19 under conditions in which the nucleic acid is expressed, thereby producing the polypeptide.

21. An isolated nucleic acid comprising the nucleotide sequence of SEQ ID NO.: 10 or the complement thereof.

22. An isolated nucleic acid which encodes a polypeptide comprising the amino acid sequence of SEQ ID NO.: 11 or the complement thereof.

23. An isolated nucleic acid which hybridizes to a nucleic acid comprising the nucleotide sequence of SEQ ID NO.: 10 under stringency conditions of 6×SSC at 65° C., followed by two or more washes in 0.2×SSC/0.5% SDS at 65° C.

24. An isolated nucleic acid consisting of the nucleotide sequence of SEQ ID NO.: 10 or the complement thereof.

25. An isolated nucleic acid which encodes a polypeptide consisting of the amino acid sequence of SEQ ID NO.: 11 or the complement thereof.

26. An isolated nucleic acid consisting of a nucleotide sequence having at least 95% identity to a nucleotide sequence of claim 21.

27. An isolated nucleic acid encoding a fusion polypeptide, wherein the isolated nucleic acid comprises the nucleotide sequence of SEQ ID NO.: 10.

28. A vector comprising a nucleic acid of any one of claims 21, 22, 23, 24, 25, 26, or 27.

29. An isolated host cell transfected with the vector of claim 28.

30. A method of producing an isolated polypeptide comprising the step of culturing the host cell of claim 29 under conditions in which the nucleic acid is expressed, thereby producing the polypeptide.

31. An isolated nucleic acid comprising the nucleotide sequence of SEQ ID NO.: 12 or the complement thereof.

32. An isolated nucleic acid which encodes a polypeptide comprising the amino acid sequence of SEQ ID NO.: 13 or the complement thereof.

33. An isolated nucleic acid which hybridizes to a nucleic acid comprising the nucleotide sequence of SEQ ID NO.: 12 under stringency conditions of 6×SSC at 65° C., followed by two or more washes in 0.2×SSC/0.5% SDS at 65° C.

34. An isolated nucleic acid consisting of the nucleotide sequence of SEQ ID NO.: 12 or the complement thereof.

35. An isolated nucleic acid which encodes a polypeptide consisting of the amino acid sequence of SEQ ID NO.: 13 or the complement thereof.

36. An isolated nucleic acid consisting of a nucleotide sequence having at least 95% identity to a nucleotide sequence of claim 31.

37. An isolated nucleic acid encoding a fusion polypeptide, wherein the isolated nucleic acid comprises the nucleotide sequence of SEQ ID NO.: 12.

38. A vector comprising a nucleic acid of any one of claims 31, 32, 33, 34, 35, 36, or 37.

39. An isolated host cell transfected with the vector of claim 38.

40. A method of producing an isolated polypeptide comprising the step of culturing the host cell of claim 39 under conditions in which the nucleic acid is expressed, thereby producing the polypeptide.

41. An isolated nucleic acid comprising the nucleotide sequence of SEQ ID NO.: 14 or the complement thereof.

42. An isolated nucleic acid which encodes a polypeptide comprising the amino acid sequence of SEQ ID NO.: 15 or the complement thereof.

43. An isolated nucleic acid which hybridizes to a nucleic acid comprising the nucleotide sequence of SEQ ID NO.: 14 under stringency conditions of 6×SSC at 65° C., followed by two or more washes in 0.2×SSC/0.5% SDS at 65° C.

44. An isolated nucleic acid consisting of the nucleotide sequence of SEQ ID NO.: 14 or the complement thereof.

45. An isolated nucleic acid which encodes a polypeptide consisting of the amino acid sequence of SEQ ID NO.: 15 or the complement thereof.

46. An isolated nucleic acid consisting of a nucleotide sequence having at least 95% identity to a nucleotide sequence of claim 41.

47. An isolated nucleic acid encoding a fusion polypeptide, wherein the isolated nucleic acid comprises the nucleotide sequence of SEQ ID NO.: 14.

48. A vector comprising a nucleic acid of any one of claims 41, 42, 43, 44, 45, 46, or 47.

49. An isolated host cell transfected with the vector of claim 48.

50. A method of producing an isolated polypeptide comprising the step of culturing the host cell of claim 49 under conditions in which the nucleic acid is expressed, thereby producing the polypeptide.

51. An isolated nucleic acid comprising the nucleotide sequence of SEQ ID NO.: 16 or the complement thereof.

52. An isolated nucleic acid which encodes a polypeptide comprising the amino acid sequence of SEQ ID NO.: 17 or the complement thereof.

53. An isolated nucleic acid which hybridizes to a nucleic acid comprising the nucleotide sequence of SEQ ID NO.: 16 under stringency conditions of 6×SSC at 65° C., followed by two or more washes in 0.2×SSC/0.5% SDS at 65° C.

54. An isolated nucleic acid consisting of the nucleotide sequence of SEQ ID NO.: 16 or the complement thereof.

55. An isolated nucleic acid which encodes a polypeptide consisting of the amino acid sequence of SEQ ID NO.: 17 or the complement thereof.

56. An isolated nucleic acid consisting of a nucleotide sequence having at least 95% identity to a nucleotide sequence of claim 51.

57. An isolated nucleic acid encoding a fusion polypeptide, wherein the isolated nucleic acid comprises the nucleotide sequence of SEQ ID NO.: 16.

58. A vector comprising a nucleic acid of any one of claims 51, 52, 53, 54, 55, 56, or 57.

59. An isolated host cell transfected with the vector of claim 58.

60. A method of producing an isolated polypeptide comprising the step of culturing the host cell of claim 59 under conditions in which the nucleic acid is expressed, thereby producing the polypeptide.

61. An isolated nucleic acid comprising the nucleotide sequence of SEQ ID NO.: 18 or the complement thereof.

62. An isolated nucleic acid which encodes a polypeptide comprising the amino acid sequence of SEQ ID NO.: 19 or the complement thereof.

63. An isolated nucleic acid which hybridizes to a nucleic acid comprising the nucleotide sequence of SEQ ID NO.: 18 under stringency conditions of 6×SSC at 65° C., followed by two or more washes in 0.2×SSC/0.5% SDS at 65° C.

64. An isolated nucleic acid consisting of the nucleotide sequence of SEQ ID NO.: 18 or the complement thereof.

65. An isolated nucleic acid which encodes a polypeptide consisting of the amino acid sequence of SEQ ID NO.: 19 or the complement thereof.

66. An isolated nucleic acid consisting of a nucleotide sequence having at least 95% identity to a nucleotide sequence of claim 61.

67. An isolated nucleic acid encoding a fusion polypeptide, wherein the isolated nucleic acid comprises the nucleotide sequence of SEQ ID NO.: 18.

68. A vector comprising a nucleic acid of any one of claims 61, 62, 63, 64, 65, 66, or 67.

69. An isolated host cell transfected with the vector of claim 68.

70. A method of producing an isolated polypeptide comprising the step of culturing the host cell of claim 69 under conditions in which the nucleic acid is expressed, thereby producing the polypeptide.

71. An isolated nucleic acid comprising the nucleotide sequence of SEQ ID NO.: 20 or the complement thereof.

72. An isolated nucleic acid which encodes a polypeptide comprising the amino acid sequence of SEQ ID NO.: 21 or the complement thereof.

73. An isolated nucleic acid which hybridizes to a nucleic acid comprising the nucleotide sequence of SEQ ID NO.: 20 under stringency conditions of 6×SSC at 65° C., followed by two or more washes in 0.2×SSC/0.5% SDS at 65° C.

74. An isolated nucleic acid consisting of the nucleotide sequence of SEQ ID NO.: 20 or the complement thereof.

75. An isolated nucleic acid which encodes a polypeptide consisting of the amino acid sequence of SEQ ID NO.: 21 or the complement thereof.

76. An isolated nucleic acid consisting of a nucleotide sequence having at least 95% identity to a nucleotide sequence of claim 71.

77. An isolated nucleic acid encoding a fusion polypeptide, wherein the isolated nucleic acid comprises the nucleotide sequence of SEQ ID NO.: 20.

78. A vector comprising a nucleic acid of any one of claims 71, 72, 73, 74, 75, 76 or 77.

79. An isolated host cell transfected with the vector of claim 78.

80. A method of producing an isolated polypeptide comprising the step of culturing the host cell of claim 79 under conditions in which the nucleic acid is expressed, thereby producing the polypeptide.

\* \* \* \* \*